United States Patent [19]
Hirata et al.

[11] Patent Number: 6,008,224
[45] Date of Patent: Dec. 28, 1999

[54] PYRIMIDINE DERIVATIVES

[75] Inventors: Mitsuteru Hirata, Tsurugashima; Takeo Deushi, Sayama; Yoshio Takahashi, Iruma; Masahiro Tamura, Higashimurayama; Takeshi Ohshima, Kounosu; Toshiaki Oda, Higashimurayama; Hiroyuki Sonoki, Higashimatsuyama; Masami Shiratsuchi, Musashimurayama, all of Japan

[73] Assignee: Kowa Co., Ltd., Nagoya, Japan

[21] Appl. No.: 08/849,725

[22] PCT Filed: Dec. 19, 1995

[86] PCT No.: PCT/JP95/02605

§ 371 Date: Jun. 27, 1997

§ 102(e) Date: Jun. 27, 1997

[87] PCT Pub. No.: WO96/20177

PCT Pub. Date: Jul. 4, 1996

[30] Foreign Application Priority Data

Dec. 28, 1994 [JP] Japan .................... 6-327329
Jul. 5, 1995 [JP] Japan .................... 7-169454

[51] Int. Cl.[6] ............ C07D 401/04; A61K 31/505
[52] U.S. Cl. ............................... 514/269; 544/296
[58] Field of Search ..................... 544/296; 514/269

[56] References Cited

FOREIGN PATENT DOCUMENTS

| | | |
|---|---|---|
| 0 526 708 | 2/1993 | European Pat. Off. . |
| 0 633 259 | 1/1995 | European Pat. Off. . |
| 0 658 548 | 6/1995 | European Pat. Off. . |
| 5-222003 | 8/1993 | Japan . |
| WO 97/09318 | 3/1997 | WIPO . |

*Primary Examiner*—John M. Ford
*Attorney, Agent, or Firm*—Oblon, Spivak, McClelland, Maier & Neustadt, P.C.

[57] ABSTRACT

The present invention is directed to a pyrimidine derivative of the following formula (1) or a salt of the derivative:

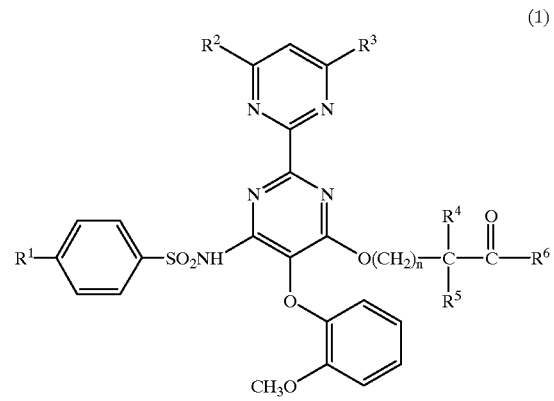

(1)

[wherein $R^1$ represents a lower alkyl group; each of $R^2$ and $R^3$ represents H, alkyl, or alkoxy; each of $R^4$ and $R^5$ represents H or alkyl; $R^6$ represents alkyl, $-OR^7$, or $-NR^8R^9$; and n is a number between 0 and 3 inclusive (wherein each of $R^7$, $R^8$, and $R^9$ represents H, alkyl, aryl, aralkyl, amino, a heterocyclic ring, etc.)], as well as to a medicine containing the derivative or salt as the active ingredient. The present compounds exhibit strong binding inhibitory activity against endothelin having potent vasoconstrictive effect and cell proliferation effect. Therefore, the compounds are effective as remedies for various diseases including circulatory diseases.

6 Claims, 1 Drawing Sheet

PYRIMIDINE DERIVATIVES

TECHNICAL FIELD

The present invention relates to novel pyrimidine derivatives and their salts, and to pharmaceuticals containing these compounds as active ingredients.

BACKGROUND ART

Endothelin, having potent vasoconstrictive effect, blood pressure elevating effect, and cell proliferation effect, is considered to be a substance that contributes to various diseases and disorders including heart diseases such as ischemic heart infarction, congestive heart failure, arrhythmia, and unstable angina; airway diseases such as asthma; hypertonia such as pulmonary hypertension, renal hypertension, and hypertension accompanying organ transplantation; circulatory diseases such as subarachnoid hemorrhage and post-PTCA reconstriction or vasospasm; kidney diseases such as acute and chronic renal failure; diabetes, hyperlipemia, and other diseases that are accompanied by vascular lesion, as well as arteriosclerosis; liver diseases such as alcohol-induced liver disorders; gastrointestinal disorders such as those of gastric mucosa; bone diseases; prostatic hypertrophy and urinary disorders; cancer; and skin diseases concurrent with proliferation of melanocytes [Saishin-Igaku (may be translated to "Medicine Up-to-date"), 94, 335–431(1994), Igaku-no-Ayumi (may be translated to "Progress of Medicine"), 168, 675–692(1994), Igaku-no-Ayumi, 170, 357(1994), Pharmac. Rev., 46, 325 (1994), and Gendai-Iryo (may be translated to "Modern Remedies"), 27, 1 (1995)].

It has come to be elucidated that a variety of actions of endothelin are triggered upon binding of endothelin to its receptors in organs of the body, and that the vasoconstriction caused by endothelin is induced by the mediation of at least two different receptors ($ET_A$ receptor and $ET_B$ receptor). Therefore, a compound that prevents endothelin from binding to these two receptors should be useful as a preventive and therapeutic agent for the above-mentioned diseases in which endothelin participates. Heretofore, a number of compounds have been reported as exhibiting endothelin antagonism [J. Med. Chem., 36, 2585 (1993), Nature, 365, 759(1993), Circulation, 88, 1–316 (1994), Saishin-Igaku, 94, 424–431(1994), J. Med. Chem. 37, 1553(1994), and Japanese Patent Application Laid-Open (kokai) No. 5-222003)].

However, there have not yet been found compounds that exhibit satisfactory endothelin antagonism.

Accordingly, the present invention is directed to the discovery of a compound that has potent endothelin antagonism, as well as to the provision of pharmaceuticals containing such a compound as the active ingredient.

DISCLOSURE OF THE INVENTION

Under the above circumstances, the present inventors carried out careful studies, and found that the pyrimidine derivatives represented by the following formula (1) and their salts exhibit excellent endothelin antagonism and thus are useful as medicines—particularly those for circulatory diseases. The present invention was accomplished based on this finding.

Accordingly, the present invention provides a pyrimidine derivative of the following formula (1) or a salt thereof:

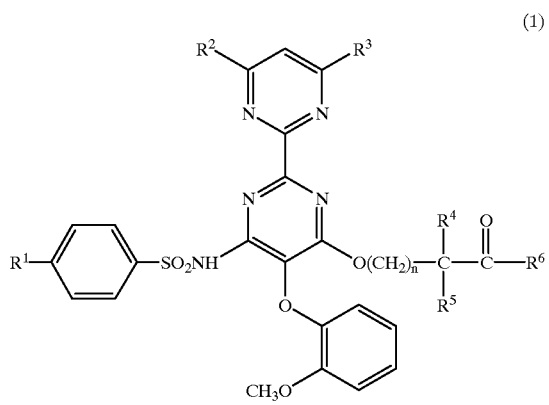

[wherein $R^1$ represents a lower alkyl group; each of $R^2$ and $R^3$, which are identical to or different from each other, represents a hydrogen atom, a lower alkyl group, or a lower alkoxyl group; each of $R^4$ and $R^5$, which are identical to or different from each other, represents a hydrogen atom or a lower alkyl group; $R^6$ represents a lower alkyl group, —$OR^7$, or —$NR^8R^9$; and n is a number between 0 and 3 inclusive (wherein $R^7$ represents a hydrogen atom, a lower alkyl group, a phenyl group which may have a substituent, or an aralkyl group which may have a substituent; and each of $R^8$ and $R^9$, which are identical to or different from each other, represents a hydrogen atom, a hydroxyl group, a lower alkyl group which may have a substituent, a lower alkenyl group which may have a substituent, an aryl group which may have a substituent, an aralkyl group which may have a substituent, an amino group which may have a substituent, a heterocyclic group which may have a substituent, a heterocyclic-alkyl group which may have a substituent, or $R^8$ and $R^9$ may be linked to each other so as to form a 5- to 7-membered ring along with their adjacent nitrogen atom)].

The present invention also provides a medicine containing a pyrimidine derivative of formula (1) or a salt thereof.

The present invention also provides a pharmaceutical composition containing a pyrimidine derivative of formula (1) or a salt thereof and a pharmaceutically acceptable carrier.

The present invention also provides use as a medicine of a pyrimidine derivative of formula (1) or a salt thereof.

The present invention also provides a method for treating diseases induced by endothelin, wherein the method is characterized by administering an effective amount of a pyrimidine derivative of formula (1) or a salt thereof.

BEST MODE FOR CARRYING OUT THE INVENTION

Figure 1:
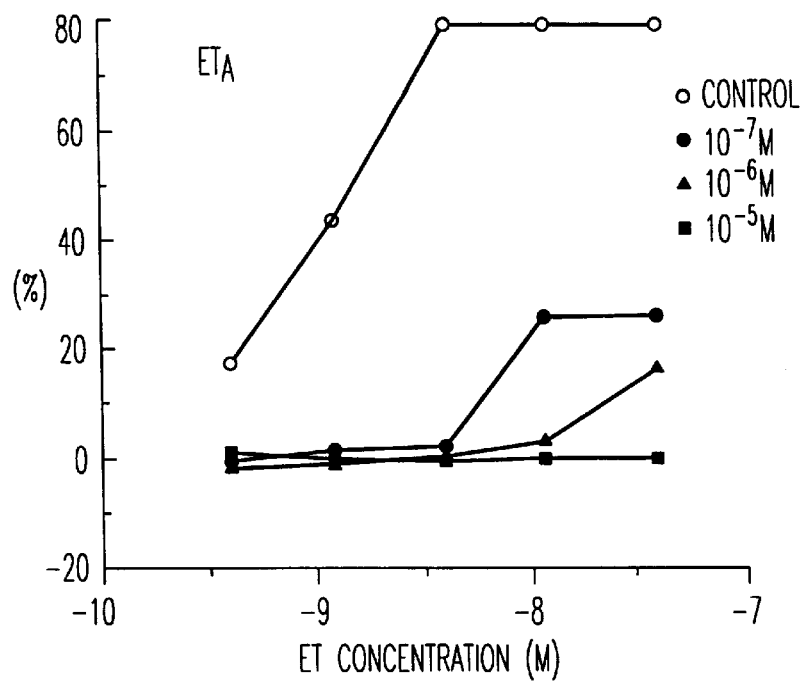
FIG. 1 is a graph showing the $ET_A$ receptor antagonism of Compound No. 92.

In the present invention, the term "lower" is used to indicate that the number of carbon atoms is between 1 and 6 inclusive.

In the formula (1), the lower alkyl groups represented by $R^1$, $R^2$, $R^3$, $R^4$, $R^5$, $R^6$, $R^7$, $R^8$, and $R^9$ include linear, branched, or cyclic alkyl groups having 1–6 carbon atoms, examples of which include methyl, ethyl, n-propyl, isopropyl, n-butyl, isobutyl, sec-butyl, tert-butyl, n-pentyl, n-hexyl, cyclopropyl, cyclopentyl, and cyclohexyl.

Of the listed groups, $R^1$ is preferably isopropyl or tert-butyl, with tert-butyl being particularly preferred.

The lower alkoxyl groups represented by $R^2$ and $R^3$ include linear, branched, or cyclic alkoxyl groups having 1–6 carbon atoms, examples of which include methoxy, ethoxy, n-propoxy, isopropoxy, and n-butoxy.

Examples of the phenyl group which may have a substituent and which is represented by $R^7$ include phenyl groups substituted by C1–C6 alkyl groups, C1–C6 alkoxyl groups, or by halogen atoms. Specific examples of such phenyl groups include methylphenyl, ethylphenyl, isopropylphenyl, methoxyphenyl, ethoxyphenyl, chlorophenyl, bromophenyl, and fluorophenyl.

The aralkyl groups which may have substituents and which are represented by $R^7$, $R^8$, and $R^9$ include phenylalkyl groups, naphthylalkyl groups, biphenylalkyl groups, and indanyl groups. These groups may be substituted by hydroxy, C1–C6 alkyl, C1–C6 alkoxyl, C1–C3 alkylenedioxy, halogen, nitro, trifluoromethyl, or cyano groups. Examples of the alkyl moieties of the aralkyl groups include C1–6 alkyl groups. The aralkyl groups may be substituted by one to three groups of the above-mentioned substituents. These substituents may be substituted at either the aryl moiety or the alkyl moiety of the aralkyl group. Specific examples of the aralkyl groups which may have substituents include benzyl, phenethyl, phenylpropyl, naphthylmethyl, naphthylethyl, biphenylmethyl, and indan-1-yl groups, and these groups may be substituted by one to three groups selected from among the groups consisting of chloro, fluoro, methoxy, ethoxy, methyl, ethyl, nitro, cyano, and trifluoromethyl groups.

The lower alkyl groups which may have substituents and which are represented by $R^8$ and $R^9$ include, in addition to the lower alkyl groups listed for $R^1$ through $R^9$ groups, alkyl groups substituted by one to three halogen atoms, hydroxyl groups, etc.

The lower alkenyl groups which may have substituents include linear, branched, or cyclic alkenyl groups having 2–6 carbon atoms, as well as the same groups substituted by one to three halogen atoms, hydroxyl groups, etc. Specific examples include vinyl, propenyl, and isobutenyl groups.

Examples of the aryl group may be phenyl or naphthyl which may be substituted by one to three C1–C6 alkyl groups, C2–C6 alkenyl groups, C1–C6 alkoxyl groups, C1–C6 alkylthio groups, halogen atoms, hydroxy groups, amino groups, nitro groups, alkoxycarbonyl groups or C1–C6 haloalkyl groups, etc. Specific examples of the aryl group which may have a substituent include phenyl, naphthyl, mono- or di-chlorophenyl, mono- or di-fluorophenyl, mono-, di-, or tri-methoxyphenyl, mono- or di-methylphenyl, mono- or di-ethylphenyl, mono- or di-isopropylphenyl, tert-butylphenyl, isopropenylphenyl, hydroxyphenyl, nitrophenyl, aminophenyl, ethoxycarbonylphenyl, and methylthiophenyl.

Examples of the amino groups which may have substituents and which are represented by $R^8$ and $R^9$ include arylamino groups, heterocyclic amino groups, alkylamino groups, and alkenylamino groups. More specifically, mention may be given to phenylamino groups, C1–C6 alkyl-substituted phenylamino groups, pyridylamino groups, and C1–C6 alkylamino groups.

Examples of the heterocyclic group which may have a substituent or the heterocyclic-alkyl group which may have a substituent include furyl groups, thienyl groups, pyrazolyl groups, thiazolyl groups, thiadiazolyl groups, imidazolyl groups, pyridyl groups, pyrimidinyl groups, pyrazinyl groups, furylalkyl groups, thienylalkyl groups, pyrazolylalkyl groups, thiazolylalkyl groups, imidazolylalkyl groups, pyridylalkyl groups, and pyrimidinylalkyl groups, and these groups may be substituted by C1–C6 alkyl groups, C1–C6 alkoxyl groups, C1–C6 haloalkyl groups, or halogen atoms. Specific examples include furyl groups, thienyl groups, pyrazolyl groups, thiazolyl groups, pyridyl groups, pyrimidinyl groups, pyrazinyl groups, furfuryl groups, thienylmethyl groups, pyrazolylmethyl groups, thiazolylmethyl groups, imidazolylmethyl groups, pyridylmethyl groups, and pyrimidinylmethyl groups, all of which groups may be substituted by a group selected from among the groups consisting of methyl, ethyl, methoxy, ethoxy, chloro, fluoro, and trifluoromethyl.

Examples of the 5- to 7-membered ring formed by —$NR^8R^9$ include pyrrolidinyl groups, piperidinyl groups, and perhydroazepinyl groups.

The salts of the compound (1) of the present invention are not particularly limited so long as they are pharmaceutically acceptable. Examples of the salts include mineral acid salts such as hydrochloric acid salts and sulfuric acid salts; organic acid salts such as acetic acid salts, oxalic acid salts, and citric acid salts; alkali metal salts such as sodium salts and potassium salts, alkaline earth metal salts such as calcium salts and magnesium salts; and salts of organic bases such as 1,8-diazabicyclo[5.4.0]undec-7-ene (DBU) salts.

Also, the compound (1) of the present invention encompasses its hydrates and solvates.

The compound (1) of the present invention may be prepared in accordance with the following reaction scheme.

Reaction scheme (A)
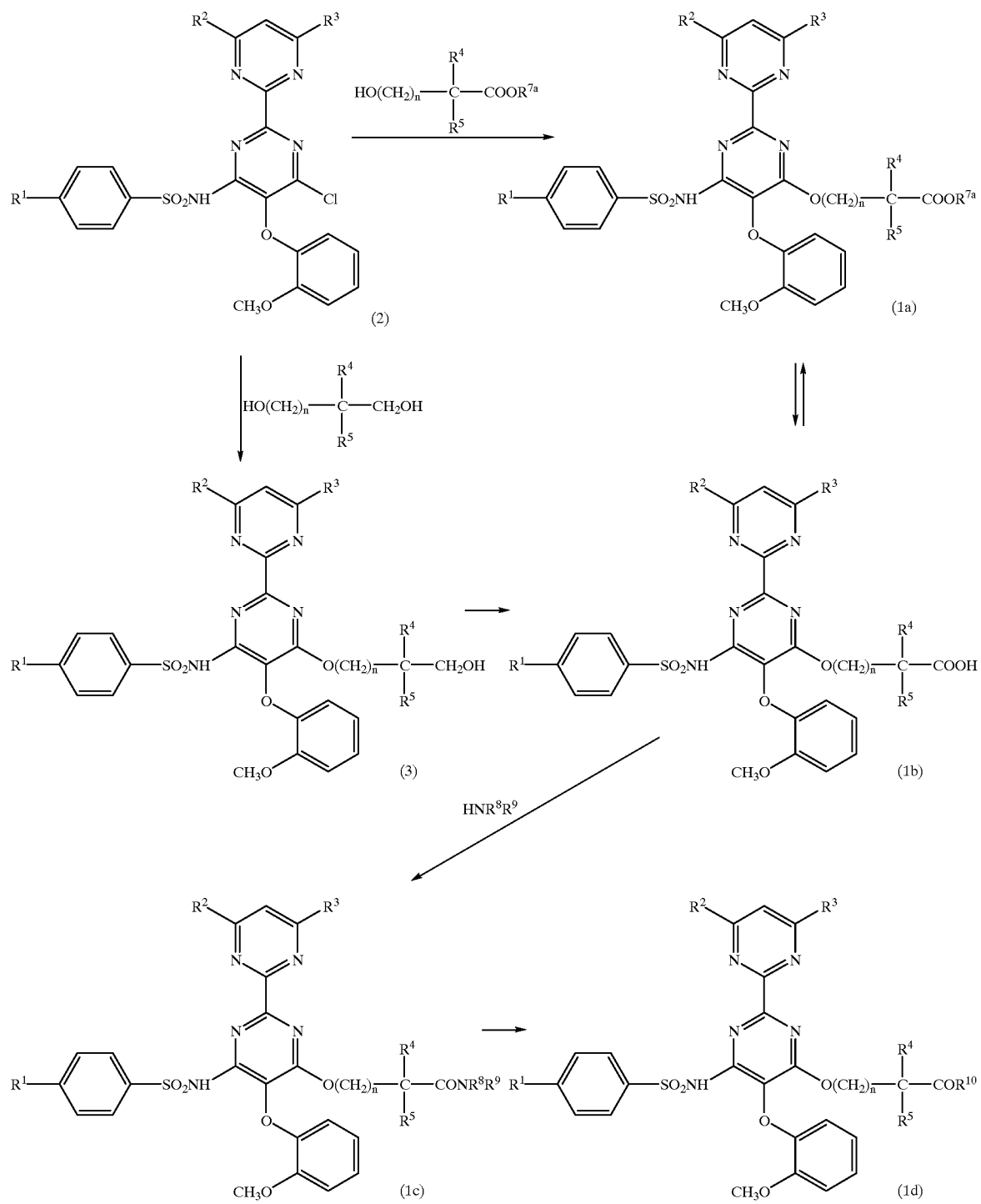
[wherein $R^1$, $R^2$, $R^3$, $R^4$, $R^5$, $R^8$, $R^9$, and n have the same meanings as defined above, $R^{7a}$ represents a lower alkyl group, a substituted or unsubstituted phenyl group, or a substituted or unsubstituted aralkyl group, and $R^{10}$ represents a lower alkyl group].
Briefly, a compound (2) is reacted with a hydroxy fatty acid ester
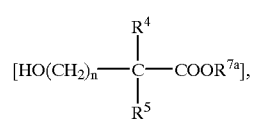

to obtain a compound (1a). Independently, a compound (2) is reacted with an alcohol

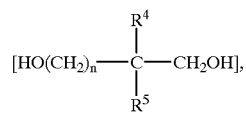

to obtain a compound (3), and the thus-obtained compound (3) is oxidized to afford a compound (1b). Compounds (1a) and (1b) are mutually transformable through hydrolysis or esterification. When compound (1b) is reacted with an amine [$HNR^8R^9$], a compound (1c) is obtained. The obtained compound (1c) affords a compound (1d) through a nucleophilic reaction by use of an organic metal reagent.

The compounds (2) and (3) are known compounds and can be obtained by a known method (see Japanese Patent Application Laid-Open (kokai) No. 5-222003). Each step of the above-described reaction scheme will next be described.

Method for Obtaining Compound (1a) From Compound (2):

Compound (2) may be reacted with a hydroxy fatty acid ester without use of any solvent or in a polar solvent such as N,N-dimethylformamide (DMF) or dimethylsulfoxide (DMSO), in the presence of a base such as sodium, sodium hydride, potassium hydride, potassium t-butoxide, or potassium carbonate.

Method for Obtaining Compound (1b) From Compound (3):

Compound (3) may be placed in a polar solvent such as DMF, acetone, etc., and oxidized through use of an oxidizer such as chromate typified by pyridinium dichromate (PDC) and a Jones reagent, ruthenium chloride-sodium periodide, etc. Method for obtaining compound (1b) from compound (1a):

Compound (1a) may be subjected to a conventional hydrolysis using, for example, an alkali (NaOH, KOH, etc.). Method for obtaining compound (1a) from compound (1b):

Compound (1b) may be esterified by use of the following materials or methods: (1) use of an acid catalyst (e.g., sulfuric acid, hydrochloric acid, p-toluenesulfonic acid), (2) use of a dehydration-condensing agent (use of a dehydration-condensing agent such as dicyclohexylcarbodiimide (DCC) or 1-(3-dimethylaminopropyl)-3-ethylcarbodiimide (WSC) in the presence or absence of dimethylaminopyridine), (3) a method via an acid chloride by use of thionyl chloride or oxalyl chloride, (4) a method via an acid anhydride mixture by use of ethyl chlorocarbonate, isobutyl chlorocarbonate, etc., and (5) a method in which the alcohol moiety is activated with thionyl chloride, etc.

Method for Obtaining Compound (1c) From Compound (1b):

Compound (1b) may be amidified by use of the following materials or methods: (1) use of a dehydration-condensing agent such as DCC or WSC, (2) a method via an active ester (a phenyl ester such as p-nitrophenyl ester, N-hydroxybenzotriazol ester, N-hydroxysuccinimide ester, etc.) produced by use of the above-mentioned dehydration-condensing agent, (3) a method via an acid chloride by use of thionyl chloride or oxalyl chloride, (4) a method via an acid anhydride mixture by use of ethyl chlorocarbonate, isobutyl chlorocarbonate, etc., (5) a method in which a Woodward K reagent is used, and (6) a method in which a reagent ordinarily used for amidification (such as N-ethyl-2'-hydroxybenzoisoxazolium trifluoroborate, N-ethyl-5-phenylisoxazolium-3'-sulfonate, 1-ethoxycarbonyl-2-ethoxy-1,2-dihydroxyquinoline, benzotriazolyl-N-hydroxytrisdimethylaminophosphonium hexafluorophosphate salts, and diphenylphosphoryl azide) is used.

Method for Obtaining Compound (1d) From Compound (1c):

Compound (1c) may be alkylated by use of any of the following organic metallic reagents (a)–(d): (a) organic magnesium reagents, (b) organic lithium reagents, (c) organic copper reagents, and (d) organic zinc reagents.

Compound (1b) of the present invention may also be prepared through the following reaction scheme (B) or (C).

Reaction scheme (B):
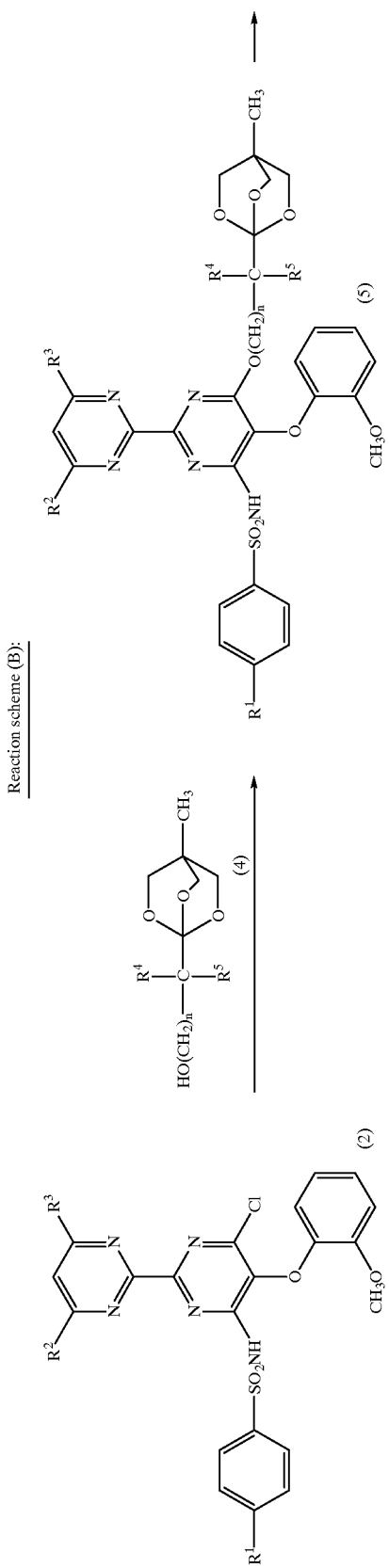

-continued
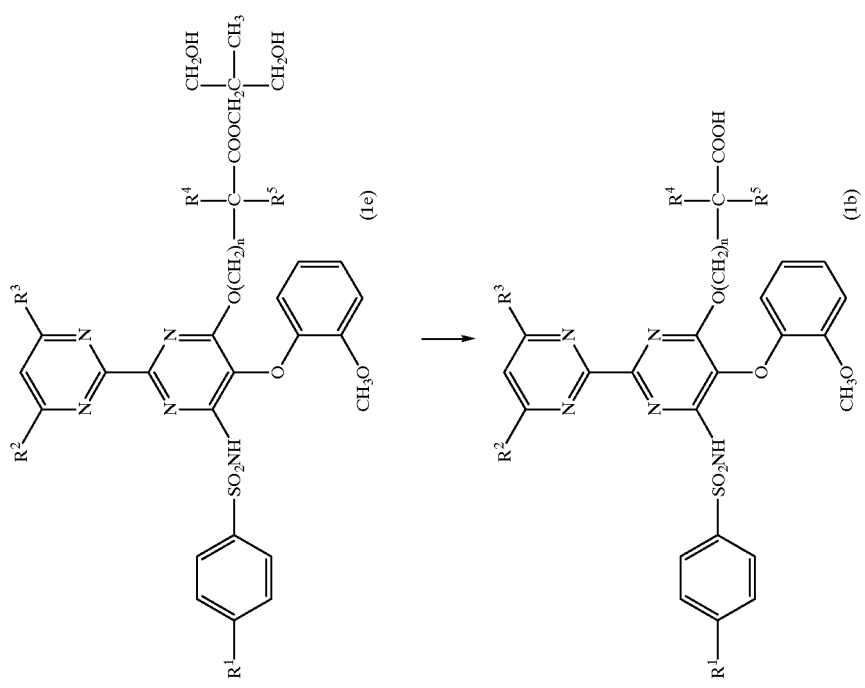

[wherein $R^1$, $R^2$, $R^3$, $R^4$, $R^5$, and n have the same meanings as defined above].

Briefly, compound (2) is reacted with alcohol (4) to obtain an ether compound (5). When the compound (5) is subjected to hydrolysis, a compound (1e) is obtained. After the ester moiety of the compound (1e) is hydrolyzed, a compound (1b) can be obtained.

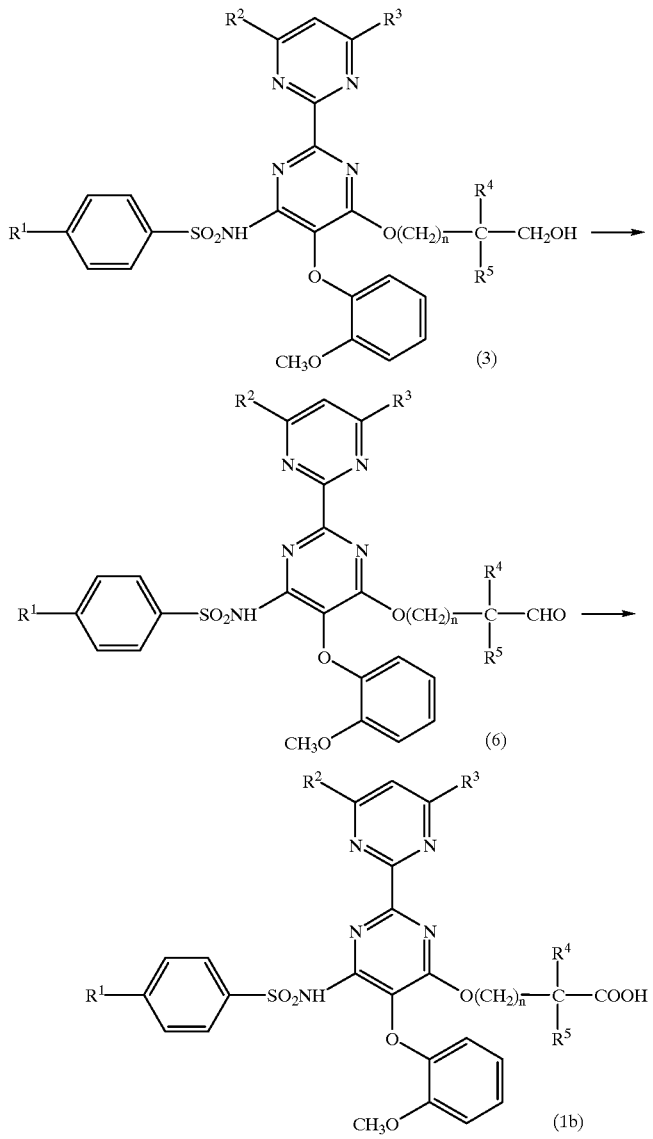

[wherein $R^1$, $R^2$, $R^3$, $R^4$, $R^5$, and n have the same meanings as defined above].

According to the reaction scheme (C), compound (3) is oxidized to be transformed into an aldehyde (6). When the aldehyde (6) is further oxidized, compound (1b) can be obtained.

Typical compounds of formula (1) of the present invention are shown in the following Tables 1 through 9. In the Tables, Me stands for methyl, Et stands for ethyl, t-Bu stands for tert-butyl, i-Pr stands for isopropyl, n-Pen stands for n-pentyl, n-Hex stands for n-hexyl, Ph stands for phenyl, and Bn stands for benzyl.

TABLE 1

[Structure: 4-tert-butylphenyl-SO₂NH — pyrimidine (with 2-pyrimidinyl substituent, 2-methoxyphenoxy substituent) — O(CH₂)ₙCH₂COOR⁷ (1a), (1b) or (1e)]

| Compound No. | n | R⁷ |
|---|---|---|
| 1 | 0 | Et |
| 2 | 0 | H |
| 3 | 1 | H |
| 4 | 2 | H |
| 5 | 3 | H |
| 6 | 3 | i-Pr |
| 7 | 1 | Bn |
| 8 | 1 | n-Hex |
| 9 | 1 | Et |
| 10 | 0 | Bn |
| 11 | 2 | —CH₂—C₆H₄—OMe |
| 12 | 0 | 3-chlorophenylmethyl |
| 66 | 0 | Me |
| 67 | 2 | Me |
| 69 | 1 | i-Pr |
| 108 | 1 | Me |
| 109 | 1 | —CH₂—C(CH₂OH)(CH₃)(CH₂OH) |

TABLE 2

| Compound No. | R¹ | R² | R³ | n | R⁴ | R⁵ | R⁷ |
|---|---|---|---|---|---|---|---|
| 110 | t-Bu | H | H | 1 | Me | Me | H |
| 111 | t-Bu | H | H | 1 | Et | Et | H |
| 112 | t-Bu | H | H | 1 | H | Me | H |
| 117 | t-Bu | Me | Me | 1 | H | H | H |
| 118 | t-Bu | EtO | EtO | 1 | H | H | H |
| 119 | t-Bu | i-PrO | i-PrO | 1 | H | H | H |
| 124 | i-Pr | H | H | 1 | H | H | H |

TABLE 3

(1c)

| Compound No. | n | R⁸ | R⁹ |
|---|---|---|---|
| 13 | 1 | H | H |
| 14 | 1 | H | Bn |
| 15 | 0 | H | Bn |
| 16 | 2 | H | Bn |
| 17 | 1 | H | —CH₂—C₆H₄—OMe (4-OMe) |
| 18 | 1 | H | Ph |
| 19 | 3 | H | Bn |
| 20 | 1 | H | —CH₂—(benzo[1,3]dioxol-5-yl) |

TABLE 3-continued (1c)

| Compound No. | n | R⁸ | R⁹ |
|---|---|---|---|
| 21 | 1 | H | —CH₂—C₆H₄—Cl (4-Cl) |
| 22 | 1 | H | —(CH₂)₂—C₆H₄—Cl (2-Cl) |
| 23 | 1 | H | —(CH₂)₂—C₆H₄—OMe (4-OMe) |
| 24 | 0 | H | —(CH₂)₂—Ph |
| 25 | 2 | H | Ph |
| 26 | 1 | H | —C₆H₄—OMe (3-OMe) |
| 27 | 1 | H | —(CH₂)₂—Ph |

TABLE 3-continued
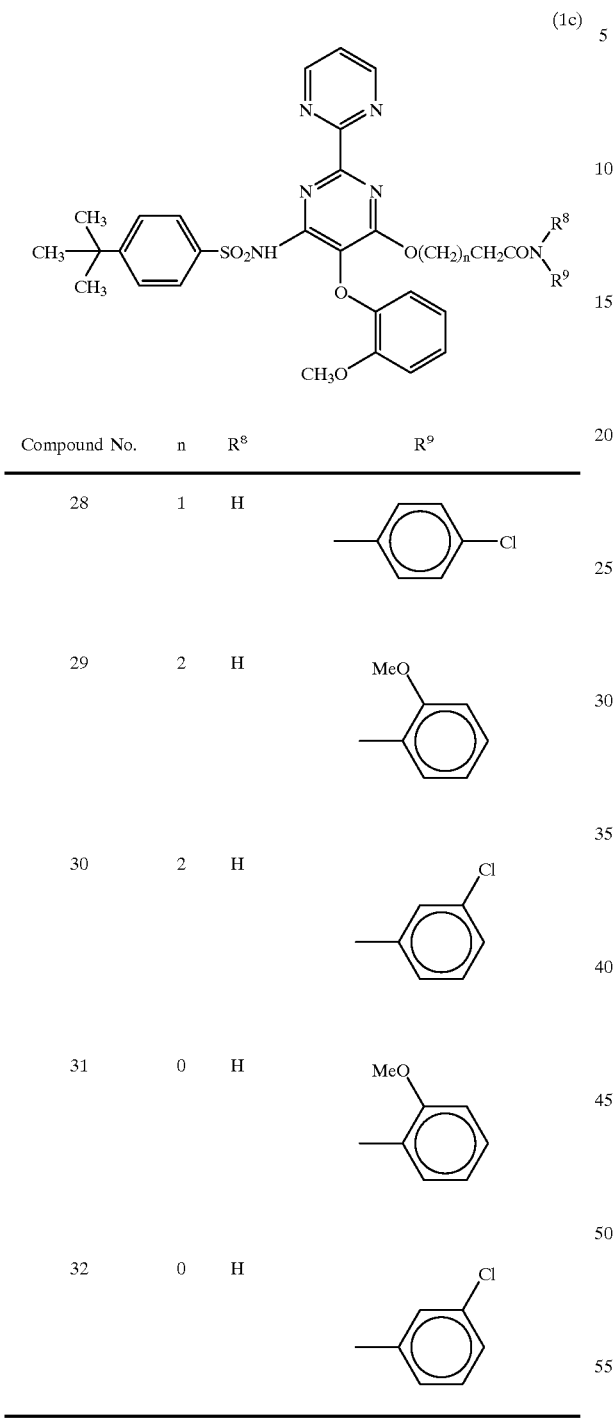
(1c)
| Compound No. | n | R⁸ | R⁹ |
|---|---|---|---|
| 28 | 1 | H | 4-Cl-phenyl |
| 29 | 2 | H | 2-MeO-phenyl |
| 30 | 2 | H | 3-Cl-phenyl |
| 31 | 0 | H | 2-MeO-phenyl |
| 32 | 0 | H | 3-Cl-phenyl |
TABLE 4
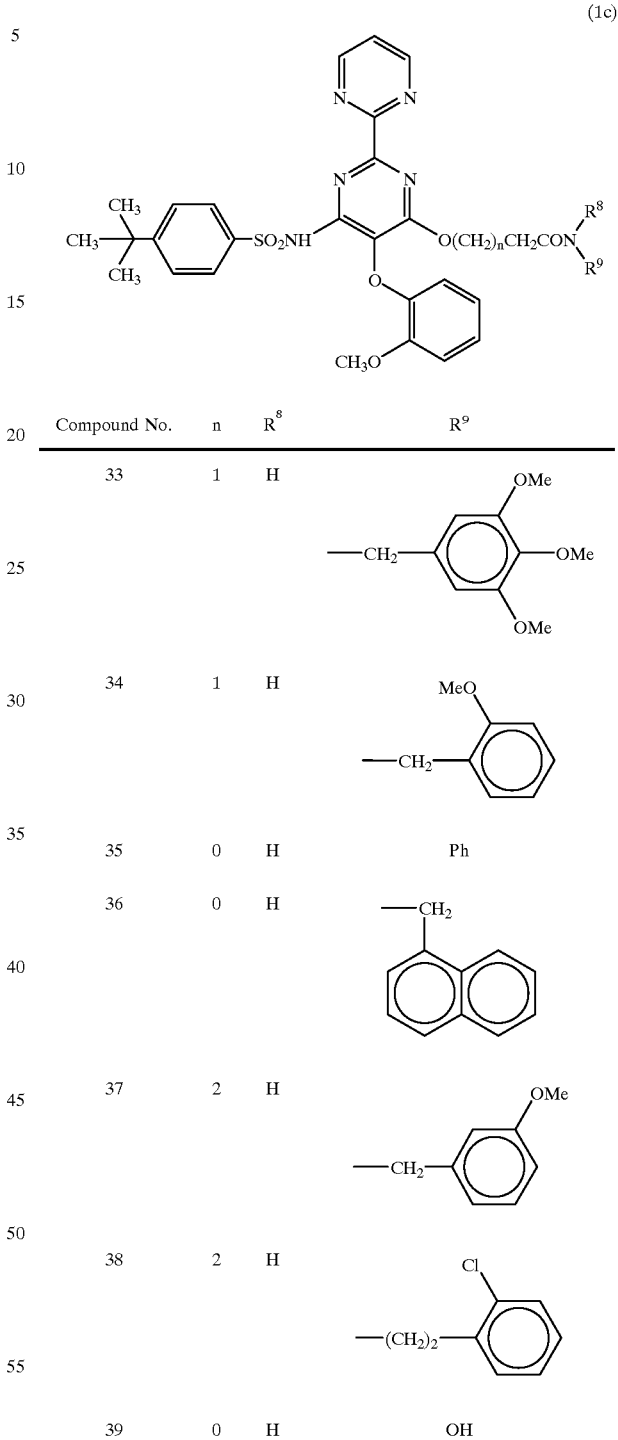
(1c)
| Compound No. | n | R⁸ | R⁹ |
|---|---|---|---|
| 33 | 1 | H | —CH₂-(3,4,5-triOMe-phenyl) |
| 34 | 1 | H | —CH₂-(2-MeO-phenyl) |
| 35 | 0 | H | Ph |
| 36 | 0 | H | —CH₂-(1-naphthyl) |
| 37 | 2 | H | —CH₂-(3-OMe-phenyl) |
| 38 | 2 | H | —(CH₂)₂-(2-Cl-phenyl) |
| 39 | 0 | H | OH |

TABLE 4-continued
(1c)
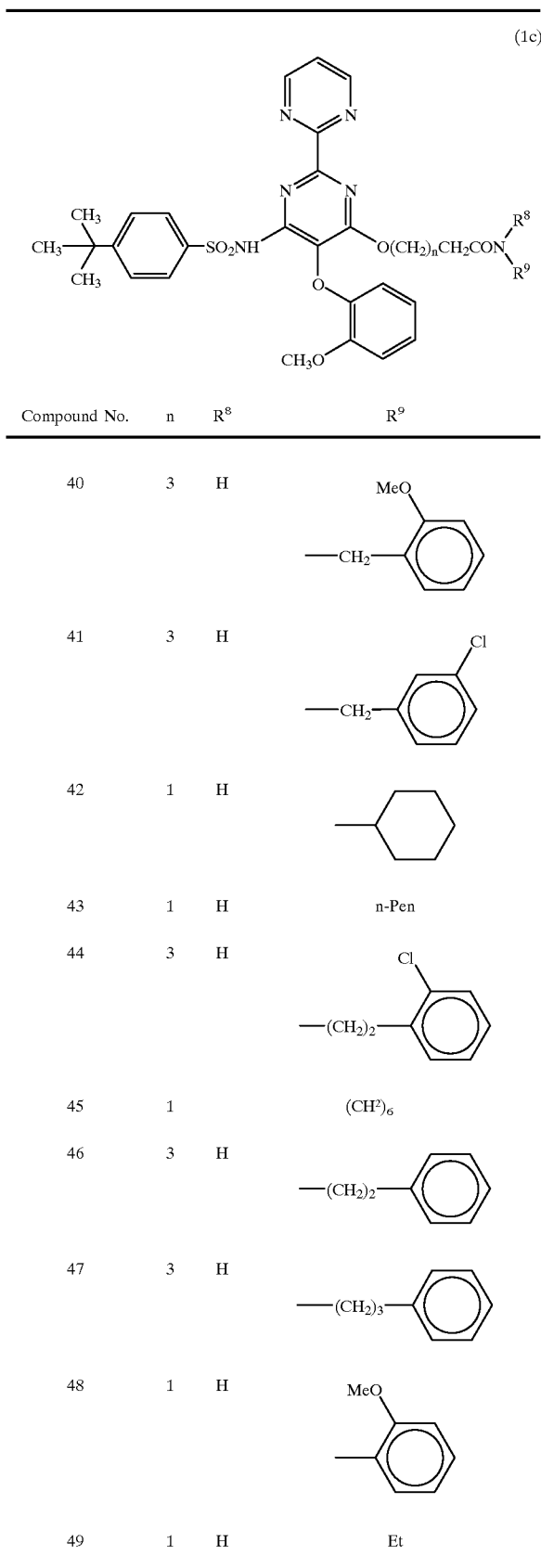
| Compound No. | n | R⁸ | R⁹ |
|---|---|---|---|
| 40 | 3 | H | -CH₂-(2-MeO-C₆H₄) |
| 41 | 3 | H | -CH₂-(2-Cl-C₆H₄) |
| 42 | 1 | H | cyclohexyl |
| 43 | 1 | H | n-Pen |
| 44 | 3 | H | -(CH₂)₂-(2-Cl-C₆H₄) |
| 45 | 1 | (CH²)₆ | |
| 46 | 3 | H | -(CH₂)₂-C₆H₅ |
| 47 | 3 | H | -(CH₂)₃-C₆H₅ |
| 48 | 1 | H | -(2-MeO-C₆H₄) |
| 49 | 1 | H | Et |
TABLE 4-continued
(1c)
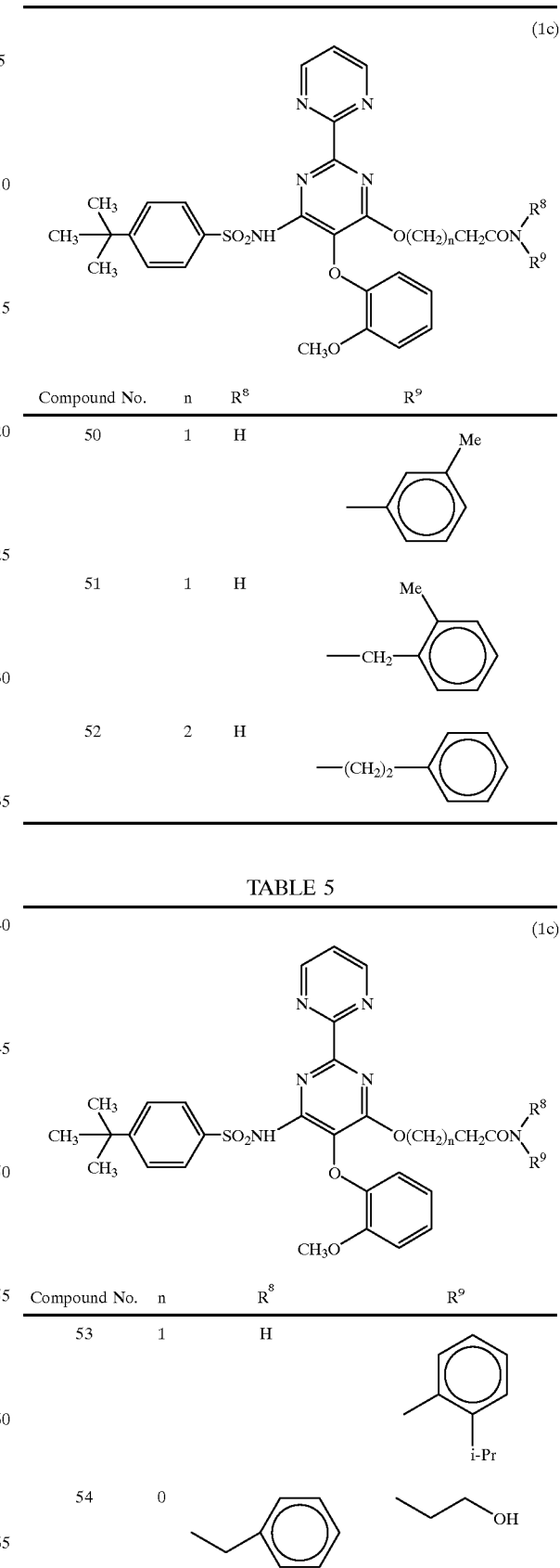
| Compound No. | n | R⁸ | R⁹ |
|---|---|---|---|
| 50 | 1 | H | 3-Me-C₆H₄ |
| 51 | 1 | H | -CH₂-(2-Me-C₆H₄) |
| 52 | 2 | H | -(CH₂)₂-C₆H₅ |
TABLE 5
(1c)
| Compound No. | n | R⁸ | R⁹ |
|---|---|---|---|
| 53 | 1 | H | 2-Me-6-i-Pr-C₆H₃ |
| 54 | 0 | 4-Et-C₆H₄ | -(CH₂)₃-OH |

TABLE 5-continued (1c)

[Structure: 4-tert-butylphenyl-SO2NH group and 2-methoxyphenoxy group on pyrimidine with 2-pyrimidinyl substituent and O(CH2)nCH2CON(R8)(R9) side chain]

| Compound No. | n | R⁸ | R⁹ |
|---|---|---|---|
| 55 | 1 | H | 2-ethylpyridine |
| 56 | 1 | H | 2-propylpyridine |
| 57 | 1 | H | α-methylbenzyl |
| 58 | 1 | Me | benzyl (ethylphenyl) |
| 59 | 1 | Me | tolyl |
| 60 | 1 | H | 2-(trifluoromethyl)benzyl |
| 61 | 1 | H | 2-furylmethyl |
| 62 | 0 | H | 2-methoxybenzyl |

TABLE 5-continued (1c)

[Same core structure as above]

| Compound No. | n | R⁸ | R⁹ |
|---|---|---|---|
| 63 | 0 | H | α-methylbenzyl |
| 64 | 1 | H | 2-methylthiazol-yl |
| 65 | 1 | H | 2,5-dimethoxy-4-methylphenyl |
| 68 | 1 | H | 2,6-dimethylphenyl (with additional Me) |
| 70 | 1 | H | 2-hydroxy-methylphenyl |
| 71 | 1 | H | 2-phenyl-2-hydroxypropyl |

TABLE 5-continued
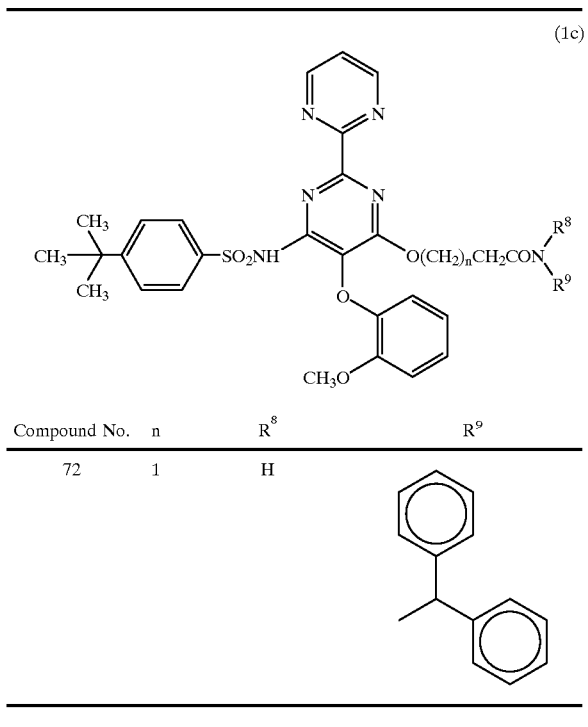
| Compound No. | n | R⁸ | R⁹ |
|---|---|---|---|
| 72 | 1 | H | (1-phenylethyl)phenyl group |
TABLE 6
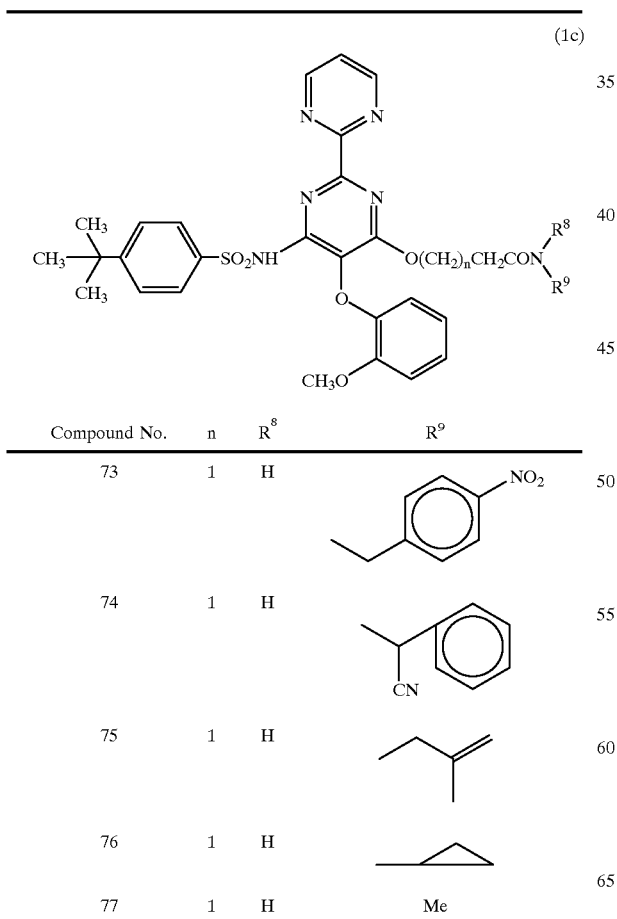
| Compound No. | n | R⁸ | R⁹ |
|---|---|---|---|
| 73 | 1 | H | 4-nitrobenzyl |
| 74 | 1 | H | α-cyanobenzyl |
| 75 | 1 | H | 2-methylallyl |
| 76 | 1 | H | cyclopropyl |
| 77 | 1 | H | Me |
TABLE 6-continued
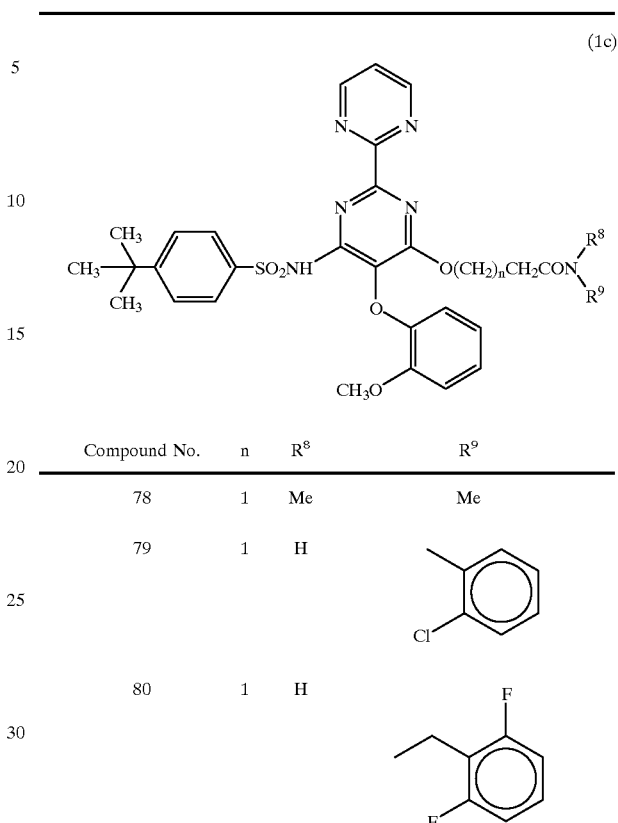
| Compound No. | n | R⁸ | R⁹ |
|---|---|---|---|
| 78 | 1 | Me | Me |
| 79 | 1 | H | 2-chloro-6-methylphenyl |
| 80 | 1 | H | 2,6-difluoro-substituted benzyl |
| 81 | 1 | H | 1-methylindanyl |
| 82 | 1 | H | 2-thienylmethyl |
| 83 | 1 | H | 2,4-dimethoxybenzyl |
| 84 | 1 | H | 1-ethyl-5-methylpyrazolyl |
| 85 | 1 | H | 2-methyl-6-(trifluoromethyl)phenyl |

TABLE 6-continued (1c)
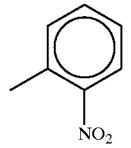

| Compound No. | n | R⁸ | R⁹ |
|---|---|---|---|
| 86 | 1 | H | 2-methyl-nitrobenzene (o-methyl, NO₂) |
| 87 | 1 | H | 2-methyl-benzoate ethyl ester (o-methyl, COOEt) |

TABLE 7

(1c)

| Compound No. | n | R⁸ | R⁹ |
|---|---|---|---|
| 88 | 1 | H | 2-methyl-5-(trifluoromethyl)-1,3,4-thiadiazole |
| 89 | 1 | H | 2-methyl-6-ethylphenyl |

TABLE 7-continued (1c)
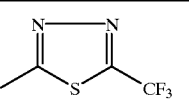

| Compound No. | n | R⁸ | R⁹ |
|---|---|---|---|
| 90 | 1 | H | 2-methyl-aniline (o-methyl, NH₂) |
| 91 | 1 | H | N-methylanilino (NH-phenyl) |
| 92 | 1 | H | 2-methylpyridin-3-yl |
| 93 | 1 | H | 2-methyl-6-(1-methylvinyl)phenyl |
| 94 | 1 | H | 2-methyl-6-(methylthio)phenyl (SMe) |
| 95 | 1 | H | 2-methyl-6-tert-butylphenyl |
| 96 | 1 | H | 2-methylpyridin-5-yl |
| 97 | 0 | H | 2-methylpyridin-6-yl |

TABLE 7-continued
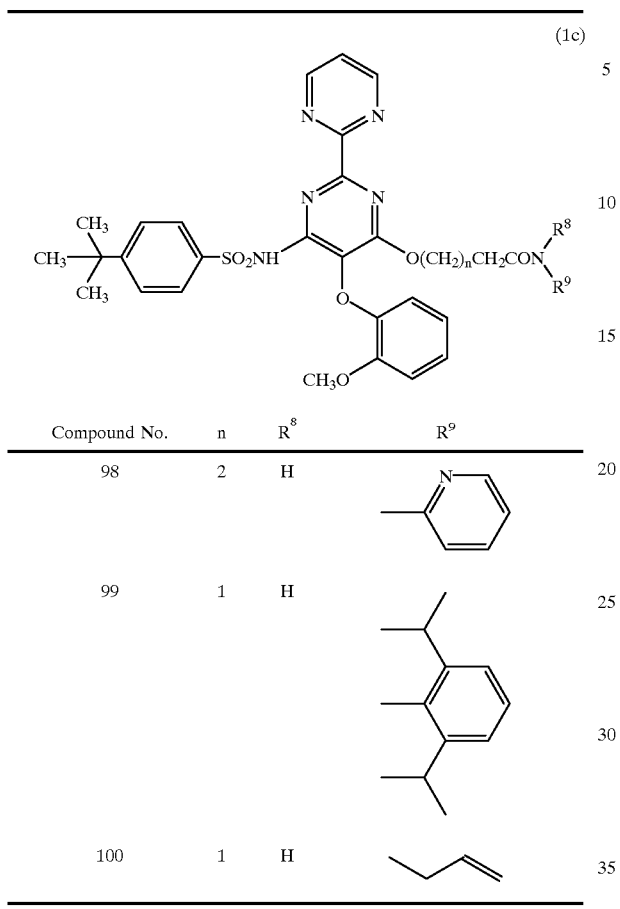
(1c)
| Compound No. | n | R⁸ | R⁹ |
|---|---|---|---|
| 98 | 2 | H | 2-methylpyridinyl |
| 99 | 1 | H | 2,6-diisopropyl-phenyl |
| 100 | 1 | H | allyl (CH₂CH=CH₂) |
TABLE 8
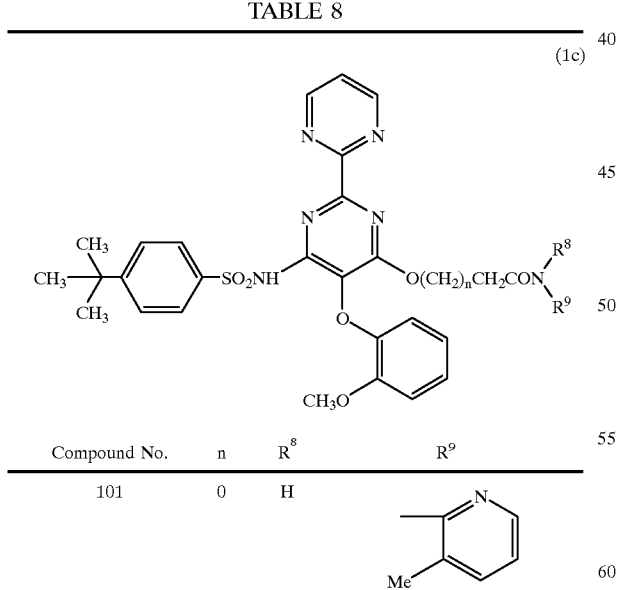
(1c)
| Compound No. | n | R⁸ | R⁹ |
|---|---|---|---|
| 101 | 0 | H | 2-methyl-3-Me-pyridinyl |
TABLE 8-continued
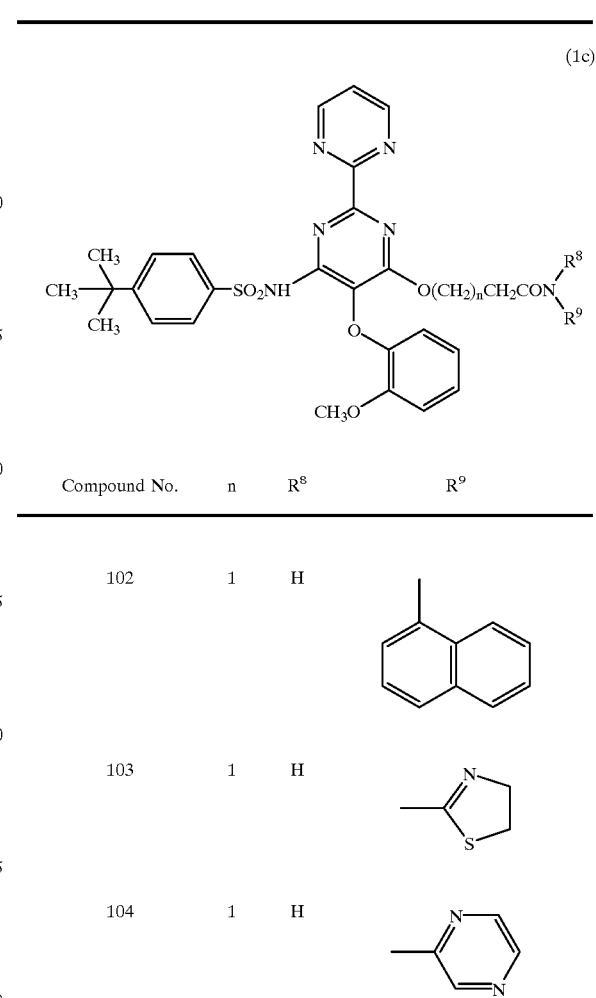
(1c)
| Compound No. | n | R⁸ | R⁹ |
|---|---|---|---|
| 102 | 1 | H | 1-methylnaphthyl |
| 103 | 1 | H | 2-methyl-thiazolinyl |
| 104 | 1 | H | 3-methylpyrazinyl |
| 105 | 1 | H | 2-methylpyrimidinyl |
| 106 | 0 | H | 2-pyridinyl-NH- |
| 107 | 1 | H | 2-pyridinyl-NH- |

TABLE 9

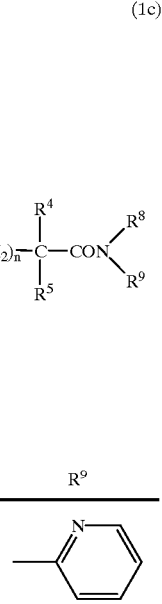

(1c)

| Compound No. | R¹ | R² | R³ | n | R⁴ | R⁵ | R⁸ | R⁹ |
|---|---|---|---|---|---|---|---|---|
| 113 | t-Bu | H | H | 1 | H | Me | H | 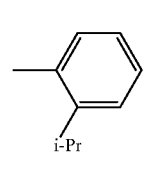 |
| 114 | t-Bu | H | H | 1 | H | Me | H | 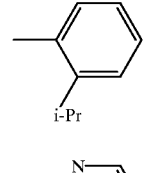 i-Pr |
| 115 | i-Pr | H | H | 1 | H | H | H | 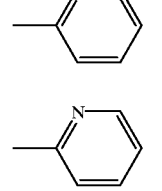 i-Pr |
| 116 | i-Pr | H | H | 1 | H | H | H | 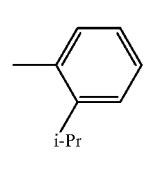 |
| 120 | t-Bu | Me | Me | 1 | H | H | H | 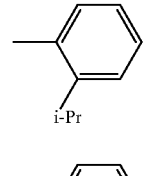 |
| 121 | t-Bu | Me | Me | 1 | H | H | H | 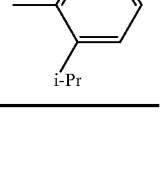 i-Pr |
| 122 | t-Bu | EtO | EtO | 1 | H | H | H | i-Pr |
| 123 | t-Bu | i-PrO | i-PrO | 1 | H | H | H |  i-Pr |

The pyrimidine derivative (1) of the present invention or a salt thereof, after being processed together with a pharmaceutically acceptable carrier according to a customary method, may be formed into various peroral or parenteral pharmaceutical compositions of a solid type, semi-solid type, or liquid type.

Examples of peroral preparations include tablets, pills, granules, soft and hard capsules, powders, fine granules, emulsions, syrups, pellets, and elixirs. Examples of parenteral preparations include injections, instillations, transfusions, ointments, lotions, tonics, sprays, suspensions, oils, emulsions, and suppositories. In order to prepare a pharmaceutical composition containing the compound of the present invention as the active ingredient, known methods may be used, and there may also be used as required surfactants, excipients, coloring agents, odor improving agents, preservatives, stabilizers, buffers, suspension bases, isotonic agents, etc.

The amount of administration of the pyrimidine derivative (1) or a salt thereof varies in accordance with the identity of the compound, the disease which is to be treated or prevented, the manner of administration, the age and symptoms of the patient, duration of treatment, etc. In the case of parenteral administration, the amount of administration is preferably between 0.01 and 30 mg/kg for subcutaneous, intravenous, intramuscular, or rectal administration. In contrast, in the case of peroral administration, the compound is preferably administered in an amount of 0.01–100 mg/kg, more preferably 0.5–30 mg/kg.

EXAMPLES

The present invention will next be described in more detail by the examples, which should not be construed as limiting the invention thereto.

Example 1 (Synthesis of Compound No. 1)

Metallic sodium (160 mg) was added to ethyl glycolate (5 g) and the mixture was stirred for 30 minutes at room temperature. To the resultant transparent solution was added 4-t-butyl-N-[6-chloro-5-(2-methoxyphenoxy)-2-(2-pyrimidinyl)-4-pyrimidinyl]benzenesulfonamide (993 mg), and the mixture was stirred for 5 hours at 95° C. Ethyl acetate was added to the reaction mixture, followed by successive washing with 1N-HCl, water, and saturated brine.

The organic layer was dried over anhydrous sodium sulfate. The solvent was evaporated under reduced pressure. The residue was purified by silica gel column chromatography (chloroform-methanol 30:1), to give 732 mg of ethyl [6-(4-t-butylphenylsulfonylamino)-5-(2-methoxyphenoxy)-2-(2-pyrimidinyl)-4-pyrimidinyloxy]acetate as a pale yellow oil.

$^1$H-NMR(CDCl$_3$, ppm, TMS) : 1.22(3H, t, J=7.1 Hz), 1.29(9H, s), 4.01(3H, s), 4.18(2H, q, J=7.1 Hz), 5.10(2H, s), 6.89(1H, brt, J=7.8 Hz), 7.00(1H, brd, J=7.8 Hz), 7.12(1H, brt, J=7.8 Hz), 7.33(1H, brd, J=7.8 Hz), 7.40(1H, t, J=4.6 Hz), 7.41(2H, d, J=8.8 Hz), 8.34(2H, m), 8.97(2H, d, J=4.6 Hz); IR(KBr)cm$^{-1}$: 2965, 1755, 1620, 1580, 1560, 1500, 1345, 1255, 1175, 1085, 750

Example 2 (Synthesis of Compound No. 2)

1N-NaOH (10 ml) was added to a solution of Compound No. 1(625 mg) in ethanol (20 ml). The mixture was stirred overnight at room temperature, then solvent was evaporated under reduced pressure. 1N-HCl (10 ml) was added, and the mixture was extracted with chloroform (20 ml), followed by washing successively with water and saturated brine. Drying over anhydrous sodium sulfate and concentrating under reduced pressure gave 586 mg of [6-(4-t-butylphenylsulfonylamino)-5-(2-methoxyphenoxy)-2-(2-pyrimidinyl)-4-pyrimidinyloxy]acetic acid as a pale yellow powder.

$^1$H-NMR(CDCl$_3$, ppm, TMS): 1.26(9H, s), 4.02(3H, s), 5.40(2H, s), 6.92(1H, dt, J=7.9, 1.5 Hz), 7.02(1H, dd, J=7.9, 1.5 Hz), 7.14(1H, dt, J=7.9, 1.5 Hz), 7.34(1H, dd, J=7.9, 1.5 Hz), 7.39(2H, d, J=8.5 Hz), 7.43(1H, t, J=4.9 Hz), 8.44(2H, d, J=8.5 Hz), 9.14(2H, d, J=4.9 Hz)

Example 3 (Synthesis of Compound No. 3)

To a solution of 4-t-butyl-N-[6-(3-hydroxypropyloxy)-5-(2-methoxyphenoxy)-2-(2-pyrimidinyl)-4-pyrimidinyl]benzene sulfonamide (3.2 g) in dimethylformamide (50 ml) was added pyridinium dichromate (31.9 g). The mixture was stirred for 12 hours at room temperature, and subsequently supplemented with pyridinium dichromate (10.6 g), followed by stirring for 12 hours. Ethyl acetate was added, and the mixture was washed with 1N-HCl and then with water. The organic layer was extracted with sat. aq. NaHCO$_3$, and the aqueous layer was washed with ethyl acetate. The aqueous layer was acidified with dilute HCL, and then extracted with ethyl acetate. The organic layer was washed with saturated brine. Drying over anhydrous magnesium sulfate and concentrating under reduced pressure gave 1.85 g of 3-[6-(4-t-butylphenylsulfonylamino)-5-(2-methoxyphenoxy)-2-(2-pyrimidinyl)-4-pyrimidinyloxy]propionic acid as a pale yellow powder.

$^1$H-NMR(CDCl$_3$-CD$_3$OD(4:1), ppm, TMS) 1.29(9H, s), 2.64(2H, t, J=6.2 Hz), 3.91(3H, s), 4.75(2H, t, J=6.2 Hz), 6.84(1H, dt, J=7.9, 1.5 Hz), 6.96(1H, brd, J=7.9 Hz), 6.98 (1H, dd, J=7.9, 1.5 Hz), 7.09(1H, dt, J=7.9, 1.5 Hz), 7.43 (2H, d, J=8.8 Hz), 7.50(1H, t, J=4.9 Hz), 8.31(2H, m), 9.02(2H, d, J=4.9 Hz); IR(KBr)cm$^{-1}$: 3400, 2965, 1730, 1620, 1580, 1560, 1500, 1340, 1255, 1175, 1080, 750

Example 4 (Synthesis of Compound No. 4)

The procedure described in Example 3 was repeated using 4-t-butyl-N-[6-(4-hydroxybutyloxy)-5-(2-methoxyphenoxy)-2-(2-pyrimidinyl)-4-pyrimidinyl]benzenesulfonamide, to obtain 4-[6-(4-t-butylphenylsulfonylamino)-5-(2-methoxyphenoxy)-2-(2-pyrimidinyl)-4-pyrimidinyloxy]butyric acid as a pale yellow powder.

$^1$H-NMR(CDCl$_3$, ppm, TMS): 1.29(9H, s), 1.95(2H, m), 2.25(2H, t, J=7.2 Hz), 3.90(3H, s), 4.52(2H, t, J=6.1 Hz), 6.84(1H, dt, J=7.7, 1.5 Hz), 6.96(1H, dd, J=7.7, 1.5 Hz), 6.97(1H, dd, J=7.7, 1.5 Hz) 7.09(1H, dt, J=7.7, 1.5 Hz), 7.42(2H, d, J=8.6 Hz) 7.45(1H, t, J=4.9 Hz), 8.34(2H, m), 9.06(2H, d, J=4.9 Hz); IR(KBr)cm$^{-1}$: 3305, 29 65, 1735, 1685, 1615, 1565, 1500, 1335, 1260, 1165, 1115, 1075, 750

Example 5 (Synthesis of Compound No. 5)

The procedure described in Example 3 was repeated using 4-t-butyl-N-[6-(5-hydroxypentyloxy)-5-(2-methoxyphenoxy )-2-(2-pyrimidinyl )-4-pyrimidinyl]benzenesulfonamide, to obtain 5-[6-(4-t-butylphenylsulfonylamino)-5-(2-methoxyphenox)-2-(2-pyrimidinyl)-4-pyrimidinyloxy]pentanoic acid as a of yellow powder.

$^1$H-NMR(CDCl$_3$, ppm, TMS): 1.29(9H, s) 1.57(2H, m), 1.70(2H, m), 2.29(2H, t, J=7.3 z), 3.9(3H, s), 4.49(2H, t, J=6.2 Hz), 6.83(1H, dt, J=7.8, 1.5 Hz), 6.95(1H, dd, J=7.8 1.5 Hz), 7.00(1H, brd, J=7.8 Hz), 7.08(1H, dt, J=7.8, 1.5 Hz), 7.43(2H, d, J=8.6 Hz), 7.46(1H, t, J=4.9 Hz), 8.33(2H, brd, J=8.6 Hz), 9.08(2H, d, J=4.9 Hz)

Example 6 (Synthesis of Compound No. 6)

Concentrated sulfuric acid (2 droplets) was added to a solution of Compound No. 5(41.3 mg) in isopropyl alcohol (2 ml). The mixture was stirred overnight at room temperature, then solvent was evaporated under reduced pressure. The residue was dissolved in ethyl acetate, and the mixture was washed successively with sat. ag. NaHCO$_3$, water, 1N-HCl, and saturated brine. Drying over anhydrous sodium sulfate and concentrating under reduced pressure gave 34.9 mg of isopropyl 5-[6-(4-t-butylphenylsulfonylamino)-5-(2-methoxyphenoxy)-2-(2-pyrimidinyl)-4-pyrimidinyloxy]pentanoate as a pale yellow oil.

$^1$H-NMR(CDCl$_3$, ppm, TMS): 1.19(6H, d, J=6.1 Hz), 1.29(9H, s), 1.53(2H, m), 1.66(2H, m), 2.19(2H, t, J=7.3 Hz), 3.91(3H, s), 4.48(2H, t, J=6.1 Hz), 4.97(1H, sep, J=6.1 Hz), 6.83(1H, dt, J=7.8, 1.5 Hz), 6.96(1H, dd, J=7.8, 1.5 Hz), 6.98(1H, brd, J=7.8 Hz), 7.08(1H, dt, J=7.8, 1.5 Hz), 7.42(1H, t, J=4.9 Hz), 7.42(2H, d, J=8.6 Hz), 8.32(2H, m), 9.02(2H, d, J=4.9 Hz) IR(KBr)cm$^{-1}$: 2965, 1725, 1620, 1580, 1560, 1500, 1340, 1255, 1170, 1080, 750

Example 7 (Synthesis of Compound No. 7)

The procedure described in Example 6 was repeated using Compound No. 3 and benzyl alcohol, to obtain benzyl 3-[6-(4-t-butylphenylsulfonylamino)-5-(2-methoxyphenoxy)-2-(2-pyrimidinyl)-4-pyrimidinyloxy]propionate as a pale yellow oil.

$^1$H-NMR(CDCl$_3$, ppm, TMS): 1.29(9H, s), 2.72(2H, t, J=6.1 Hz), 3.90(3H, s), 4.80(2H, t, J=6.1 Hz), 5.03(2H, s), 6.79(1H, dt, J=7.7, 1.5 Hz), 6.93(1H, dd, J=7.7, 1.5 Hz), 6.99(1H, brd, J=7.7 Hz), 7.06(1H, dt, J=7.7, 1.5 Hz), 7.28 (5H, m), 7.41(1H, t, J=4.9 Hz), 7.42(2H, d, J=8.6 Hz), 8.35(2H, m), 9.00(2H, d, J=4.9 Hz)

Example 8 (Synthesis of Compound No. 8)

The procedure described in Example 6 was repeated using Compound No. 3 and n-hexyl alcohol, to obtain n-hexyl 3-[6-(4-t-butylphenylsulfonylamino)-5-(2-methoxyphenoxy)-2-(2-pyrimidinyl)-4-pyrimidinyloxy]propionate as a pale yellow oil.

$^1$H-NMR(CDCl$_3$, ppm, TMS): 0.85(3H, t, J=6.8 Hz), 1.25(6H, m), 1.29(9H, s), 1.54(2H, m), 2.68(2H, t, J=6.2 Hz), 3.93(3H, s), 4.00(2H, t, J=6.7 Hz), 4.78(2H, t, J=6.2 Hz), 6.78~7.18(4H, m), 7.41(2H, d, J=8.6 Hz), 7.42(1H, t, J=4.9 Hz), 8.34(2H, m), 9.01(2H, d, J=4.9 Hz)

Example 9 (Synthesis of Compound No. 9)

The procedure described in Example 6 was repeated using Compound No. 3 and ethanol, to obtain ethyl 3-[6-(4-t-butylphenylsulfonylamino)-5-(2-methoxyphenoxy)-2-(2-pyrimidinyl)-4-pyrimidinyloxy]propionate as a pale yellow oil.

$^1$H-NMR(CDCl$_3$, ppm, TMS): 1.18(3H, t, J=7.2 Hz), 1.29(9H, s), 2.67(2H, t, J=6.2 Hz), 3.94(3H, s), 4.06(2H, q, J=7.2 Hz), 4.78(2H, t, J=6.2 Hz), 6.77~7.18(4H, m), 7.42 (2H, d, J=8.5 Hz), 7.42(1H, t, J=4.9 Hz), 8.35(2H, m), 9.00(2H, d, J=4.9 Hz)

Example 10 (Synthesis of Compound No. 10)

The procedure described in Example 6 was repeated using Compound No. 2 and benzyl alcohol, to obtain benzyl

[6-(4-t-butylphenylsulfonylamino)-5-(2-methoxyphenoxy)-2-(2-pyrimidinyl)-4-pyrimidinyloxy]acetate as a pale yellow oil.

$^1$H-NMR(CDCl$_3$, ppm, TMS): 1.29(9H, s) 3.98(3H, s), 5.15(2H, s), 5.17(2H, s), 6.78(1H, dt, J=7.7, 1.5 Hz), 6.98 (1H, dd, J=7.7, 1.5 Hz), 7.09(1H, dt, J=7.7, 1.5 Hz), 7.24 (6H, m), 7.41(1H, t, J=4.9 Hz), 7.42(2H, d, J=8.5 Hz), 8.35(2H, m), 8.98(2H, d, J=4.9 Hz) IR(KBr)cm$^{-1}$: 2965, 1755, 1620, 1580, 1560, 1500, 1345, 1255, 1175, 1085, 750

Example 11 (Synthesis of Compound No. 11)

The procedure described in Example 6 was repeated using Compound No. 4 and 4-methoxybenzyl alcohol, to obtain 4-methoxybenzyl 4-[6-(4-t-butylphenylsulfonylamino)-5-(2-methoxyphenoxy)-2-(2-pyrimidinyl)-4-pyrimidinyloxy] butyrate as a pale yellow oil.

$^1$H-NMR(CDCl$_3$, ppm, TMS): 1.29(9H, s), 1.93(2H, m), 2.17(2H, t, J=7.6 Hz), 3.80(3H, s), 3.85(3H, s), 4.48(2H, t, J=6.0 Hz), 5.00(2H, s), 6.77(1H, dt, J=7.7, 1.5 Hz), 6.87(2H, d, J=7~8.5 Hz), 6.83~6.97(2H, m), 7.02(1H, dt, J=7.7, 1.5 Hz), 7.26(2H, d, J=8.5 Hz), 7.42(1H, t, J=4.9 Hz), 7.42(2H, d, J=8.5 Hz), 8.35(2H, m), 9.01(2H, d, J=4.9 Hz) IR(KBr) cm$^{-1}$: 2965, 1730, 1615, 1580, 1560, 1500, 1340, 1250, 1170, 1080, 750

Example 12 (Synthesis of Compound No. 12)

To a solution of Compound No. 2(40 mg) in methylenechloride-dimethylformamide (3:1, 2 ml) were added 3-chlorophenol (45 ml), N,N-dimethylaminopyridine (1 mg), and 1-(3-dimethylaminopropyl)-3-ethylcarbodiimide.HCl (16.3 mg), and the mixture was stirred overnight at room temperature. Solvent was evaporated under reduced pressure, and the residue was dissolved in ethyl acetate. The solution was successively washed with sat. aq. NaHCO$_3$, water, 1N-HCl, and saturated brine. The residue resulting from drying over anhydrous sodium sulfate and concentrating under reduced pressure was purified by preparative thin-layer chromatography (by Merck; eluent: chloroform-methanol (10:1)). The purified material was dissolved in ethyl acetate, and the solution was washed with 1N-HCl and saturated brine, then brought to dryness over anhydrous sodium sulfate. When the solvent was evaporated under reduced pressure, there was obtained 3-chlorophenyl [6-(4-t-butylphenylsulfonylamino)-5-(2-methoxyphenoxy)-2-(2-pyrimidinyl)-4-pyrimidinyloxy]acetate as a pale yellow oil.

$^1$H-NMR(CDCl$_3$, ppm, TMS): 1.29(9H, s), 3.98(3H, s), 5.26(2H, s), 6.84(1H, dt, J=7.8, 1.5 Hz), 6.95~7.04(2H, m), 7.10(1H, d, J=7.8, 1.5 Hz), 7.15~7.30(4H, m), 7.43(2H, d, J=8.6 Hz), 7.45(1H, t, J=4.9 Hz), 8.36(2H, m), 9.03(2H, d, J=4.9 Hz) IR(KBr)cm$^{-1}$: 2965, 1780, 1620, 1580, 1560, 1500, 1340, 1255, 1175, 1085, 750

Example 13 (Synthesis of Compound No. 13)

To a solution of Compound No. 3(21.8 mg) in dimethylformamide (0.5 ml) were added N-hydroxybenzotriazole ammonium salt (6.4 mg) and 1-(3-dimethylaminopropyl)-3-ethylcarbodiimide.HCl (8.0 mg), and the mixture was stirred for 2.5 hours at room temperature. Ethyl acetate (10 ml) was added to the reaction mixture, followed by washing successively with 1N-HCl, water, sat. aq. NaHCO$_3$, water, and saturated brine, and drying over anhydrous sodium sulfate. Solvent was evaporated under reduced pressure, and the residue was purified by preparative thin-layer chromatography (eluent:chloroform-methanol (5:1)). The purified material was dissolved in ethyl acetate, and the resultant solution was washed with 1N-HCl and saturated brine, then brought to dryness over anhydrous sodium sulfate. When the solvent was evaporated under reduced pressure, there was obtained 3-[6-(4-t-butylphenylsulfonylamino)-5-(2-methoxyphenoxy)-2-(2-pyrimidinyl)-4-pyrimidinyloxy] propionamide (5.8 mg) as a pale yellow oil.

$^1$H-NMR(CDCl$_3$, ppm, TMS): 1.29(9H, s), 2.60(2H, t, J=6.5 Hz), 3.93(3H, s), 4.76(2H, t, J=6.5 Hz), 6.80~7.17(4H, m), 7.44(2H, d, J=8.8 Hz), 7.48(1H, t, J=4.9 Hz), 8.36(2H, m), 9.01(2H, d, J=4.9 Hz)

Example 14 (Synthesis of Compound No. 14)

To a solution of Compound No. 3(100 mg) in 1:1 dimethylformamide-methylene chloride (8 ml) were added N-hydroxybenzotriazole.H$_2$O (53.8 mg), benzylamine (95.9 mg), and 1-(3-dimethylaminopropyl)-3-ethylcarbodiimide.HCl (40 mg), and the mixture was stirred overnight at room temperature. Solvent was evaporated under reduced pressure, and the residue was dissolved in ethyl acetate (20 ml). The resultant solution was successively washed with sat. aq. NaHCO3, water, 1N-HCl, and saturated brine, and dried over anhydrous sodium sulfate. When the residue was concentrated under reduced pressure, there was obtained N-benzyl-3-[6-(4-t-butylphenylsulfonylamino)-5-(2-methoxyphenoxy)-2-(2-pyrimidinyl)-4-pyrimidinyloxy]-propionamide (100.9 mg) as a oil.

$^1$H-NMR(CDCl$_3$, ppm, TMS): 1.29(9H, s), 2.67(2H, t, J=6.5 Hz), 3.90(3H, s), 4.39(2H, d, J=5.9 Hz), 4.82(2H, t, J=6.5 Hz), 6.75(1H, m), 6.81(1H, dt, J=7.8, 1.5 Hz), 6.94 (1H, dd, J=7.8, 1.5 Hz), 6.97(1H, brd, J=7.8 Hz), 7.08(1H, dt, J=7.8, 1.5 Hz), 7.14~7.25(5H, m), 7.36(1H, t, J=4.9 Hz), 7.42(2H, d, J=8.6 Hz), 8.35(2H, m), 8.87(2H, d, J=4.9 Hz)

Example 15 (Synthesis of Compound No. 15)

The procedure described in Example 14 was repeated using Compound No. 2 and benzylamine, to obtain N-benzyl-[6-(4-t-butylphenylsulfonylamino)-5-(2-methoxyphenoxy)-2-(2-pyrimidinyl)-4-pyrimidinyloxy] acetamide as a pale yellow powder.

$^1$H-NMR(CDCl$_3$, ppm, TMS): 1.29(9H, s), 3.68(3H, s), 4.29(2H, d, J=6.1 Hz), 5.02(2H, s), 6.20(1H, m), 6.69(1H, dt, J=7.8, 1.5 Hz), 6.78(1H, dd, J=7.8, 1.5 Hz), 6.90(1H, brd, J=7.8 Hz), 6.97(1H, dt, J=7.8, 1.5 Hz), 7.05~7.33(5H, m), 7.43(1H, t, J=4.9 Hz), 7.44(2H, d, J=8.5 Hz), 8.38(2H, m), 8.98(2H, d, J=4.9 Hz)

Example 16 (Synthesis of Compound No. 16)

The procedure described in Example 14 was repeated using Compound No. 4 and benzylamine, to obtain N-benzyl-4-[6-(4-t-butylphenylsulfonylamino)-5-(2-methoxyphenoxy)-2-(2-pyrimidinyl)-4-pyrimidinyloxy] butyramide as a pale yellow powder.

$^1$H-NMR(CDCl$_3$, ppm, TMS): 1.29(9H, s), 2.01(4H, m), 3.82(3H, s), 4.35(2H, d, J=5.6 Hz), 4.49(2H, m), 5.85(1H, m), 6.74(1H, dt, J=7.7, 1.5 Hz) 6.81~6.90(2H, m), 6.96(1H, dt, J=7.7, 1.5 Hz), 7.16~7.32(5H, m), 7.40(1H, t, J=4.9 Hz), 7.43(2H, d, J=8.5 Hz), 8.35(2H, m), 8.96(2H, d, J=4.9 Hz)

Example 17 (Synthesis of Compound No. 19)

The procedure described in Example 14 was repeated using Compound No. 5 and benzylamine, to obtain N-benzyl-5-[6-(4-t-butylphenylsulfonylamino)-5-(2-methoxyphenoxy)-2-(2-pyrimidinyl)-4-pyrimidinyloxy] pentanamide as a pale yellow powder.

¹H-NMR(CDCl₃, ppm, TMS): 1.29(9H, s), 1.52~1.76 (4H, m), 2.22(2H, t, J=7.0 Hz), 3.89(3H, s), 4.35(2H, d, J=5.9 Hz), 4.53(2H, t, J=5.9 Hz), 6.36(1H, m), 6.79(1H, t, J=7.6 Hz), 6.88~6.98(2H, m), 7.04(1H, t, J=7.7 Hz), 7.12~7.29(5H, m), 7.37(1H, t, J=4.6 Hz), 7.43(2H, d, J=8.6 Hz), 8.36(2H, m), 8.92(2H, d, J=4.6 Hz) IR(KBr)cm⁻¹: 2965, 1650, 1620, 1580, 1560, 1500, 1340.1255, 1175, 1080, 750

Example 18 (Synthesis of Compound No. 24)

The procedure described in Example 14 was repeated using Compound No. 2 and phenethylamine, to obtain N-phenethyl-[6-(4-t-butylphenylsulfonylamino)-5-(2-methoxyphenoxy)-2-(2-pyrimidinyl)-4-pyrimidinyloxy] acetamide as a pale yellow oil.

¹H-NMR(CDCl₃, ppm, TMS): 1.29(9H, s), 2.65(2H, t, J=7.1 Hz), 3.32(2H, m), 3.81(3H, s), 4.96(2H, s), 5.98(1H, m), 6.75(1H, dt, J=7.8, 1.5 Hz), 6.79(1H, dd, J=7.8.1.5 Hz), 6.93(1H, dd, J=7.8.1.5 Hz), 7.01~7.20(6H, m), 7.45(1H, t, J=4.9 Hz), 7.45(2H, d, J=8.6 Hz), 8.37(2H, m), 9.01(2H, d, J=4.9 Hz)

Example 19 (Synthesis of Compound No. 25)

The procedure described in Example 14 was repeated using Compound No. 4 and aniline, to obtain N-phenyl-4-[6-(4-t-butylphenylsulfonylamino)-5-(2-methoxyphenoxy)-2-(2-pyrimidinyl)-4-pyrimidinyloxy]butyramide as a pale yellow powder.

¹H-NMR(CDCl₃, ppm, TMS): 1.29(9H, s), 2.06(2H, m), 2.20(2H, m), 3.90(3H, s), 4.53(2H, t, J=5.6 Hz), 6.80~7.31 (6H, m), 7.34~7.48(5H, m) 7.63(1H, m), 8.37(2H, m), 8.94(2H, d, J=4.9 Hz); IR(KBr)cm⁻¹: 2965, 1670, 1620, 1580, 1560, 1500, 1340, 1255, 1175, 1080, 775

Example 20 (Synthesis of Compound No. 29)

The procedure described in Example 14 was repeated using Compound No. 4 and 2-methoxyaniline, to obtain N-(2-methoxyphenyl)-4-[6-(4-t-butylphenylsulfonylamino)-5-(2-methoxyphenoxy)-2-(2-pyrimidinyl)-4-pyrimidinyloxy]butyramide as a pale yellow powder.

¹H-NMR(CDCl₃, ppm, TMS): 1.29(9H, s), 2.04(2H, m), 2.13(2H, m), 3.85(3H, s), 3.88(3H, s), 4.55(2H, t, J=5.6 Hz), 6.81~7.01(6H, m), 7.02(1H, dt, J=7.7, 1.5 Hz), 7.11(1H, dt, J=7.7, 1.5 Hz), 7.41(1H, t, J=4.9 Hz), 7.43(2H, d, J=8.8 Hz), 8.31(2H, m), 8.99(2H, d, J=4.9 Hz)

Example 21 (Synthesis of Compound No. 30)

The procedure described in Example 14 was repeated using Compound No. 4 and 3-chloroaniline, to obtain N-(3-chlorophenyl)-4-[6-(4-t-butylphenylsulfonylamino)-5-(2-methoxyphenoxy)-2-(2-pyrimidinyl)-4-pyrimidinyloxy]butyramide as a colorless powder.

¹H-NMR(CDCl₃, ppm, TMS): 1.29(9H, s), 2.06(2H, m), 2.23(2H, t, J=7.1 Hz), 3.90(3H, s), 4.55(2H, t, J=5.6 Hz), 6.86(1H, dt, J=7.8, 1.5 Hz), 6.95(1H, dd, J=7.8, 1.5 Hz), 6.98(1H, dd, J=7.8, 1.5 Hz), 7.04(1H, m), 7.11(1H, dt, J=7.8, 1.5 Hz), 7.17(1H, t, J=8.1 Hz), 7.28(1H, m), 7.41(1H, t, J=4.9 Hz), 7.43(2H, d, J=8.8 Hz), 7.55(1H, brs), 8.33(2H, m), 8.95(2H, d, J=4.9 Hz)

Example 22 (Synthesis of Compound No. 31)

The procedure described in Example 14 was repeated using Compound No. 2 and 2-methoxyaniline, to obtain N-(2-methoxyphenyl)-[6-(4-t-butylphenylsulfonylamino)-5-(2-methoxyphenoxy)-2-(2-pyrimidinyl)-4-pyrimidinyloxy]acetamide as a colorless powder.

¹H-NMR(CDCl₃, ppm, TMS): 1.29(9H, s), 3.58(3H, s), 3.99(3H, s), 5.20(2H, s), 7.30~7.67(7H, m), 7.36~7.48(3H, m), 8.26(1H, dd, J=8.1, 1.5 Hz), 8.37(2H, m), 8.69(1H, brs), 9.00(2H, d, J=4.6 Hz); IR(KBr)cm⁻¹: 2965, 1695, 1620, 1580, 1560, 1500, 1340, 1255, 1175, 1085, 750

Example 23 (Synthesis of Compound No. 32)

The procedure described in Example 14 was repeated using Compound No. 2 and 3-chloroaniline, to obtain N-(3-chlorophenyl)-[6-(4-t-butylphenylsulfonylamino)-5-(2-methoxyphenoxy)-2-(2-pyrimidinyl)-4-pyrimidinyloxy] acetamide as a colorless powder.

¹H-NMR(CDCl₃, ppm, TMS): 1.29(9H, s), 3.90(3H, s), 5.09(2H, s), 6.88(1H, dt, J=7.7, 1.5 Hz), 6.95~7.10(3H, m), 7.14(1H, dt, J=7.7, 1.5 Hz), 7.19(1H, t, J=7.9 Hz), 7.32(1H, t, J=1.8 Hz), 7.37(2H, m), 7.44(2H, d, J=8.8 Hz), 7.48(1H, t, J=4.9 Hz), 8.35(2H, m), 9.04(2H, d, J=4.9 Hz)

Example 24 (Synthesis of Compound No. 35)

The procedure described in Example 14 was repeated using Compound No. 2 and aniline, to obtain N-phenyl-[6-(4-t-butylphenylsulfonylamino)-5-(2-methoxyphenoxy)-2-(2-pyrimidinyl)-4-pyrimidinyloxy]acetamide as a pale yellow oil.

¹H-NMR(CDCl₃, ppm, TMS): 1.29(9H, s), 3.86(3H, s), 5.11(2H, s), 6.85(1H, dt, J=7.7, 1.5 Hz), 6.98(1H, dd, J=7.7, 1.5 Hz), 7.01(1H, brd, J=7.7 Hz), 7.05~7.14(2H, m), 7.22~7.38(4H, m), 7.43(2H, d, J=8.5 Hz), 7.45(1H, t, J=4.9 Hz), 8.38(2H, m), 9.01(2H, d, J=4.9 Hz); IR(KBr)cm⁻¹: 2965, 1700, 1620, 1580, 1560, 1500, 1340, 1255, 1175, 1085, 775

Example 25 (Synthesis of Compound No. 36)

The procedure described in Example 14 was repeated using Compound No. 2 and 1-naphthalenemethylamine, to obtain N-(1-naphthylmethyl)-[6-(4-t-butylphenylsulfonylamino)-5-(2-methoxyphenoxy)-2-(2-pyrimidinyl)-4-pyrimidinyloxy]acetamide as a pale yellow oil.

¹H-NMR(CDCl₃, ppm, TMS): 1.29(9H, s), 3.58(3H, s), 4.78(2H, d, J=5.6 Hz), 5.05(2H, s), 6.30(1H, m), 6.42(1H, dt, J=7.8, 1.5 Hz), 6.56(1H, dd, J=7.8, 1.5 Hz), 6.72(2H, m), 7.26(1H, m), 7.35~7.50(6H, m), 7.78~7.88(3H, m), 8.34 (2H, m), 8.94(2H, d, J=4.9 Hz) IR(KBr)cm⁻¹: 2965, 1675, 1620, 1580, 1560, 1500, 1340, 1255, 1175, 1085, 750

Example 26 (Synthesis of Compound No. 37)

The procedure described in Example 14 was repeated using Compound No. 4 and 3-methoxybenzylamine, to obtain N-(3-methoxybenzyl)-4-[6-(4-t-butylphenylsulfonylamino)-5-(2-methoxyphenoxy)-2-(2-pyrimidinyl)-4-pyrimidinyloxy]butyramide as a pale yellow oil.

¹H-NMR(CDCl₃, ppm, TMS): 1.29(9H, s), 2.01(4H, m), 3.74(3H, s), 3.83(3H, s), 4.33(2H, d, J=5.6 Hz), 4.49(2H, m), 5.88(1H, m), 6.70~6.81(5H, m), 6.87(1H, dd, J=7.8, 1.5 Hz), 6.98(1H, dt, J=7.8, 1.5 Hz), 7.18(1H, dt, J=7.8, 1.5 Hz), 7.41(1H, t, J=4.9 Hz), 7.43(2H, d, J=8.8 Hz), 8.33(2H, m), 8.94(2H, d, J=4.9 Hz); IR(KBr)cm⁻¹: 2965.1655, 1615, 1580, 1560, 1500, 1340, 1260, 1170, 1080, 750

Example 27 (Synthesis of Compound No. 38)

The procedure described in Example 14 was repeated using Compound No. 4 and 2-chlorophenethylamine, to obtain N-(2-chlorophenethyl)-4-[6-(4-t-butylphenylsulfonylamino)-5-(2-methoxyphenoxy)-2-(2-pyrimidinyl)-4-pyrimidinyloxy]butylamide as a pale yellow oil.

$^1$H-NMR(CDCl$_3$, ppm, TMS): 1.29(9H, s), 1.95(4H, m), 2.90(2H, t, J=7.0 Hz), 3.46(2H, m), 3.87(3H, s), 4.45(2H, m) 5.62(1H, m) 6.76(2H, dt, J=7.8. 1.5 Hz), 6.87(1H, dd, J=7.8, 1.5 Hz), 6.91(1H, dd, J=7.8, 1.5 Hz), 6.99(1H, dt, J=7.8, 1.5 Hz), 7.05~7.19(3H, m), 7.30(1H, m), 7.43(1H, t, J=4.9 Hz), 7.43(2H, d, J=8.8 Hz), 8.33(2H, m), 9.00(2H, d, J=4.9 Hz) IR(KBr)cm$^{-1}$: 2965, 1655, 1620, 1580, 1560, 1500, 1340, 1255, 1175, 1080, 775

Example 28 (Synthesis of Compound No. 40)

The procedure described in Example 14 was repeated using Compound No. 5 and 2-methoxybenzylamine, to obtain N-(2-methoxybenzyl)-5-[6-(4-t-butylphenylsulfonylamino)-5-(2-methoxyphenoxy)-2-(2-pyrimidinyl)-4-pyrimidinyloxy]pentanamide as a pale yellow oil.

$^1$H-NMR(CDCl$_3$, ppm, TMS): 1.29(9H, s), 1.56(2H, m), 1.65(2H, m,), 2.15(2H, t, J=7.2 Hz), 3.75(3H, s), 3.88(3H, s), 4.38(2H, d, J=5.6 Hz), 4.50(2H, t, J=6.1 Hz), 6.30(1H, m), 6.73~6.97(5H, m), 7.03(5H, dt, J=7.8 1.5 Hz), 7.15~7.24 (2H, m), 7.39(1H, t, J=4.9 Hz), 7.43(2H, d, J=8.6 Hz), 8.32(2H, m), 8.96(2H, d, J=4.9 Hz); IR(KBr)cm$^{-1}$: 2960, 1650, 1620, 1580, 1560, 1500.1340, 1245, 1175, 1080, 775

Example 29 (Synthesis of Compound No. 41)

The procedure described in Example 14 was repeated using Compound No. 5 and 3-chlorobenzylamine, to obtain N-(3-chlorobenzyl)-5-[6-(4-t-butylphenylsulfonylamino)-5-(2-methoxyphenoxy)-2-(2-pyrimidinyl)- 4-pyrimidinyloxy] pentanamide as a pale yellow oil.

$^1$H-NMR(CDCl$_3$, ppm, TMS): 1.29(9H, s), 1.69(4H, m), 2.24(2H, t, J=6.6 Hz) 3.90(3H, s), 4.32(2H, d, J=5.9 Hz), 4.54(2H, t, J=6.0 Hz), 6.51(1H, m), 6.80(1H, brt, J=8.3 Hz), 6.94(2H, m), 7.00~7.20(5H, m), 7.39(1H, t, J=4.9 Hz), 7.43(2H, d, J=8.8 Hz), 8.32(2H, m), 8.93(2H, d, J=4.9 Hz)

Example 30 (Synthesis of Compound No. 51)

The procedure described in Example 14 was repeated using Compound No. 3 and 2-methylbenzylamine, to obtain N-(2-methylbenzyl)-3-[6-(4-t-butylphenylsulfonylamino)-5-(2-methoxyphenoxy)-2-(2-pyrimidinyl)-4-pyrimidinyloxy]propionamide as a pale yellow oil.

$^1$H-NMR(CDCl$_3$, ppm, TMS): 1.29(9H, s), 2.24(3H, s), 2.67(2H, t, J=6.4 Hz), 3.90(3H, s), 4.37(2H, d, J=5.6 Hz), 4.82(2H, t, J=6.4 Hz), 6.52(1H, m), 6.80(1H, t, J=7.8 Hz), 6.94(1H, d, J=7.8 Hz), 6.96~7.18(6H, m), 7.34(1H, t, J=4.9 Hz), 7.42(2H, d, J=8.7 Hz), 8.37(2H, m), 8.82(2H, d, J=4.9 Hz) IR(KBr)cm$^{-1}$: 2965, 1655, 1620, 1580, 1560, 1500, 1340, 1255, 1175, 1080, 750

Example 31 (Synthesis of Compound No. 52)

The procedure described in Example 14 was repeated using Compound No. 4 and phenethylamine, to obtain N-phenethyl-4-[6-(4-t-butylphenylsulfonylamino)-5-(2-methoxyphenoxy)-2-(2-pyrimidinyl)-4-pyrimidinyloxy] butyramide as a pale yellow oil.

$^1$H-NMR(CDCl$_3$, ppm, TMS): 1.29(9H, s), 1.91(4H, m), 2.75(2H, t, J=6.5 Hz), 346(2H, m), 3.86(3H, s), 4.43(2H, m), 5.52(1H, m), 6.72(1H, dt, J=7.8, 1.5 Hz), 6.84(1H, d, J=7.8 Hz), 6.88(1H, dd, J=7.8, 1.5 Hz), 6.95(1H, dt, J=7.8, 1.5 Hz), 7.10~7.30(5H, s) 7.42(1H, t, J=4.9 Hz), 7.43(2H, d, J=8.5 Hz), 8.36(2H, m), 8.99(2H, d, J=4.9 Hz); IR(KBr) cm$^{-1}$: 2965, 1655, 1620, 1580, 1560, 1500, 1340, 1255, 1175, 1080, 750

Example 32 (Synthesis of Compound No. 44)

The procedure described in Example 14 was repeated using Compound No. 5 and 2-chlorophenethylamine, to obtain N-(2-chlorophenethyl)-5-[6-(4-t-butylphenylsulfonylamino)-5-(2-methoxyphenoxy)-2-(2-pyrimidinyl)-4-pyrimidinyloxy]pentanamide as a pale yellow oil.

$^1$H-NMR(CDCl$_3$, ppm, TMS): 1.29(9H, s), 1.52~1.70 (4H, m), 2.13(2H, t, J=7.1 Hz), 2.90(2H, t, J=7.0 Hz), 3.48(2H, m), 3.92(3H, s), 4.50(2H, t, J=6.0 Hz), 6.05(1H, m), 6.81(1H, t, J=8.0 Hz), 6.90~7.26(7H, m), 7.42(1H, t, J=4.9 Hz), 7.42(2H, d, J=8.5 Hz), 8.35(2H, m), 8.95(2H, d, J=4.9 Hz) IR(KBr)cm$^{-1}$: 2960, 1650, 1580, 1560, 1500, 1340, 1255, 1170, 1080, Example 33 (Synthesis of Compound No. 46)

The procedure described in Example 14 was repeated using Compound No. 5 and phenethylamine, to obtain N-phenethyl-5-[6-(4-t-butylphenylsulfonylamino)-5-(2-methoxyphenoxy)-2-(2-pyrimidinyl)-4-pyrimidinyloxy] pentanamide as a pale yellow oil.

$^1$H-NMR(CDCl$_3$, ppm, TMS) 1.29(9H, s), 1.52~1.67(4H, m), 2.11(2H, t, J=7.7 Hz), 2.76(2H, t, J=7.0 Hz), 3.45(2H, q, J=6.6 Hz), 3.91(3H, s), 4.49(2H, t, J=6.1 Hz), 5.91(1H, m), 6.80(1H, dt, J=7.0, 1.5H) 6.90~7.26(8H, m), 7.42(2H, d, J=8.6 Hz), 7.43(1H, t, J=4.6 Hz), 8.29~8.40(2H, m), 8.94 (2H, d, J=4.6 Hz) IR(KBr)cm$^{-1}$: 2960.1650, 1580, 1560, 1500, 1340, 1255, 1170, 1080, 750

Example 34 (Synthesis of Compound No. 17)

To a solution of Compound No. 3(51 mg) in 2:1 dimethylformamide-methylene chloride (1.5 ml) were added N-hydroxybenzotriazole.H$_2$O (27 mg), 4-methoxybenzylamine (57.5 μl), and 1-(3-dimethylaminopropyl)-3-ethylcarbodiimide.HCl (17 mg), and the mixture was stirred overnight at room temperature. Solvent was evaporated under reduced pressure, and the residue was dissolved in ethyl acetate (15 ml). The resultant solution was successively washed with 1N-HCl, water, sat. aq. NaHCO$_3$, and saturated brine, and dried over anhydrous sodium sulfate. When the residue was concentrated under reduced pressure, there was obtained a sodium salt of N-(4-methoxybenzyl)-3-[6-(4-t-butylphenylsulfonylamino)-5-(2-methoxyphenoxy)-2-(2-pyrimidinyl)-4-pyrimidinyloxy]propionamide as a colorless powder (38 mg).

Melting point: 129–131° C. IR(KBr)cm$^{-1}$: 2965, 1655, 1615, 1560, 1500, 1380, 1250, 1180, 1135, 1080, 750

Example 35 (Synthesis of Compound No. 18)

The procedure described in Example 34 was repeated using Compound No. 3 and aniline, to obtain a sodium salt of N-phenyl-3-[6-(4-t-butylphenylsulfonylamino)-5-(2-methoxyphenoxy)-2-(2-pyrimidinyl)-4-pyrimidinyloxy] propionamide as a pale yellow powder.

Melting point: 162–163° C. IR(KBr)cm$^{-1}$: 2965, 1670, 1600, 1560, 1500, 1380, 1250, 1135, 1080, 755

Example 36 (Synthesis of Compound No. 20)

The procedure described in Example 34 was repeated using Compound No. 3 and 3,4- methylenedioxybenzylamine, to obtain a sodium salt of N-(3,4-methylenedioxybenzyl)-3-[6-(4-t-butylphenylsulfonylamino)-5-(2-methoxyphenoxy)-2-(2-pyrimidinyl)-4-pyrimidinyloxy]propionamide as a colorless powder.

Melting point: 142–145° C. IR(KBr)cm$^{-1}$: 2965, 1655, 1560, 1500, 1380, 1250, 1180, 1080, 750

Example 37 (Synthesis of Compound No. 21)

The procedure described in Example 34 was repeated using Compound No. 3 and 4-chlorobenzylamine, to obtain a sodium salt of N-(4-chlorobenzyl)-3-[6-(4-t-butylphenylsulfonylamino)-5-(2-methoxyphenoxy)-2-(2-pyrimidinyl)-4-pyrimidinyloxy]propionamide as a colorless powder.

Melting point: 161–163° C. IR(KBr)cm$^{-1}$: 2965, 1655, 1560.1500, 1360, 1250, 1180, 1080, 750

Example 38 (Synthesis of Compound No. 22)

The procedure described in Example 34 was repeated using Compound No. 3 and 2-chlorophenethylamine, to obtain a sodium salt of N-(2-chlorophenethyl)-3-[6-(4-t-butylphenylsulfonylamino)-5-(2-methoxyphenoxy)-2-(2-pyrimidinyl)-4-pyrimidinyloxy]propionamide as a colorless powder.

Melting point: 148–149° C. IR(KBr)cm$^{-1}$: 2965, 1655, 1560, 1500, 1365, 1250, 1180, 1080, 775

Example 39 (Synthesis of Compound No. 23)

The procedure described in Example 34 was repeated using Compound No. 3 and 4-methoxyphenethylamine, to obtain a sodium salt of N-(4-methoxyphenethyl)-3-[6-(4-t-butylphenylsulfonylamino)-5-(2-methoxyphenoxy)-2-(2-pyrimidinyl)-4-pyrimidinyloxy]propionamide as a pale yellow powder.

Melting point: 140–142° C. IR(KBr)cm$^{-1}$: 2965, 1650, 1560, 1500, 1365, 1250, 1180, 1080, 750

Example 40 (Synthesis of Compound No. 26)

The procedure described in Example 34 was repeated using Compound No. 3 and 3-methoxyaniline, to obtain a sodium salt of N-(methoxyphenyl)-3-[6-(4-t-butylphenylsulfonylamino)-5-(2-methoxyphenoxy)-2-(2-pyrimidinyl)-4-pyrimidinyloxy]-propionamide as a colorless powder.

Melting point: 160–161° C. IR(KBr)cm$^{-1}$: 2965.1670, 1600, 1560, 1500, 1380, 1250, 1180, 1080, 750

Example 41 (Synthesis of Compound No. 27)

The procedure described in Example 34 was repeated using Compound No. 3 and phenethylamine, to obtain a sodium salt of N-phenethyl-3-[6-(4-t-butylphenylsulfonylamino)-5-(2-methoxyphenoxy)-2-(2-pyrimidinyl)-4-pyrimidinyloxy]propionamide as a pale yellow powder.

Melting point: 149–150° C. IR(KBr)cm$^{-1}$: 2965, 1655, 1560, 1500, 1365, 1250, 1180, 1080, 750

Example 42 (Synthesis of Compound No. 28)

The procedure described in Example 34 was repeated using Compound No. 3 and 4-chloroaniline, to obtain a sodium salt of N-(4-chlorophenyl)-3-[6-(4-t-butylphenylsulfonylamino)-5-(2-methoxyphenoxy)-2-(2-pyrimidinyl)-4-pyrimidinyloxy]propionamide as a pale yellow powder.

Melting point: 165–168° C. IR(KBr)cm$^{-1}$: 2965, 1675, 1595, 1560, 1500, 1380, 1250, 1180, 1080, 750

Example 43 (Synthesis of Compound No. 33)

The procedure described in Example 34 was repeated using Compound No. 3 and 3,4,5-trimethoxybenzylamine, to obtain a sodium salt of N-(3,4,5-trimethoxybenzyl)-3-[6-(4-t-butylphenylsulfonylamino)-5-(2-methoxyphenoxy)-2-(2-pyrimidinyl)-4-pyrimidinyloxy]propionamide as a pale yellow powder.

Melting point: 142–145° C. IR(KBr)cm$^{-1}$: 2965, 1655, 1590, 1580, 1560, 1500, 1330, 1250, 1180, 1080, 750

Example 44 (Synthesis of Compound No. 34)

The procedure described in Example 34 was repeated using Compound No. 3 and 2-methoxybenzylamine, to obtain a sodium salt of N-(2-methoxybenzyl)-3-[6-(4-t-butylphenylsulfonylamino)-5-(2-methoxyphenoxy)-2-(2-pyrimidinyl)-4-pyrimidinyloxy]propionamide as a colorless powder.

Melting point: 138–139° C. IR(KBr)cm$^{-1}$: 2965, 1655, 1580, 1560, 1500, 1360, 1250, 1175, 1080, 755

Example 45 (Synthesis of Compound No. 42)

The procedure described in Example 34 was repeated using Compound No. 3 and cyclohexylamine, to obtain a sodium salt of N-cyclohexyl-3-[6-(4-t-butylphenylsulfonylamino)-5-(2-methoxyphenoxy)-2-(2-pyrimidinyl)-4-pyrimidinyloxy]-propionamide as a pale yellow powder.

Melting point: 162–164° C. IR(KBr)cm$^{-1}$: 2935, 1650, 1560, 1500, 1365, 1250, 1180, 1080, 750

Example 46 (Synthesis of Compound No. 43)

The procedure described in Example 34 was repeated using Compound No. 3 and n-pentylamine, to obtain a sodium salt of N-(n-pentyl)-3-[6-(4-t-butylphenylsulfonylamino)-5-(2-methoxyphenoxy)-2-(2-pyrimidinyl)-4-pyrimidinyloxy]propionamide as a pale yellow powder.

Melting point: 142–144° C. IR(KBr)cm$^{-1}$: 2960, 1655, 1560, 1365, 1250, 1180, 1080, 750

Example 47 (Synthesis of Compound No. 47)

The procedure described in Example 34 was repeated using Compound No. 5 and 3-phenyl-1-propylamine, to obtain a sodium salt of N-(3-phenyl-1-propyl)-5-[6-(4-t-butylphenylsulfonylamino)-5-(2-methoxyphenoxy)-2-(2-pyrimidinyl)-4-pyrimidinyloxy]pentanamide as a pale yellow powder.

Melting point: 118–120° C.

Example 48 (Synthesis of Compound No. 48)

The procedure described in Example 34 was repeated using Compound No. 3 and 2-methoxyaniline, to obtain a sodium salt of N-(2-methoxyphenyl)-3-[6-(4-t-butylphenylsulfonylamino)-5-(2-methoxyphenoxy)-2-(2-pyrimidinyl)-4-pyrimidinyloxy]propionamide as a pale yellow powder.

Melting point: 120–122° C. IR(KBr)cm$^{-1}$: 2965, 1675, 1600.1560, 1500, 1255, 1135, 1080, 750

The resultant sodium salt was transformed into a free form by a customary method. The NMR data of the free compound are shown below.

$^1$H-NMR(CDCl$_3$, ppm, TMS): 1.29(9H, s), 2.77(2H, t, J=5.9 Hz), 3.74(3H, s), 3.87(3H, s), 4.89(2H, t, J=5.9 Hz), 6.59(1H, t, J=7.2 Hz), 6.77~7.09(6H, m), 7.40(1H, t, J=4.9 Hz), 7.42(2H, d, J=8.5 Hz), 7.90(1H, brs), 8.29(1H, d, J=7.3 Hz), 8.38(2H, d, J=8.5 Hz), 8.82(1H, brs 8.99(2H, d, J=4.9 Hz)

Example 49 (Synthesis of Compound No. 49)

The procedure described in Example 34 was repeated using Compound No. 3, N-methylmorpholine, and an equivalent amount of ethylamine.HCl, to obtain a sodium salt of N-ethyl-3-[6-(4-t-butylphenylsulfonylamino)-5-(2-methoxyphenoxy)-2-(2-pyrimidinyl)-4-pyrimidinyloxy]propionamide as a colorless powder.

Melting point: 117–120° C.

Example 50 (Synthesis of Compound No. 39)

To a solution of Compound No. 2(57.6 mg) in 1:1 dimethylformamide-methylene chloride (2 ml) were added N-hydroxybenzotriazole-H$_2$O (30.6 mg) and 1-(3-dimethylaminopropyl)-3-ethylcarbodiimide.HCl (21.1 mg), and the mixture was stirred for 1 hour. Subsequently, hydroxylamine.HCl (39.8 mg) and triethylamine (0.08 ml) were added, and the mixture was stirred overnight at room temperature. Solvent was evaporated under reduced pressure, and the residue was dissolved in ethyl acetate (5 ml). The resultant solution was successively washed with 1N-HCl, water, sat. aq. NaHCO$_3$, and saturated brine, and dried over anhydrous sodium sulfate. The residue was concentrated under reduced pressure, and subjected to preparative thin-layer chromatography for purification by use of chloroformmethanol (10:1) as an eluent. The purified material was dissolved in ethyl acetate, and the resultant solution was successively washed with 1N HCl and brine, and dried over anhydrous magnesium sulfate. When solvent was evaporated, there was obtained N-hydroxy-[6-(4-t-butylphenylsulfonylamino)-5-(2-methoxyphenoxy)-2-(2-pyrimidinyl)-4-pyrimidinyloxy]acetamide as a colorless powder (12 mg).

$^1$H-NMR(CDCl$_3$, ppm, TMS): 1.29(9H, s), 4.00(3H, s), 5.14(2H, s), 6.89(1H, t, J=7.6 Hz), 7.00(1H, d, J=7.6 Hz), 7.12(1H, t, J=7.6 Hz), 7.32(1H, d, J=7.6 Hz), 7.40(1H, t, J=4.9 Hz), 7.42(2H, d, J=8.3 Hz), 8.37(2H, m), 8.99(2H, d, J=4.9 Hz)

Example 51 (Synthesis of Compound No. 45)

The procedure described in Example 14 was repeated using Compound No. 3 and homopiperidine, to obtain homopiperidino-3-[6-(4-t-butylphenylsulfonylamino)-5-(2-methoxyphenoxy)-2-(2-pyrimidinyl)-4-pyrimidinyloxy]propionamide as a pale yellow oil.

$^1$H-NMR(CDCl$_3$, ppm, TMS): 1.28(9H, s), 1.49(4H, m), 1.64(4H, m), 2.72(2H, t, J=6.7 Hz), 3.36(2H, t, J=6.1 Hz), 3.46(2H, t, J=6.1 Hz), 3.96(3H, s), 4.88(2H, t, J=6.7 Hz), 6.82(1H, t, J=8.1 Hz), 6.92~7.14(3H, m), 7.40(1H, t, J=4.9 Hz), 7.40(2H, d, J=8.6 Hz), 8.32(2H, m), 9.00(2H, d, J=4.9 Hz)

Example 52 (Synthesis of Compound No. 50)

The procedure described in Example 14 was repeated using Compound No. 3 and 3-methylaniline, to obtain N-(3-methylphenyl)-3-[6-(4-t-butylphenylsulfonylamino)-5-(2-methoxyphenoxy)-2-(2-pyrimidinyl)-4-pyrimidinyloxy]propionamide as a pale yellow oil.

$^1$H-NMR(CDCl$_3$, ppm, TMS): 1.29(9H, s), 2.29(3H, s), 2.74(2H, t, J=6.2 Hz), 3.86(3H, s), 4.85(2H, t, J=6.2 Hz), 6.70(1H, dt, J=7.8, 1.5 Hz), 6.85~7.30(7H, m), 7.40(1H, t, J=4.9 Hz), 7.42(2H, d, J=8.8 Hz), 8.36(2H, m), 8.93(2H, d, J=4.9 Hz) IR(KBr)cm$^{-1}$: 2965, 1685, 1615, 1580, 1560, 1500, 1340, 1255, 1175, 1085, 750

Example 53 (Synthesis of Compound No. 53)

The procedure described in Example 14 was repeated using Compound No. 3 and 2-isopropylaniline, to obtain N-(2-isopropylphenyl)-3-[6-(4-t-butylphenylsulfonylamino)-5-(2-methoxyphenoxy)-2-(2-pyrimidinyl)-4-pyrimidinyloxy]propionamide as a pale yellow oil.

$^1$H-NMR(CDCl$_3$, ppm, TMS): 1.06(6H, d, J=6.8 Hz), 1.29(9H, s), 2.86(2H, t, J=6.5 Hz), 3.03(1H, sep, J=6.8 Hz), 3.92(3H, s), 4.92(2H, t, J=6.5 Hz), 6.80(1H, t, J=7.7 Hz), 6.95(1H, d, J=7.1 Hz), 6.99~7.32(6H, m), 7.36(1H, d, J=8.1 Hz), 7.43(2H, d, J=8.6 Hz), 8.43(2H, d, J=8.6 Hz), 8.59(2H, d, J=4.9 Hz), 8.86(1H, brs)

Example 54 (Synthesis of Compound No. 88)

Oxalyl chloride (9.5 mg) was added to a solution of Compound No. 3(40.2 mg) in methylene chloride (0.3 ml). One droplet of dimethylformamide was added thereto, and the resulting mixture was stirred at room temperature for 30 minutes. Subsequently, 2-amino-5-trifluoromethyl-1,3,4-thiadiazole (24.1 mg) was added, and the mixture was stirred overnight at room temperature. Ethyl acetate (10 ml) was added to the reaction mixture, followed by washing successively with sat. aq. NaHCO$_3$, water, 1N-HCl, water, and saturated brine and drying over anhydrous sodium sulfate. Solvent was evaporated under reduced pressure, then the residue was purified by preparative thin layer chromatography (eluent:chloroform-methanol (5:1)), dissolved in ethyl acetate, washed with 1N-HCl and saturated brine, and dried over anhydrous sodium sulfate. When the solvent was evaporated under reduced pressure, there was obtained N-(5-trifluoromethyl-1,3,4-thiadiazole-2-yl)-3-[6-(4-t-butylphenylsulfonylamino)-5-(2-methoxyphenoxy)-2-(2-pyrimidinyl)-4-pyrimidinyloxy]propionamide as a pale yellow powder (32.9 mg).

$^1$H-NMR(CDCl$_3$, ppm, TMS): 1.29(9H, s), 3.12(2H, t, J=6.7 Hz), 3.85(3H, s), 4.83(2H, t, J=6.7 Hz), 6.74(1H, t, J=7.6 Hz), 6.86(1H, d, J=7.6 Hz), 6.90(1H, d, J=7.6 Hz), 6.99(1H, t, J=7.6 Hz), 7.45(2H, d, J=8.6 Hz), 7.49(1H, t, J=4.9 Hz), 8.44(2H, m), 9.00(1H, brs), 9.26(2H, d, J=4.9 Hz); IR(KBr)cm$^{-1}$: 2965, 1700, 1620, 1580, 1560, 1500, 1330, 1255, 1175, 1085, 750

Example 55 (Synthesis of Compound No. 89)

The procedure described in Example 14 was repeated using Compound No. 3 and 2-ethylaniline, to obtain N-(2-ethylphenyl)-3-[6-(4-t-butylphenylsulfonylamino)-5-(2-methoxyphenoxy)-2-(2-pyrimidinyl)-4-pyrimidinyloxy]propionamide as a pale yellow powder.

$^1$H-NMR(CDCl$_3$, ppm, TMS): 1.07(3H, t, J=7.6 Hz), 1.29(9H, s), 2.50(2H, q, J=7.6 Hz), 2.84(2H, t, J=6.5 Hz), 3.90(3H, s), 4.94(2H, t, J=6.5 Hz), 6.78(1H, t, J=7.6 Hz), 6.93(1H, d, J=7.6 Hz), 6.97~7.32(6H), 7.43(1H, t, J=4.6 Hz), 7.43(2H, d, J=8.55 Hz), 8.43(2H, d, J=8.5 Hz), 8.59 (1H, brs), 8.65(2H, d, J=4.6 Hz), 8.83(1H,b IR(KBr)cm$^{-1}$: 2965, 1670, 1618, 1499, 1455, 1384, 1255, 1175, 1083, 752

Example 56 (Synthesis of Compound No. 90)

The procedure described in Example 54 was repeated using Compound No. 3 and 1,2-phenylenediamine, to obtain N-(2-aminophenyl)-3-[6-(4-t-butylphenylsulfonylamino)-5-(2-methoxyphenoxy)-2-(2-pyrimidinyl)-4-pyrimidinyloxy] propionamide as a pale yellow powder.

$^1$H-NMR(CDCl$_3$, ppm, TMS): 1.29(9H, s), 2.82(2H, t, J=6.5 Hz), 3.88(3H, s), 4.87(2H, t, J=6.5 Hz), 6.70~7.14 (8H), 7.33(1H, t, J=4.9 Hz), 7.42(2H, d, J=8.5 Hz), 8.36(2H, m), 8.77(2H, d, J=4.9 Hz) IR(KBr)cm$^{-1}$: 2965, 1665, 1620, 1580, 1560, 1500, 1342, 1255, 1175, 1080, 750

Example 57 (Synthesis of Compound No. 91)

The procedure described in Example 14 was repeated using Compound No. 3 and phenylhydrazine, to obtain N'-phenyl-3-[6-(4-t-butylphenylsulfonylamino)-5-(2-methoxyphenoxy)-2-(2-pyrimidinyl)-4-pyrimidinyloxy] propionohydrazide as a pale yellow powder.

$^1$H-NMR(CDCl$_3$, ppm, TMS): 1.30(9H, s), 2.77(2H, t, J=6.7 Hz), 3.94(3H, s), 4.80(2H, t, J=6.7 Hz), 6.24(1H, brs), 6.74~7.24(9H), 7.33(1H, t, J=4.9 Hz), 7.46(2H, d, J=8.6 Hz), 8.47(2H, d, J=8.6 Hz), 8.90(2H, d, J=4.9 Hz) IR(KBr) cm$^{-1}$: 2965, 1680, 1620, 1580, 1560, 1500, 1340, 1255, 1175, 1080, 775

Example 58 (Synthesis of Compound No. 92)

The procedure described in Example 54 was repeated using Compound No. 3 and 2-aminopyridine, to obtain N-(2-pyridyl)-3-[6-(4-t-butylphenylsulfonylamino)-5-(2-methoxyphenoxy)-2-(2-pyrimidinyl)-4-pyrimidinyloxy] propionamide as a pale yellow powder.

$^1$H-NMR(CDCl$_3$, ppm, TMS): 1.29(9H, s), 2.77(2H, t, J=6.2 Hz), 3.86(3H, s), 4.86(2H, t, J=6.2 Hz), 6.68(1H, dt, J=7.8, 1.2 Hz), 6.86(1H, d, J=7.6 Hz), 6.90~7.07(3H), 7.42(1H, t, J=4.9 Hz), 7.42(2H, d, J=8.5 Hz), 7.68(1H, dt, J=7.9, 1.8 Hz), 8.14(1H, d, J=8.3 Hz), 8.25(1H, m), 8.39(2H, m), 8.49(1H, brs), 9.04(2H, d, J=4.9 Hz) IR(KBr)cm$^{-1}$: 2965, 1695, 1620, 1580, 1560, 1500, 1340, 1255, 1175, 1085, 750

Example 59 (Synthesis of Compound No. 93)

The procedure described in Example 14 was repeated using Compound No. 3 and 2-isopropenylaniline, to obtain N-(2-isopropenylphenyl)-3-[6-(4-t-butylphenylsulfonylamino)-5-(2-methoxyphenoxy)-2-(2-pyrimidinyl)-4-pyrimidinyloxy]propionamide as a pale yellow powder.

$^1$H-NMR(CDCl$_3$, ppm, TMS): 1.28(9H, s), 1.91(3H, s), 2.75(2H, t, J=6.0 Hz), 3.88(3H, s), 4.85(1H, brs), 4.89(2H, t, J=6.0 Hz), 5.16(1H, brs), 6.63(1H, t, J=7.4 Hz), 6.88(1H, d, J=7.6 Hz), 6.92~7.14(4H, m), 7.23(1H, m), 7.41(1H, t, J=4.6 Hz), 7.41(2H, d, J=8.6 Hz), 7.96(1H, brs), 8.09(1H, d, J=8.0 Hz), 8.39(2H, m), 8.92(2H, d, J=4.6 Hz) IR(KBr)cm$^{-1}$: 2965, 1685, 1620, 1580, 1560, 1500, 1345, 1255, 1175, 1085, 750

Example 60 (Synthesis of Compound No. 94)

The procedure described in Example 14 was repeated using Compound No. 3 and 2-(methylthio)aniline, to obtain N-(2-methylthiophenyl)-3-[6-(4-t-butylphenylsulfonylamino)-5-(2-methoxyphenoxy)-2-(2-pyrimidinyl)-4-pyrimidinyloxy]propionamide as a pale yellow powder.

$^1$H-NMR(CDCl$_3$, ppm, TMS): 1.29(9H, s), 2.24(3H, s), 2.82(2H, t, J=6.0 Hz), 3.87(3H, s), 4.92(21H, t, J=6.0 Hz), 6.63(1H, t, J=7.4 Hz), 6.85(1H, d, J=7.1 Hz), 6.89~7.02 (2H), 7.10(1H, dt, J=7.6, 1.2 Hz), 7.26(1H, m), 7.41(1H, t, J=4.6 Hz), 7.41(2H, d, J=8.6 Hz), 8.12(1H, d, J=8.1 Hz), 8.36(2H, m), 8.55(1H, brs), 8.93(2H, d, J=4.6 Hz) IR(KBr) cm$^{-1}$: 2960, 1685, 1620, 1580, 1560, 1500, 1340, 1255, 1175, 1080, 775

Example 61 (Synthesis of Compound No. 95)

The procedure described in Example 14 was repeated using Compound No. 3 and 2-t-butylaniline, to obtain N-(2-t-butylphenyl)-3-[6-(4-t-butylphenylsulfonylamino)-5-(2-methoxyphenoxy)-2-(2-pyrimidinyl)-4-pyrimidinyloxy] propionamide as a pale yellow powder.

$^1$H-NMR(CDCl$_3$, ppm, TMS): 1.29(18H, s), 2.86(2H, t, J=6.4 Hz), 3.91(3H, s), 4.96(2H, t, J=6.6 Hz), 6.74~7.54 (9H), 8.42(2H, m), S. 56(2H, m), 8.73(1H, brs), 8.83, H, brs), 8.99(2H, d, J=4.9 Hz), IR(KBr)cm$^{-1}$: 2965, 1675, 1620, 1580, 1560, 1500, 1345, 1255, 1175, 1080, 775

Example 62 (Synthesis of Compound No. 96)

The procedure described in Example 54 was repeated using Compound No. 3 and 3-aminopyridine, to obtain N-(3-pyridyl)-3-[6-(4-t-butylphenylsulfonylamino)-5-(2-methoxyphenoxy)-2-(2-pyrimidinyl)-4-pyrimidinyloxy] propionamide as a pale yellow powder.

$^1$H-NMR(CDCl$_3$, ppm, TMS): 1.29(9H, s) 2.81(2H, to J=6.2 Hz), 3.82(3H, s), 4.85(2H, t, J=6.2 Hz), 6.73(1H, dt, J=7.7, 1.2 Hz), 6.85(1H, dd, J=8.1, 1.2 Hz), 6.90(1H, d, J=8.1 Hz), 6.98(1H, dt, J=7.7, 1.5 Hz), 7.22(1H, dd, J=8.3, 4.6 Hz), 7.41(1H, t, J=4.9 Hz), 7.43(2H, d, J=9.0 Hz), 8.08(1H, brd, J=8.3 Hz), 8.33(1H, dd, J=4.6, 1.2 Hz), 8.34(2H, m), 8.46(1H, d, J=2.7 Hz), 8.61(1H, brs) 8.93(1H, d, J=4.9 Hz) IR(KBr)cm$^{-1}$: 2965, 1695, 1620, 1580, 1560, 1500, 1340, 1255, 1175, 1085, 750

Example 63 (Synthesis of Compound No. 97)

The procedure described in Example 54 was repeated using Compound No. 2 and 2-aminopyridine, to obtain N-(2-pyridyl)- [6-(4-t-butylphenylsulfonylamino)-5-(2-methoxyphenoxy)-2-(2-pyrimidinyl)-4-pyrimidinyloxy] acetamide as a pale yellow powder.

$^1$NMR(CDCl$_3$, ppm, TMS): 1.28(9H5 s), 3.93(3H, s), 5.12(2H, s), 6.80~7.16(5H), 7.30~7.50(3H), 7.65(1H, t, J=7.2 Hz), 8.12(1H, d, J=8.3 Hz), 8.27(1H, m), 8.37(2H, m), 8.58(1H, brs), 8.99(2H, m) IR(KBr)cm$^{-1}$: 2965, 1705, 1620, 1583, 1560, 1500, 1340, 1255, 1175, 1085, 750

Example 64 (Synthesis of Compound No. 98)

The procedure described in Example 54 was repeated using Compound No. 4 and 2-aminopyridine, to obtain N-(2-pyridyl)-4-[6-(4-t-butylphenylsulfonylamino)-5-(2-methoxyphenoxy)-2-(2-pyrimidinyl)-4-pyrimidinyloxy] butyramide as a pale yellow powder.

$^1$H-NMR(CDCl$_3$, ppm, TMS): 1.29(9H, s), 2.05(2H, m), 2.23(2H, t, J=7.1 Hz), 3.88(3H, s), 4.54(2H, t, J=5.7 Hz), 6.80~7.20(5H), 7.41(1H, t, J=4.9 Hz), 7.42(2H, d, J=8.8 Hz), 7.75(1H, dt, J=7.9, 1.7 Hz), 8.21(1H, m), 8.22(1H, d, J=7.8 Hz), 8.35(2H, m), 9.01(2H, d, J=4.9 Hz) IR(KBr)cm$^{-1}$: 2960, 1695, 1615, 1580, 1560, 1500, 1340, 1255, 1175, 1080, 750

Example 65 (Synthesis of Compound No. 99)

The procedure described in Example 54 was repeated using Compound No. 3 and 2,6-diisopropylaniline, to obtain N-(2,6-diisopropylphenyl)-3-[6-(4-t-butylphenylsulfonylamino)-5-(2-methoxyphenoxy)-2-(2-pyrimidinyl)-4-pyrimidinyloxy]-propionamide as a pale yellow powder.

¹H-NMR(CDCl₃, ppm, TMS): 1.05(12H, m), 1.29(9H, s), 2.93(2H, t, J=6.8 Hz), 3.10(2H, sep, J=6.8 Hz), 3.99(3H, s), 4.99(2H, t, J=6.8 Hz), 6.89(1H, t, J=7.6 Hz), 7.01(1H, d, J=7.8 Hz), 7.20(1H, d, J=7.8 Hz), 7.07~7.23(5H), 7.34(1H, t, J=7.8 Hz), 7.45(2H, d, J=8.3 Hz), 8.23(2H, d, J=4.4 Hz), 8.48(2H, m), 8.94(1H, brs), 9.70(1H, brs); IR(KBr)cm⁻¹: 2965, 1665, 1620, 1580, 1560, 1500, 1345, 1255, 1175, 1085, 750

Example 66(synthesis of Compound No. 100)

The procedure described in Example 14 was repeated using Compound No. 3 and allylamine, to obtain N-allyl-3-[6-(4-t-butylphenylsulfonylamino)-5-(2-methoxyphenoxy)-2-(2-pyrimidinylp)-4-pyrimidinyloxy]propionamide as a pale yellow powder.

¹H-NMR(CDCl₃, ppm, TMS): 1.29(9H, s), 2.63(2H, t, J=6.2 Hz), 3.81(2H, t, J=35.5 Hz), 3.93(3H, s), 4.79(2H, t, J=6.2 Hz), 5.03(1H, m), 5.09(1H, m), 5.75(1H, m), 6.84(1H, t, J=7.8 Hz), 6.97(2H, m), 7.10(1H, t, J=7.7 Hz), 7.42(1H, t, J=4.6 Hz), 7.42(2H, d, J=8.3 Hz), 8.38(2H, m), 8.80(1H, brs), 9.00(2H, d, J=4.6 Hz) IR(KBr)cm⁻¹: 2965, 1655, 1580, 1560, 1500, 1340, 1255, 1175, 1080, 750

Example 67 (Synthesis of Compound No. 101)

The procedure described in Example 54 was repeated using Compound No. 2 and 2-amino-3-methylpyridine, to obtain N-(3-methyl-2-pyridyl)-[6-(4-t-butylphenylsulfonylamino)-5-(2-methoxyphenoxy)-2-(2-pyrimidinyl)-4-pyrimidinyloxy]acetamide as a pale yellow powder.

¹H-NMR(CDCl₃, ppm, TMS): 1.30(9H, s), 2.11(3H, s), 3.86(3H, s), 5.20(2H, s), 6.81(1H, t, J=7.6 Hz), 6.88~7.03(2H, m), 7.10(1H, m), 7.11(1H, dd, J=7.6, 4.6 Hz), 7.43(1H, t, J=4.9 Hz) 7.44(2H, d, J=8.6 Hz), 7.53(1H, m) 8.26(1H, m) 8.38(2H, m) 9.00(2H, d, J=4.9 Hz)

Example 68 (Synthesis of Compound No. 102)

The procedure described in Example 14 was repeated using Compound No. 3 and 1-naphthylamine, to obtain N-(1-naphthyl)-3-[6-(4-t-butylphenylsulfonylamino)-5-(2-methoxyphenoxy)-2-(2-pyrimidinyl)-4-pyrimidinyloxy]propionamide as a pale yellow powder.

¹H-NMR(CDCl₃, ppm, TMS): 29(9H, s), 2.96(2H, t, J=6.2 Hz), 3.83(3H, s), 5.01(2H, t, J=6.2 Hz), 6.75(1H, t, J=7.3 Hz), 6.83(1H, d, J=7.8 Hz), 6.99(2H, m), 7.14(1H, m), 7.30(1H, t, J=7.6 Hz), 7.37~7.51(4H, m), 7.67(1H, d, J=7.1 Hz), 7.74(1H, d, J=8.3 Hz), 7.83(2H, m), 8.40(2H, m), 8.50(2H, m), 9.15(1H, brs); IR(KBr)cm⁻¹: 2965, 1670, 1580, 1560, 1500, 1340, 1255, 1175, 1080, 750

Example 69 (Synthesis of Compound No. 103)

The procedure described in Example 14 was repeated using Compound No. 3 and 2-aminothiazoline, to obtain N-(2-thiazolinyl)-3-[6-(4-t-butylphenylsulfonylamino)-5-(2-methoxyphenoxy)-2-(2-pyrimidinyl)-4-pyrimidinyloxy]propionamide as a pale yellow powder.

¹H-NMR(CDCl₃, ppm, TMS): 1.29(9H, s) 2.95(2H, t, J=6.4 Hz), 3.41(2H, t, J=8.6 Hz), 3.92(3H, s), 4.02(2H, t, J=8.6 Hz), 4.83(2H, t, J=6.4 Hz), 6.84(1H, dt, J=7.7, 1.5 Hz), 6.96(1H, dd, J=7.7, 1.5 Hz), 6.99(1H, dd, J=7.7, 1.7 Hz), 7.07(1H, dt, J=7.7, 1.7 Hz), 7.42(2H, d, J=9.0 Hz), 7.44(1H, t, J=4.9 Hz), 8.34(2H, m), 9.05(2H, d, J=4.9 Hz) IR(KBr)cm⁻¹: 2965, 1620, 1580, 1560, 1500, 1340, 1255, 1175, 1085, 750

Example 70 (Synthesis of Compound No. 104)

The procedure described in Example 54 was repeated using Compound No. 3 and aminopyrazine, to obtain N-(2-pyrazinyl)-3-[6-(4-t-butylphenylsulfonylamino)-5-(2-methoxyphenoxy)-2-(2-pyrimidinyl)-4-pyrimidinyloxy]propionamide as a pale yellow powder.

¹H-NMR(CDCl₃, ppm, TMS): 1.29(9H, s), 2.85(2H, t, J=6.4 Hz), 3.88(3H, s), 4.86(2H, t, J=6.4 Hz), 6.71(1H, t, J=8.1 Hz), 6.87(1H, d, J=7.3 Hz), 6.96(2H, m), 7.43(3H, m), 8.22(1H, dd, J=2.4, 1.5 Hz), 8.34(1H, d, J=2.4 Hz), 8.40(3H, m), 8.59(1H, brs), 9.05(2H, d, J=4.9 Hz), 9.46(1H, s) IR(KBr)cm⁻¹: 2960, 1700, 1580, 1560, 1500, 1345.1255, 1085, 750

Example 71 (Synthesis of Compound No. 105)

The procedure described in Example 54 was repeated using Compound No. 3 and 2-aminopyrimidine, to obtain N-(2-pyrimidinyl)-3-[6-(4-t-butylphenylsulfonylamino)-5-(2-methoxyphenoxy)-2-(2-pyrimidinyl)-4-pyrimidinyloxy]propionamide as a pale yellow powder.

¹H-NMR(CDCl₃, ppm, TMS): 1.29(9H, s), 3.13(2H, t, J=6.4 Hz), 3.90(3H, s), 4.90(2H, t, J=6.4 Hz), 6.77(1H, t, J=8.1 Hz), 6.91(1H, d, J=7.1 Hz), 6.99(1H, t, J=4.9 Hz), 7.03(2H, m), 7.42(3H, m)

Example 72 (Synthesis of Compound No. 106)

The procedure described in Example 14 was repeated using Compound No. 2 and 2-pyridylhydrazine, to obtain N'-(2-pyridyl)-[6-(4-t-butylphenylsulfonylamino)-5-(2-methoxyphenoxy)-2-(2-pyrimidinyl)-4-pyrimidinyloxy]acetohydrazide as a pale yellow powder.

Example 73 (Synthesis of Compound No. 107)

The procedure described in Example 14 was repeated using Compound No. 3 and 2-pyridylhydrazine, to obtain N'-(2-pyridyl)-3-[6-(4-t-butylphenylsulfonylamino)-5-(2-methoxyphenoxy)-2-(2-pyrimidinyl)-4-pyrimidinyloxy]propionohydrazide as a pale yellow powder.

Example 74 (Synthesis of Compound No. 68)

The procedure described in Example 14 was repeated using Compound No. 3 and 2,6-dimethylaniline, to obtain N-(2,6-dimethylphenyl)-3-[6-(4-t-butylphenylsulfonylamino)-5-(2-methoxyphenoxy)-2-(2-pyrimidinyl)-4-pyrimidinyloxy]propionamide as a pale yellow oil.

¹H-NMR(CDCl₃, ppm, TMS): 1.29(9H, s), 2.14(6H, s), 2.86(2H, t, J=6.7 Hz), 3.88(3H, s), 4.96(2H, t, J=6.7 Hz), 6.83(1H, t, J=7.8 Hz), 6.91(1H, d, J=8.1 Hz), 6.95~7.16(6H, m), 7.44(2H, d, J=8.8 Hz), 8.40(2H, m), 8.49(2H, d, J=4.6 Hz) IR(KBr)cm⁻¹: 2965, 1670, 1620, 1580, 1560, 1500, 1345, 1255, 1175, 1080, 750

Example 75 (Synthesis of Compound No. 66)

The procedure described in Example 6 was repeated using Compound No. 2 and methanol, to obtain methyl[6-(4-t-butylphenylsulfonylamino)-5-(2-methoxyphenoxy)-2-(2-pyrimidinyl)-4-pyrimidinyloxy]acetate as a pale yellow oil.

¹H-NMR(CDCl₃, ppm, TMS): 1.29(9H, s), 3.71(3H, s), 4.00(3H, s), 5.14(2H, s), 6.89(1H, t, J=8.1 Hz), 7.00(1H, d, J=8.1 Hz), 7.12(1H, t, J=8.1 Hz), 7.32(1H, m), 7.41(1H, t, J=4.9 Hz), 7.42(2H, d, J=8.3 Hz), 8.37(2H, m), 8.99(2H, d, J=4.9 Hz) IR(KBr)cm⁻¹: 2960, 1760, 1620, 1580, 1560, 1500, 1345, 1255, 1175, 1085, 750

Example 76 (Synthesis of Compound No. 67)

The procedure described in Example 6 was repeated using Compound No. 4 and methanol, to obtain methyl 4-[6-(4- t-butylphenylsulfonylamino)-5-(2-methoxyphenoxy)-2-(2-pyrimidinyl)-4-pyrimidinyloxy]butyrate as a pale yellow oil.

$^1$H-NMR(CDCl$_3$, ppm, TMS): 1.29(9H, s), 1.95(2H, m), 2.19(2H, t, J=7.3 Hz), 3.63(3H, s), 3.90(3H, s), 4.50(2H, t, J=6.1 Hz), 6.84(1H, dt, J=7.4, 1.6Hz), 6.92–7.01(2H, m), 7.09(1H, dt, J=8.1, 2.7 Hz), 7.42(1H, t, J=4.9 Hz), 7.42(2H, d, J=8.5 Hz), 8.34(2H, m), 9.05(2H, d, J=4.9 Hz) IR(KBr)cm$^{-1}$: 2965, 1735, 1620, 1580, 1560, 1500, 1345, 1255, 1175, 1085, 750

Example 77 (Synthesis of Compound No. 69)

The procedure described in Example 6 was repeated using Compound No. 3 and isopropyl alcohol, to obtain isopropyl 3-[6-(4-t-butylphenylsulfonylamino)-5-(2-methoxyphenoxy)-2-(2-pyrimidinyl)-4-pyrimidinyloxy] propionate as a pale yellow oil.

$^1$H-NMR(CDCl$_3$, ppm, TMS): 1.16(6H, d, J=6.3 Hz), 1.29(9H, s), 2.65(2H, t, J=6.2 Hz), 3.93(3H, s), 4.77(2H, t, J=6.3 Hz), 4.95(1H, sep, J=6.3 Hz), 6.83(1H, t, J=7.8 Hz), 6.96(1H, dd, J=8.3, 1.5 Hz), 7.00~7.15(2H, m), 7.41(2H, d, J=8.5 Hz), 7.42(1H, t, J=4.9 Hz), 8.30~8.40(2H, m), 9.01 (2H, d, J=4.9 Hz); IR(KBr)cm$^{-1}$: 2965, 1730, 1620, 1580, 1560, 1500, 1345, 1255, 1175, 1085, 750

Example 78 (Synthesis of Compound No. 54)

The procedure described in Example 14 was repeated using Compound No. 2 and N-benzylethanolamine, to obtain N-benzyl-N-(2-hydroxyethyl)-[6-(4-t-butylphenylsulfonylamino)-5-(2-methoxyphenoxy)-2-(2-pyrimidinyl)-4-pyrimidinyloxy]acetamide as a pale yellow oil.

$^1$H-NMR(CDCl$_3$,ppm, TMS): 1.29(9H, s), 3.47(2H, m), 3.74(2H, m), 4.03(3H, s), 4.57(2H, s), 5.56(2H, s), 6.87–7.20(8H, m), 7.41(1H, t, J=4.9 Hz), 7.42(2H, d, J=8.3 Hz), 7.53(1H, m), 8.42(2H, m) 8.88(2H, d, J=4.9 Hz); IR(KBr)cm$^{-1}$: 3430, 2965, 1665, 1620, 1580, 1560, 1500, 1345, 1255, 1175, 1085, 750

Example 79 (Synthesis of Compound No. 55)

The procedure described in Example 14 was repeated using Compound No. 3 and 2-(aminomethyl)pyridine, to obtain N-(2-pyridylmethyl)-3-[6-(4-t-butylphenylsulfonylamino)- 5-(2-methoxyphenoxy)-2-(2-pyrimidinyl)-4-pyrimidinyloxy]propionamide as a pale yellow oil.

$^1$H-NMR(CDCl$_3$, ppm, TMS): 1.29(9H, s), 2.71(2H, t, J=6.4 Hz), 3.91(3H, s), 4.63(2H, d, J=5.4 Hz), 4.83(2H, t, J=6.4 Hz), 6.81(1H, dt, J=7.8, 1.5 Hz), 6.93(1H, dd, J=7.8, 1.5 Hz), 6.98(1H, brd, J=7.8 Hz), 7.06(1H, dd, J=7.8, 1.5 Hz), 7.42(2H, d, J=8.3 Hz), 7.43(1H, t, J=4.9 Hz), 7.51(1H, d, J=7.8 Hz), 7.80–7.95(2H, m), 8.32(2H, m), 8.49(1H, d, J=4.9 Hz), 9.00(2H, d, J=4.9 Hz); IR(KBr)cm$^{-1}$: 2965, 1665, 1620, 1580, 1560, 1500, 1345, 1255, 1175, 1085, 750

Example 80 (Synthesis of Compound No. 56)

The procedure described in Example 14 was repeated using Compound No. 3 and 2-(2-aminoethyl)pyridine, to obtain N-[2-(2-pyridyl)ethyl)-3-[6-(4-t-butylphenylsulfonylamino)-5-(2-methoxyphenoxy)-2-(2-pyrimidinyl)-4-pyrimidinyloxy]propionamide as a pale yellow oil.

$^1$H-NMR(CDCl$_3$, ppm, TMS): 1.29(9H, s), 2.62(2H, t, J=6.2 Hz), 3.20(2H, t, J=6.2 Hz), 3.68(2H, m), 3.95(3H, s), 4.73(2H, d, J=6.2 Hz), 6.83(1H, brt, J=7.7 Hz), 6.93–7.03 (2H, m), 7.09(1H, dt, J=7.7, 1.5 Hz), 7.31–7.49(3H, m), 7.42(2H, d, J=8.6 Hz), 7.45(1H, t, J=4.9 Hz), 7.84(1H, t, J=7.4 Hz), 8.32(2H, m), 8.48(1H, d, J=4.6 Hz), 9.04(2H, d, J=4.9 Hz) IR(KBr)cm$^{-1}$: 2965, 1655, 1620, 1580, 1560, 1500, 1340, 1255, 1175, 1080, 750

Example 81 (Synthesis of Compound No. 57)

The procedure described in Example 14 was repeated using Compound No. 3 and a-methylbenzylamine, to obtain N-(α-methylbenzyl)-3-[6-(4-t-butylphenylsulfonylamino)-5-(2-methoxyphenoxy)-2-(2-pyrimidinyl)-4-pyrimidinyloxy]propionamide as a pale yellow oil.

$^1$H-NMR(CDCl$_3$, ppm, TMS): 1.29(9H, s), 2.62(2H, t, J=6.2 Hz), 3.20(2H, t, J=6.2 Hz), 3.68(2H, m), 3.95(3H, s), 4.73(2H, d, J=6.2 Hz), 6.83(1H, brt, J=7.7 Hz), 6.93–7.03 (2H, m), 7.09(1H, dt, J=7.7, 1.5 Hz), 7.31–7.49(3H, m), 7.42(2H, d, J=8.6 Hz), 7.45(1H, t, J=4.9 Hz), 7.84(1H, t, J=7.4 Hz), 8.32(2H, m), 8.48(1H, d, J=4.6 Hz), 9.04(2H, d, J=4.9 Hz) IR(KBr)cm$^{-1}$: 2965, 1655, 1620, 1580, 1560, 1500, 1340, 1255, 1175, 1080, 750

Example 82 (Synthesis of Compound No. 58)

The procedure described in Example 14 was repeated using Compound No. 3 and N-benzylmethylamine, to obtain N-benzyl-N-methyl-3-[6-(4-t-butylphenylsulfonylamino)-5-(2-methoxyphenoxy)-2-(2-pyrimidinyl)-4-pyrimidinyloxy]propionamide as a pale yellow oil.

$^1$H-NMR(CDCl$_3$, ppm, TMS): 1.28(9H, s), 2.77(2H, t, J=6.6 Hz), 2.85(3H, s), 3.96(3H, s), 4.53(2H, s), 4.91(2H, t, J=6.6 Hz), 6.80(1H, t, J=7.4 Hz), 6.96(1H, d, J=8.1 Hz), 7.01–7.31(7H, m), 7.40(2H, d, J=8.5 Hz), 7.41(1H, t, J=4.9 Hz), 8.32(2H, m), 9.00(2H, d, J=4.9 Hz) IR(KBr)cm$^{-1}$: 2965, 1645, 1620, 1580, 1560, 1500, 1345, 1255, 1175, 1085, 750

Example 83 (Synthesis of Compound No. 59)

The procedure described in Example 14 was repeated using Compound No. 3 and N-methylaniline, to obtain N-methyl-N-phenyl-3-[6-(4-t-butylphenylsulfonylamino)-5-(2-methoxyphenoxy)-2-(2-pyrimidinyl)-4-pyrimidinyloxy]propionamide as a pale yellow oil.

$^1$H-NMR(CDCl$_3$, ppm, TMS): 1.28(9H, s), 2.45(2H, t, J=6.1 Hz), 3.18(3H, s), 3.96(3H, s), 4.80(2H, t, J=6.1 Hz), 6.81(1H, t, J=7.3 Hz), 6.90–7.12(5H, m), 7.19–7.31(3H, m), 7.40(2H, d, J=8.5 Hz), 7.42(1H, t, J=4.9 Hz), 8.32(2H, m), 9.00(2H, d, J=4.9 Hz) IR(KBr)cm$^{-1}$: 2965, 1655, 1620, 1580, 1560, 1500, 1345, 1255, 1175, 1080, 750

Example 84 (Synthesis of Compound No. 60)

The procedure described in Example 14 was repeated using Compound No. 3 and 2-(trifluoromethyl)benzylamine, to obtain N-(2-trifluoromethylbenzyl)-3-[6-(4-t-butylphenylsulfonylamino)-5-(2-methoxyphenoxy)-2-(2-pyrimidinyl)-4-pyrimidinyloxy]propionamide as a pale yellow oil.

$^1$H-NMR(CDCl$_3$, ppm, TMS): 1.28(9H, s), 2.67(2H, t, J=6.2 Hz), 3.87(3H, s), 4.55(2H, d, J=5.9 Hz), 4.82(2H, t, J=6.2 Hz), 6.79(1H, t, J=7.6 Hz), 6.88–7.00(2H, m), 7.06 (1H, t, J=8.1 Hz), 7.22–7.47(6H, m), 7.58(1H, d, J=7.6 Hz), 8.34(2H, m), 8.87(2H, d, J=4.9 Hz) IR(KBr)cm$^{-1}$: 2965, 1665, 1620, 1580, 1560, 1500, 1315, 1255, 1165, 1080, 750

Example 85 (Synthesis of Compound No. 61)

The procedure described in Example 14 was repeated using Compound No. 3 and furfurylamine, to obtain N-furfuryl-3-[6-(4-t-butylphenylsulfonylamino)-5-(2-methoxyphenoxy)-2-(2-pyrimidinyl)-4-pyrimidinyloxy]propionamide as a pale yellow oil.

$^1$H-NMR(CDCl$_3$, ppm, TMS): 1.29(9H, s), 2.62(2H, t, J=6.3 Hz), 3.92(3H, s), 4.35(2H, d, J=5.4 Hz), 4.78(2H, t, J=6.3 Hz), 6.12(1H, t, J=3.2 Hz), 6.22(1H, dd, J=3.2, 1.9 Hz), 6.82(1H, t, J=7.8 Hz), 6.84~7.02(3H, m), 7.09(1H, t, J=7.8 Hz), 7.22(1H, d, J=1.9 Hz), 7.40(1H, d, J=4.9 Hz), 7.43(2H, d, J=8.3 Hz), 8.41(2H, m), 8.82(1H, brs), 8.96(2H, d, J=4.9 Hz) IR(KBr)cm$^{-1}$: 2965, 1660, 1620, 1580, 1560, 1500, 1340, 1255, 1175, 1080, 750

Example 86 (Synthesis of Compound No. 62)

The procedure described in Example 14 was repeated using Compound No. 2 and 2-methoxybenzylamine, to obtain N-(2-methoxybenzyl)-[6-(4-t-butylphenylsulfonylamino)-5-(2-methoxyphenoxy)-2-(2-pyrimidinyl)-4-pyrimidinyloxy]acetamide as a pale yellow oil.

$^1$H-NMR(CDCl$_3$, ppm, TMS): 1.29(9H, s), 3.69(3H, s), 3.78(3H, s), 4.34(2H, d, J=6.1 Hz), 5.01(2H, s), 6.46(1H, m), 6.71(1H, dt, J=7.81.5 Hz), 6.78(1H, d, J=8.3 Hz), 6.80–6.89(2H, m), 6.98(1H, d, J=7.8 Hz), 6.99(1H, t, J=7.8 Hz), 7.08(1H, dd, J=7.8, 1.5 Hz), 7.21(1H, dt, J=7.8, 1.5 Hz), 7.42(1H, m), 7.43(2H, d, J=8.3 Hz), 8.38(2H, m), 8.96(2H, d, J=4.9 Hz); IR(KBr)cm$^{-1}$: 2965, 1685, 1620, 1580, 1560, 1500, 1340, 1245, 1175, 1080, 775

Example 87 (Synthesis of Compound No. 63)

The procedure described in Example 14 was repeated using Compound No. 2 and α-methylbenzylamine, to obtain N-(α-methylbenzyl)-[6-(4-t-butylphenylsulfonylamino)-5-(2-methoxyphenoxy)-2-(2-pyrimidinyl)-4-pyrimidinyloxy]acetamide as a pale yellow oil.

$^1$H-NMR(CDCl$_3$, ppm, TMS): 1.29(9H, s), 1.30(3H, d, J=7.1 Hz), 3.80(3H, s), 4.94(1H, d, J=15.1 Hz), 4.99(1H, d, J=15.1 Hz), 5.12(1H, m), 6.38(1H, d, J=8.1 Hz), 6.73(1H, dt, J=7.8, 1.5 Hz), 6.81–6.92(2H, m), 7.03(1H, t, J=7.8 Hz), 7.09–7.30(5H, m), 7.42(1H, m), 7.43(2H, d, J=8.3 Hz), 8.38(2H, m), 8.98(2H, d, J=4.9 Hz)

Example 88 (Synthesis of Compound No. 64)

The procedure described in Example 14 was repeated using Compound No. 3 and 2-aminothiazole, to obtain N-(2-thiazolyl)-3-[6-(4-t-butylphenylsulfonylamino)-5-(2-methoxyphenoxy)-2-(2-pyrimidinyl)-4-pyrimidinyloxy]propionamide as a yellowish white powder.

$^1$H-NMR(DMSO-d$_6$, ppm, TMS): 1.27(9H, s), 2.72(2H, m), 3.70(3H, s), 4.61(2H, m), 6.54(1H, t, J=7.8 Hz), 6.61(1H, dd, J=7.8, 1.5 Hz), 6.79(1H, dt, J=7.8, 1.5 Hz), 6.91(1H, dd, J=7.8, 1.5 Hz), 7.19(1H, d, J=3.7 Hz), 7.46(1H, d, J=3.7 Hz), 7.55(2H, d, J=8.3 Hz), 7.67(1H, t, J=4.6 Hz), 8.31(2H, d, J=8.3 Hz), 9.10(2H, d, J=4.6 Hz) IR(KBr)cm$^{-1}$: 2965, 1690, 1620, 1560, 1500, 1340, 1255, 1175, 1080, 750

Example 89 (Synthesis of Compound No. 65)

The procedure described in Example 14 was repeated using Compound No. 3 and 2,5-dimethoxyaniline, to obtain N-(2,5-dimethoxyphenyl)-3-[6-(4-t-butylphenylsulfonylamino)-5-(2-methoxyphenoxy)-2-(2-pyrimidinyl)-4-pyrimidinyloxy]propionamide as a brown oil.

$^1$H-NMR(CDCl$_3$, ppm, TMS): 1.29(9H, s), 2.76(2H, t, J=6.0 Hz), 3.70(3H, s), 3.76(3H, s), 3.86(3H, s), 4.89(2H, t, J=6.0 Hz), 6.56(1H, dd, J=9.0,2.9H 6.63(1H, dd, J=7.6, 1.5 Hz), 6.73(1H, d, J=8.8 Hz), 6.85(1H, dd, J=8.2, 1.3 Hz), 6.90–7.40(2H, m), 7.41(2H, d, J=8.8 Hz), 7.42(1H, t, J=4.9 Hz), 7.89(1H, s), 8.04(1H, d, J=2.9 Hz), 8.34(2H, m), 9.00(2H, d, J=4.9 Hz); IR(KBr)cm$^{-1}$: 2965, 1685, 1620, 1580, 1560, 1500, 1340, 1255, 1175, 1085, 750

Example 90 (Synthesis of Compound No. 70)

The procedure described in Example 14 was repeated using Compound No. 3 and 2-aminophenol, to obtain N-(2-hydroxyphenyl)-3-[6-(4-t-butylphenylsulfonylamino)-5-(2-methoxyphenoxy)-2-(2-pyrimidinyl)-4-pyrimidinyloxy]propionamide as a pale yellow oil.

$^1$H-NMR(CDCl$_3$, ppm, TMS): 1.29(9H, s), 2.85(2H, m), 3.85(3H, s), 4.82(2H, m), 6.67–7.13(8H, m), 7.37(1H, m), 7.43(2H, d, J=8.3 Hz), 8.37(2H, brs), 8.85(2H, m), 8.95(1H, brs) IR(KBr)cm$^{-1}$: 2965, 1655, 1615, 1580, 1560, 1500, 1340, 1255, 1175, 1085, 750

Example 91 (Synthesis of Compound No. 71)

The procedure described in Example 14 was repeated using Compound No. 3 and 2-phenylglycinol, to obtain N-(α-hydroxymethylbenzyl)-3-[6-(4-t-butylphenylsulfonylamino)-5-(2-methoxyphenoxy)-2-(2-pyrimidinyl)-4-pyrimidinyloxy]propionamide as a pale yellow oil.

$^1$H-NMR (CDCl$_3$, ppm, TMS): 1.28(9H, s), 2.67(2H, m), 3.77(2H, m), 3.91(3H, s), 4.80(2H, m), 5.00(1H, m), 6.72–7.24(11H, m), 7.40(1H, m), 7.41(2H, d, J=8.8 Hz), 8.32(2H, m), 8.92(2H, m); IR(KBr)cm$^{-1}$: 2965, 1655, 1620, 1580, 1560, 1500, 1340, 1255, 1175, 1085, 750

Example 92 (Synthesis of Compound No. 72)

The procedure described in Example 14 was repeated using Compound No. 3 and aminodiphenylmethane, to obtain N-diphenylmethyl-3-[6-(4-t-butylphenylsulfonylamino)-5-(2-methoxyphenoxy)-2-(2-pyrimidinyl)-4-pyrimidinyloxy]propionamide as a pale yellow oil.

$^1$H-NMR(CDCl$_3$, ppm, TMS): 1.29(9H, s), 2.74(2H, t, J=6.4 Hz), 3.93(3H, s), 4.82(2H, t, J=6.5 Hz), 6.26(1H, d, J=8.0 Hz), 6.70–7.25(14H, m), 7.29(1H, t, J=4.6 Hz), 7.43(2H, d, J=8.6 Hz), 8.40(2H, d, J=8.6 Hz), 8.75(2H, d, J=4.6 Hz), 8.84(1H, brs) IR(KBr)cm$^{-1}$: 2965, 1655, 1620, 1580, 1560, 1500, 1340, 1255, 1175, 1080, 750

Example 93 (Synthesis of Compound No. 73)

The procedure described in Example 14 was repeated using Compound No. 3 and 4-nitrobenzylamine, to obtain N-(4-nitrobenzyl)-3-[6-(4-t-butylphenylsulfonylamino)-5-(2-methoxyphenoxy)-2-(2-pyrimidinyl)-4-pyrimidinyloxy]propionamide as a pale yellow oil.

$^1$H-NMR(CDCl$_3$, ppm, TMS): 1.28(9H, s), 2.72(2H, t, J=6.1 Hz), 3.93(3H, s), 4.46(2H, d, J=6.1 Hz), 4.84(2H, t, J=6.1 Hz), 6.72~7.24(5H, m), 7.32(2H, d,J=8.8 Hz), 7.40(1H, m), 7.42(2H, d, J=8.3 Hz), 8.03(2H, d, J=8.8 Hz), 8.36(2H, m), 8.091(2H (1H, d, J=4.6 Hz) IR(KBr)cm$^{-1}$: 2965, 1665, 1620, 1580, 1560, 1500, 1345, 1255, 1175, 1080, 750

Example 94 (Synthesis of Compound No. 74)

The procedure described in Example 14 was repeated using Compound No. 3 and 2-phenylglycinonitrile, to obtain N-(phenylcyanomethyl)-3-[6-(4-t- butylphenylsulfonylamino)-5-(2-methoxyphenoxy)-2-(2-pyrimidinyl)-4-pyrimidinyloxy]propionamide as a pale yellow oil.

$^1$H-NMR(CDCl$_3$, ppm, TMS): 1.29(9H, s) 2.681(2H, s)t, J=6.6 Hz), 3.95(3 Hz s), 4.74(2H, dt, J=1.15, 6.6 Hz), 4.87(1H, dt, J=11.5, 6.6 Hz), 6.28(1H, d, J=8.8 Hz), 6.77–7.50(12H, m), 8.02(1H, m), 8.42(2H, m), 8.83(2H, d, J=4.9 Hz) IR(KBr)cm$^{-1}$: 2965, 1685, 1620, 1580, 1560, 1500, 1340, 1255, 1175, 1080, 750

Example 95 (Synthesis of Compound No. 75)

The procedure described in Example 14 was repeated using Compound No. 3 and 2-methylallylamine, to obtain N-(2-methylallyl)-3-[6-(4-t-butylphenylsulfonylamino -5-(2-methoxyphenoxy)-2-(2-pyrimidinyl)-4-pyrimidinyloxy] propionamide as a pale yellow oil.

$^1$H-NMR(CDCl$_3$, ppm, TMS): 1.29(9H, s), 1.67(3H, s), 2.65(2H, t, J=6.3 Hz), 3.74(2H, d, J=5.9 Hz), 3.94(3H, s), 4.75(2H, brs), 4.80(2H, t, J=6.3 Hz), 6.50(1H, brs), 6.84(1H, t, J=8.0 Hz), 6.94–7.03(2H, m), 7.11(1H, t, J=8.1 Hz), 7.43(2H, d, J=8.5 Hz), 7.43(1H, t, J=4.6 Hz), 8.38(2H, m), 8.99(2H, d, J=4.6 Hz) IR(KBr)cm$^{-1}$: 2965, 1650, 1620, 1580, 1560, 1500, 1340, 1255, 1175, 1085, 750

Example 96 (Synthesis of Compound No. 76)

The procedure described in Example 14 was repeated using Compound No. 3 and cyclopropylamine, to obtain N-cyclopropyl-3-[6-(4-t-butylphenylsulfonylamino)-5-(2-methoxyphenoxy)-2-(2-pyrimidinyl)-4-pyrimidinyloxy] propionamide as a pale yellow oil.

$^1$H-NMR(CDCl$_3$, ppm, TMS): 0.40(2H, m), 0.70(2H, m), 1.29(9H, s), 2.54(21H, t, J=6.8 Hz), 2.58(1H, m), 3.94(3H, s), 4.75(2H, t, J=5.4 Hz), 6.33(1H, brs), 6.84(1H, t, J=7.2 Hz), 6.92–7.02(2H, m), 7.10(1H, t, J=8.1 Hz), 7.38–7.48 (3H, m), 8.42(2H, m), 9.02(2H, m) IR(KBr)cm$^{-1}$: 2965.1655, 1620, 1580, 1560, 1500, 1340, 1255, 1175, 1085, 750

Example 97 (Synthesis of Compound No. 77)

The procedure described in Example 14 was repeated using Compound No. 3 and methylamine, to obtain N-methyl-3-[6-(4-t-butylphenylsulfonylamino)-5-(2-methoxyphenoxy)-2-(2-pyrimidinyl)-4-pyrimidinyloxy] propionamide as a pale yellow oil.

$^1$H-NMR(CDCl$_3$, ppm, TMS): 1.29(9H, s), 2.58(2H, t, J=6.4 Hz), 2.70(3H, d, J=4.4 Hz), 3.93(3H, s), 4.76(2H, t, J=6.4 Hz), 6.85(1H, t, J=7.3 Hz), 6.92–7.02(2H, m), 7.10 (1H, t, J=7.8 Hz), 7.37–7.48(31H, m), 8.37(2H, m), 9.01(2H, m); IR(KBr)cm$^{-1}$: 2965, 1655, 1620, 1580, 1560, 1500, 1340, 1255, 1170, 1080, 750

Example 98 (Synthesis of Compound No. 78)

The procedure described in Example 14 was repeated using Compound No. 3 and dimethylamine, to obtain N,N-dimethyl-3-[6-(4-t-butylphenylsulfonylamino)-5-(2-methoxyphenoxy)-2-(2-pyrimidinyl)-4-pyrimidinyloxy] propionamide as a pale yellow oil.

$^1$H-NMR(CDCl$_3$, ppm, TMS): 1.29(9H, s), 2.70(2H, t, J=6.8 Hz), 2.88(3H, s), 2.93(3H, s), 3.95(3H, s), 4.85(2H, t, J=6.8 Hz), 6.82(1H, t, J=6.4 Hz), 6.93–7.13(3H, m), 7.36–7.45(3H, m), 8.33(2H, m), 9.00(2H, m) IR(KBr)cm$^{-1}$: 2965, 1645, 1620, 1580, 1560, 1500, 1340, 1255, 1175, 1085, 750

Example 99 (Synthesis of Compound No. 79)

The procedure described in Example 14 was repeated using Compound No. 3 and 2-chloroaniline, to obtain N-(2-chlorophenyl)-3-[6-(4-t-butylphenylsulfonylamino)-5-(2-methoxyphenoxy)-2-(2-pyrimidinyl)-4-pyrimidinyloxy] propionamide as a pale yellow oil.

$^1$H-NMR(CDCl$_3$, ppm, TMS): 1.29(9H, s), 2.80(2H, t, J=6.1 Hz), 3.86(3H, s), 4.90(2H, t, J=6.0 Hz), 6.60(1H, t, J=7.3 Hz), 6.85(1H, d, J=7.6 Hz), 6.89–7.02(2H, m), 7.06 (1H, dt, J=7.7, 1.6 Hz), 7.26(1H, dt, J=7.8, 1.5 Hz), 7.33(1H, dd, J=8.1, 1.5 Hz), 7.40(1H, t, J=4.9 Hz), 7.42(2H, d, J=8.3 Hz), 7.99(1H, brs), 8.18(1H, d, J=8.1 Hz), 8.38(2H, m), 8.93(2H, d, J=4.9 Hz) IR(KBr)cm$^{-1}$: 2965, 1695, 1620, 1580, 1560, 1500, 1340, 1255, 1175, 1085, 775

Example 100 (Synthesis of Compound No. 80)

The procedure described in Example 14 was repeated using Compound No. 3 and 2,6-difluorobenzylamine, to obtain N-(2,6-difluorobenzyl)-3-[6-(4-t-butylphenylsulfonylamino)-5-(2-methoxyphenoxy)-2-(2-pyrimidinyl)-4-pyrimidinyloxy]-propionamide as a pale yellow oil.

$^1$H-NMR(CDCl$_3$, ppm, TMS): 1.29(9H, s), 2.59(2H, t, J=6.2 Hz), 3.94(3H, s), 4.46(2H, d, J=5.6 Hz), 4.77(2H, t, J=6.2 Hz), 6.43(1H, m), 6.71–7.22(7H, m), 7.40(1H, m), 7.43(2H, d, J=8.3 Hz), 8.40(2H, d, J=8.3 Hz), 8.73(1H, brs), 8.97(2H, d, J=4.9 Hz); IR(KBr)cm$^{-1}$: 2965, 1665, 1625, 1580, 1560, 1500, 1340, 1245, 1175, 1080, 750

Example 101 (Synthesis of Compound No. 81)

The procedure described in Example 14 was repeated using Compound No. 3 and 1-aminoindan, to obtain N-(1-indanyl)-3-[6-(4-t-butylphenylsulfonylamino)-5-(2-methoxyphenoxy)-2-(2-pyrimidinyl)-4-pyrimidinyloxy] propionamide as a pale yellow oil.

$^1$H-NMR(CDCl$_3$, ppm, TMS): 1.29(9H, s), 1.67(1H, m), 2.52(2H, m), 2.68(2H, t, J=6.5 Hz), 2.85(2H, m), 3.92(3H, s), 4.84(2H, t, J=6.4 Hz), 5.48(1H, m), 6.47(1H, d, J=8.5 Hz), 6.80(1H, dt, J=7.7, 1.5 Hz), 6.90–7.25(7H, m), 7.28 (1H, t, J=4.9 Hz), 7.42(2H, d, J=8.8 Hz), 8.39(2H, d, J=8.6 Hz), 8.70(2H, d, J=4.6 Hz) IR(KBr)cm$^{-1}$: 2965, 1655, 1620, 1580, 1560, 1500, 1345, 1255, 1175, 1080, 750

Example 102 (Synthesis of Compound No. 82)

The procedure described in Example 14 was repeated using Compound No. 3 and 2-thiophenemethylamine, to obtain N-(2-thenyl)-3-[6-(4-t-butylphenylsulfonylamino)-5-(2-methoxyphenoxy)-2-(2-pyrimidinyl)-4-pyrimidinyloxy] propionamide as a pale yellow oil.

$^1$H-NMR(CDCl$_3$, ppm, TMS): 1.29(9H, s), 2.65(2H, t, J=6.4 Hz), 3.93(3H, s), 4.55(2H, d, J=5.9 Hz), 4.79(2H, t, J=6.4 Hz), 6.79–7.16(7H, m), 7.38(1H, t, J=4.9 Hz), 7.44 (2H, d, J=8.6 Hz), 8.41(2H, d, J=8.5 Hz), 8.72(1H, brs), 8.91(2H, d, J=4.9 Hz) IR(KBr)cm$^{-1}$: 2965, 1655, 1620, 1580, 1560, 1500, 1340, 1255, 1175, 1080, 750

Example 103 (Synthesis of Compound No. 83)

The procedure described in Example 14 was repeated using Compound No. 3 and 2,4-dimethoxybenzylamine, to obtain N-(2,4-dimethoxybenzyl)-3-[6-(4-t-butylphenylsulfonylamino)-5-(2-methoxyphenoxy)-2-(2-pyrimidinyl)-4-pyrimidinyloxy]propionamide as a pale yellow oil.

$^1$H-NMR(CDCl$_3$, ppm, TMS): 1.29(9H, s), 2.59(2H, t, J=6.2 Hz), 3.71(3H, s), 3.77(3H, s), 3.93(3H, s), 4.31(2H, d, J=5.6 Hz), 4.79(2H, t, J=6.2 Hz), 6.31–6.51(3H, m), 6.81 (1H, t, J=7.7 Hz), 6.95(1H, d, J=7.6 Hz), 6.90–7.14(3H, m), 7.37(1H, t, J=4.9 Hz), 7.42(2H, d, J=8.5 Hz), 8.39(2H, d, J=8.3 Hz), 8.82(1H, brs), 8.93(2H, d, J=4.9 Hz) IR(KBr) cm$^{-1}$: 2965, 1655, 1620, 1580, 1560, 1500, 1340, 1255, 1175, 1080, 775

Example 104 (Synthesis of Compound No. 84)

The procedure described in Example 54 was repeated using Compound No. 3 and 5-amino-1-ethylpyrazole, to obtain N-(1-ethyl-5-pyrazolyl)-3-[6-(4-t-butylphenylsulfonylamino)- 5-(2-methoxyphenoxy)-2-(2-pyrimidinyl)-4-pyrimidinyloxy]propionamide as a pale yellow oil.

$^1$H-NMR(CDCl$_3$, ppm, TMS): 1.29(9H, s), 1.29(3H, t, J=7.2 Hz), 2.88(2H, t, J=6.6 Hz), 3.94(2H, q, J=7.2 Hz), 3.95(3H, s), 4.89(2H, t, J=6.6 Hz), 6.15(1H, d, J=1.7 Hz), 6.85(1H, t, J=7.1 Hz), 6.94–7.07(2H, m), 7.12(1H, t, J=7.3 Hz), 7.32(1H, m), 7.45(2H, d, J=8.5 Hz), 7.52(1H, d, J=1.7 Hz), 8.45(2H, m), 8.53(2H, m), 9.70(1H, brs); IR(KBr)cm$^{-1}$: 2965, 1700, 1620, 1580, 1560, 1500, 1340, 1255, 1175, 1085, 750

Example 105 (Synthesis of Compound No. 85)

The procedure described in Example 54 was repeated using Compound No. 3 and 2-aminobenzofluoride, to obtain N-(2-trifluoromethylphenyl)-3-[6-(4-t-butylphenylsulfonylamino)-5-(2-methoxyphenoxy)-2-(2-pyrimidinyl)-4-pyrimidinyloxy]propionamide as a pale yellow oil.

$^1$H-NMR(CDCl$_3$, ppm, TMS): 1.29(9H, s), 2.80(2H, t, J=6.2 Hz), 3.87(3H, s), 4.89(2H, t, J=6.2 Hz), 6.72(1H, t, J=7.6 Hz), 6.88(1H, d, J=7.6 Hz), 6.92–7.04(2H, m), 7.31 (11H, d, J=7.8 Hz), 7.36(1H, t, J=4.9 Hz), 7.42(2H, d, J=8.6 Hz), 7.55(1H, t, J=7.7 Hz), 7.61(1H, d, J=7.8 Hz), 7.90(1H, d, J=8.1 Hz), 8.17(1H, brs), 8.39(2H, m), 8.83(2H, d, J=4.6 Hz); IR(KBr)cm$^{-1}$: 2965, 1685, 1620, 1580, 1560, 1500, 1340, 1255, 1170, 1080, 750

Example 106 (Synthesis of Compound No. 86)

The procedure described in Example 54 was repeated using Compound No. 3 and 2-nitroaniline, to obtain N-(2-nitrophenyl)-3-[6-(4-t-butylphenylsulfonylamino)-5-(2-methoxyphenoxy)-2-(2-pyrimidinyl)-4-pyrimidinyloxy] propionamide as a pale yellow oil.

$^1$H-NMR(CDCl3, ppm, TMS): 1.29(9H, s), 2.82(2H, t, J=5.9 Hz), 3.84(1H, s) 4.90(2H, t, J=5.9 Hz), 6.59(1H, m), 6.74–6.96(7H, m), 7.19(1H, dt, J=7.8, 1.5 Hz), 7.36–7.47(3 H, m), 7.63(1H, dt, J=7.9, 1.5 Hz), 8.18(2H, dd, J=8.4, 1.6Hz), 8.37(2H, m), 8.60(1H, brs), 8.68(1H, d, J=8.6Hz), 9.00(2H, d, J=4.6 Hz); IR(KBr)cm$^{-1}$: 2965, 1695, 1580, 1560, 1500, 1340, 1255, 1170, 1085, 745

Example 107 (Synthesis of Compound No. 87)

The procedure described in Example 54 was repeated using Compound No. 3 and ethyl 2-aminobenzoate, to obtain N-(2-ethoxycarbonylphenyl)-3-[6-(4-t-butylphenylsulfonylamino)-5-(2-methoxyphenoxy)-2-(2-pyrimidinyl)-4-pyrimidinyloxy ]propionamide as a pale yellow oil.

$^1$H-NMR(CDCl$_3$, ppm, TMS): 1.29(9H, s), 1.37(3H, t, J=7.1 Hz), 2.80(2H, t, J=6.0 Hz), 3.86(3H, s), 4.30(2H, q, J=7.2 Hz), 4.90(2H, t, J=56.9 Hz), 6.58(1H, dt, J=7.6, 1.7 Hz), 6.76–6.92(2H, m), 7.00(1H, d, J=7.1 Hz), 7.08(1H, dt, J=8.1, 1.5 Hz), 7.40(1H, t, J=74.6 Hz), 7.41(2H, d, J=8.3 Hz), 7.52(1H, dt, J=8.6, 1.5 Hz), 8.01(1H, dd, J=8.1, 1.5 Hz), 8.37(2H, d, J=8.5 Hz), 8.65(1H, d, J=8.6 Hz), 8.73(1H, brs), 9.00(2H, d, J=4.6 Hz); IR(KBr)cm$^{-1}$: 2965, 1685, 1580, 1560, 1500, 1345, 1260, 1175, 1085, 760

Example 108 (Synthesis of Compound No. 110)

The procedure described in Example 3 was repeated using 4-t-butyl-N-[6-(2,2-dimethyl-3-hydroxypropyloxy)-5-(2-methoxyphenoxy)-2-(2-pyrimidinyl)-4-pyrimidinyl] benzenesulfonamide, to obtain 3-[6-(4-t-butylphenylsulfonylamino)-5-(2-methoxyphenoxy)-2-(2-pyrimidinyl)-4-pyrimidinyloxy]-2,2-dimethylpropionic acid as a pale yellow powder.

$^1$H-NMR(CDCl$_3$, ppm, TMS): 1.14(6H, s), 1.27(9H, s), 3.74(3H, s), 4.48(2H, s), 6.50(1H, dt, J=7.4, 2.5 Hz), 6.83 (1H, d, J=7.6 Hz), 7.44(2H, d, J=8.8 Hz), 7.51(1H, t, J=4.9 Hz), 8.37(2H, m), 9.19(2H, d, J=4.9 Hz); IR(KBr)cm$^{-1}$: 3400, 2965, 1720, 1620, 1560, 1500, 1345, 1255, 1175, 1080, 750

Example 109 (Synthesis of Compound No. 111)

The procedure described in Example 3 was repeated using 4-t-butyl-N-[6-(2,2-diethyl-3-hydroxypropyloxy)-5-(2-methoxyphenoxy)-2-(2-pyrimidinyl)-4-pyrimidinyl] benzenesulfonamide, to obtain 2-[[6-(4-t-butylphenylsulfonylamino)-5-(2-methoxyphenoxy)-2-(2-pyrimidinyl)-4-pyrimidinyloxy]]methyl-2-ethylbutanoic acid as a pale yellow powder.

$^1$H-NMR(CDCl$_3$, ppm, TMS): 0.68(6H, t, J=7.3 Hz), 1.00–1.52(4H, m), 1.29(9H, s), 3.84(3H, s), 4.58(2H, s), 6.70(1H, dt, J=7.6, 1.5 Hz), 6.83–7.00(3H, m), 7.44(2H, d, J=8.8Hz), 7.48(1H, t, J=4.9Hz), 8.37(2H, m), 9.11(2H, d, J=4.9 Hz); IR(KBr)cm$^{-1}$: 3400, 2965, 1720, 1620, 1560, 1500, 1340, 1255, 1175, 1080, 750

Example 110 (Synthesis of Compound No. 112)

The procedure described in Example 3 was repeated using 4-t-butyl-N-[6-(3-hydroxy-2-methylpropyloxy)-5-(2-methoxyphenoxy)-2-(2-pyrimidinyl)-4-pyrimidinyl] benzenesulfonamide, to obtain 3-[6-(4-t-butylphenylsulfonylamino)-5-(2-methoxyphenoxy)-2-(2-pyrimidinyl)-4-pyrimidinyloxy]-2-methylpropionic acid as a pale yellow powder.

$^1$H-NMR(CDCl$_3$, ppm, TMS): 1.11(3H, d, J=7.1 Hz), 1.27(9H, s), 2.81(1H, m), 3.84(3H, s), 4.61(1H, dd, J=10.8.6.1 Hz), 4.70(1H, dd, J=10.8, 5.9 Hz), 6.68(1H, dt, J=7.7, 1.7 Hz), 6.86(1H, dd, J=8.0, 1.2 Hz), 6.94(1H, t, J=8.3, 1.2 Hz), 7.01(1H, d, J=7.6 Hz), 7.42(2H, d, J=8.5 Hz), 7.50(1H, t, J=4.9 Hz), 8.37(2H, m), 9.16(2H, d, J=4.9 Hz) IR(KBr)cm$^{-1}$: 3400, 2965, 1720, 1620, 1560, 1500, 1340, 1255, 1175, 1080, 750

Example 111 (Synthesis of Compound No. 117)

The procedure described in Example 3 was repeated using 4-t-butyl-N-[6-(3-hydroxypropyloxy)-2-(4,6-dimethyl-2-pyrimidinyl)-5-(2-methoxyphenoxy)-4-pyrimidinyl] benzenesulfonamide, to obtain 3-[6-(4-t-butylphenylsulfonylamino)-2-(4,6-dimethyl-2-pyrimidinyl)-5-(2-methoxyphenoxy)-4-pyrimidinyloxy] propionic acid as a white powder.

$^1$H-NMR(CDCl$_3$, ppm, TMS): 1.30(9H, s), 2.66(6H, s), 2.69(2H, t, J=6.5 Hz), 3.91(3H, s), 4.74(2H, t, J=6.5 Hz), 6.79(1H, dt, J=7.8, 1.2 Hz), 6.93(1H, dd, J=8.1 1.2 Hz), 6.98(11H, m), 7.04(1H, t, J=7.7 Hz), 7.12(1H, s), 7.45(2H, d, J=8.8 Hz), 8.37(2H, m) IR(KBr)cm$^{-1}$: 3385, 2965, 1730, 1620, 1580, 1500, 1340, 1255, 1170, 1080, 750

Example 112 (Synthesis of Compound No. 124)

The procedure described in Example 3 was repeated using 4-isopropyl-N-[6-(3-hydroxypropyloxy)-5-(2- methoxyphenoxy)-2-(2-pyrimidinyl)-4-pyrimidinyl]benzenesulfonamide, to obtain 3-[6-(4-t-isopropylphenylsulfonylamino)-5-(2-methoxyphenoxy)-2-(2-pyrimidinyl)-4-pyrimidinyloxy]propionic acid as a pale yellow powder.

$^1$H-NMR(CDCl$_3$-CD$_3$OD, ppm, TMS): 1.23(6H, d, J=7.1 Hz), 2.62(2H, t, J=6.2 Hz), 2.94(1H, sep, J=7.1 Hz), 3.91 (3H, s), 4.74(2H, t, J=6.2 Hz), 6.85(1H, t, J=7.7 Hz), 6.90–7.04(2H, m), 7.10(1H, dt, J=7.7, 1.5 Hz), 7.29(2H, d, J=8.3 Hz), 7.53(1H, t, J=4.6 Hz), 8.33(2H, m), 9.02(2H, d, J=4.6 Hz) IR(KBr)cm$^{-1}$: 3385, 2965, 1730, 1620.1500, 1340, 1255, 1170, 1080, 750

Example 113 (Synthesis of Compound No. 113)

The procedure described in Example 54 was repeated using Compound No. 112 and 2-aminopyridine, to obtain N-(2-pyridyl)-3-[6-(4-t-butylphenylsulfonylamino)-5-(2-methoxyphenoxy)-2-(2-pyrimidinyl)-4-pyrimidinyloxy]-2-methylpropionamide as a pale yellow oil.

$^1$H-NMR(CDCl$_3$, ppm, TMS): 1.19(3H, d, J=6.8 Hz), 1.29(9H, s), 3.04(1H, m), 3.86(3H, s), 4.42(1H, dd, J=10.7, 6.2 Hz), 4.89(1H, dd, J=10.7, 6.7 Hz), 6.67(1H, dt, J=7.2, 1.7 Hz), 6.81–7.16(4H, m), 7.42(2H, d, J=8.5 Hz), 7.43(1H, t, J=4.6 Hz), 7.69(1H, dt, J=7.8, 2.0 Hz), 8.15–8.25(2H, m), 8.36(2H, m), 9.06(2H, d, J=4.6 Hz), 9.14(1H, brs); IR(KBr) cm$^{-1}$: 2965, 1695, 1580, 1560, 1500, 1340, 1255, 1170, 1085, 750

Example 114 (Synthesis of Compound No. 114)

The procedure described in Example 14 was repeated using Compound No. 112 and 2-isopropylaniline, to obtain N-(2-isopropylphenyl)-3-[6-(4-t-butylphenylsulfonylamino)-5-(2-methoxyphenoxy)-2-(2-pyrimidinyl)-4-pyrimidinyloxy]-2-methylpropionamide as a pale yellow oil.

$^1$H-NMR(CDCl$_3$, ppm, TMS): 0.99(3H, d, J=6.8 Hz), 1.01(3H, d, J=6.8 Hz), 1.17(3H, d, J=6.8 Hz), 1.23(9H, s), 2.91–3.08(2H, m), 3.86(3H, s), 4.26(1H, dd, J=11.0, 6.8 Hz), 5.06(1H, dd, J=11.0, 3.8 Hz), 6.77(1H, t, J=7.6 Hz), 6.91(1H, d, J=7.3 Hz), 6.96–7.34(7H, m), 7.38(2H, d, J=8.6 Hz), 8.39(2H, m), 8.49(2H, m), 9.01(1H, brs) IR(KBr)cm$^{-1}$: 2965, 1670, 1580, 1560, 1500, 1345, 1255, 1175, 1080, 755

Example 115 (Synthesis of Compound No. 108)

The procedure described in Example 6 was repeated using Compound No. 3 and methanol, to obtain methyl 3-[6-(4-t-butylphenylsulfonylamino)-5-(2-methoxyphenoxy)-2-(2-pyrimidinyl)-4-pyrimidinyloxy]propionate as a pale yellow oil.

$^1$H-NMR(CDCl$_3$, ppm, TMS): 1.29(9H, s), 2.68(2H, t, J=6.2 Hz), 3.60(3H, s), 3.92(3H, s), 4.77(2H, t, J=6.2 Hz), 6.83(1H, dt, J=7.6, 1.5 Hz), 6.96(1H, d, J=7.1 Hz), 7.02(1H, m), 7.10(1H, t, J=7.6 Hz), 7.42(2H, d, J=8.5 Hz), 7.42(1H, t, J=4.9 Hz), 8.36(2H, m), 9.01(2H, d, J=4.9 Hz); IR(KBr) cm$^{-1}$: 2960, 1740, 1580, 1560, 1500, 1340, 1255, 1175, 1080, 750

Example 116 (Synthesis of Compound No. 115)

The procedure described in Example 14 was repeated using Compound No. 124 and 2-isopropylaniline, to obtain N-(2-isopropylphenyl)-3-[6-(4-isopropylphenylsulfonylamino)-5-(2-methoxyphenoxy)-2-(2-pyrimidinyl)-4-pyrimidinyloxy]propionamide as a pale brown oil.

$^1$H-NMR(CDCl$_3$, ppm, TMS): 1.07(6H, d, J=6.8 Hz), 1.22(6H, d, J=6.8 Hz), 2.86(2H, t, J=6.3 Hz), 2.92(1H, sep, J=6.8 Hz), 3.03(1H, sep, J=6.8 Hz), 3.92(3H, s), 4.93(2H, t, J=6.3 Hz), 6.80(1H, t, J=7.4 Hz), 6.95(1H, d, J=7.6 Hz), 7.00–7.40(7H, m), 8.42(2H, m), 8.59(2H, m), 8.84(2H, m); IR(KBr)cm$^{-1}$: 2965, 1670, 1580, 1560, 1500, 1345, 1255, 1170, 1085, 760

Example 117 (Synthesis of Compound No. 116)

The procedure described in Example 54 was repeated using Compound No. 124 and 2-aminopyridine, to obtain N-(2-pyridyl)-3-[6-(4-isopropylphenylsulfonylamino)-5-(2-methoxyphenoxy)-2-(2-pyrimidinyl)-4-pyrimidinyloxy]propionamide as a pale yellow oil.

$^1$H-NMR(CDCl$_3$, ppm, TMS): 1.22(6H, d, J=6.8 Hz), 2.77(2H, t, J=6.3 Hz), 2.92(1H, sep, J=6.8 Hz), 3.86(3H, s), 4.86(2H, t, J=6.3 Hz), 6.68(1H, dt, J=7.7, 1.5 Hz), 6.86(1H, dd, J=8.1, 1.2 Hz), 6.90–7.06(3H, m), 7.26(2H, d, J=8.6 Hz), 7.42(1H, t, J=4.9 Hz), 7.67(1H, dt, J=7.9, 2.0 Hz), 8.14(1H, d, J=8.3 Hz), 8.25(1H, m), 8.39(2H, m), 8.52(1H, brs), 9.04(2H, d, J=4.9 Hz); IR(KBr)cm$^{-1}$: 2960, 1695, 1580, 1560, 1500, 1340, 1255, 1170, 1085, 750

Example 118 (Synthesis of Compound No. 120)

The procedure described in Example 54 was repeated using Compound No. 117 and 2-aminopyridine, to obtain N-(2-pyridyl)-3-[6-(4-t-butylphenylsulfonylamino)-2-(4,6-dimethyl-2-pyrimidinyl)-5-(2-methoxyphenoxy)-4-pyrimidinyloxy]propionamide as a pale yellow oil.

$^1$H-NMR(CDCl$_3$, ppm, TMS): 1.30(9H, s), 2.66(6H, s), 2.74(2H, t, J=6.1 Hz), 3.84(3H, s), 4.87(2H, t, J=6.1 Hz), 6.65(1H, t, J=7.3 Hz), 6.80–6.98(3H, s), 7.04(1H, m), 7.16 (1H, s), 7.44(2H, d, J=8.3 Hz), 7.69(1H, t, J=7.0 Hz), 8.15(1H, d, J=8.3 Hz), 8.22(1H, d, J=3.9 Hz), 8.38(2H, m), 8.48(1H, brs); IR(KBr)cm$^{-1}$: 2965, 1695, 1620, 1580, 1500, 1345, 1255, 1170, 1085, 750

Example 119 (Synthesis of Compound No. 121)

The procedure described in Example 14 was repeated using Compound No. 117 and 2-isopropylaniline, to obtain N-(2-isopropylphenyl)-3-[6-(4-t-butylphenylsulfonylamino)-2-(4,6-dimethyl-2-pyrimidinyl)-5-(2-methoxyphenoxy)-4-pyrimidinyloxy]propionamide as a pale yellow oil.

$^1$H-NMR(CDCl$_3$, ppm, TMS): 1.04(6H, d, J=6.8 Hz), 1.30(9H, s), 2.54(6H, s), 2.82(2H, t, J=6.2 Hz), 2.88(1H, sep, J=6.8 Hz), 3.86(3H, s), 4.91(2H, t, J=6.2 Hz), 6.67–7.54 (11H, m), 7.75(1H, brs), 8.40(2H, m); IR(KBr)cm$^{-1}$: 2965, 1670, 1620, 1575, 1500, 1345, 1255, 1180, 1085, 755

Example 120 (Synthesis of Compound No. 122)

The procedure described in Example 14 was repeated using Compound No. 118 and 2-isopropylaniline, to obtain N-(2-isopropylphenyl)-3-[6-(4-t-butylphenylsulfonylamino)-2-(4,6-diethoxy-2-pyrimidinyl)-5-(2-methoxyphenoxy)-4-pyrimidinyloxy]propionamide as a pale yellow oil.

$^1$H-NMR(CDCl$_3$, ppm, TMS): 1.07(6H, m), 1.29(9H, s), 1.43(6H, m), 2.71–2.92(3H, m), 3.86(3H, brs), 4.54(4H, m), 4.88(2H, t, J=6.0 Hz), 6.12(1H, s), 6.54–7.52(10H, m), 8.35(2H, m); IR(KBr)cm$^{-1}$: 2965, 1670, 1590, 1500, 1345, 1255, 1180, 1085, 775

Example 121 (Synthesis of Compound No. 123)

The procedure described in Example 14 was repeated using Compound No. 119 and 2-isopropylaniline, to obtain N-(2-isopropylphenyl)-3-[6-(4-t-butylphenylsulfonylamino)-2-(4,6-diisopropyl-2-pyrimidinyl)-5-(2-methoxyphenoxy)-4-pyrimidinyloxy]propionamide as a pale yellow powder.

$^1$H-NMR(CDCl$_3$, ppm, TMS): 1.07(6H, m), 1.30(9H, s), 1.41(12H, d, J=6.1 Hz), 2.75–2.95(3H, m), 3.86(3H, brs), 4.88(2H, t, J=6.0 Hz), 5.52(2H, sep, J=6.1 Hz), 6.05(1H, s), 6.54–7.46(10H, m), 8.32(2H, m); IR(KBr)cm$^{-1}$: 2965, 1670, 1620, 1575.1500, 1345, 1255, 1175, 1105, 775

Example 122 (Synthesis of Compound No. 109)

(1) To 3-benzyloxy-1-propanol (1.66 g) dissolved in acetone (10 ml) was added 2N Jones reagent (10 ml) while cooling on ice, and the mixture was stirred for 4 hours at room temperature. Ethyl acetate was added, and the resultant mixture was washed with water. The organic layer was extracted with a sat. aq. K$_2$CO$_3$, and the aqueous layer was washed with ethyl acetate. The washed material was acidified with dilute HCl, again extracted with ethyl acetate, then washed with saturated brine. Drying over anhydrous magnesium sulfate and concentrating under reduced pressure yielded 1.27 g of 3-benzyloxypropionic acid as a colorless crystals.

$^1$H-NMR(CDCl$_3$, ppm, TMS): 2.67(2H, t, J=6.4 Hz), 3.75(2H, t, J=6.4 Hz), 4.55(2H, s), 7.25–7.38(5H, m) IR(KBr)cm$^{-1}$: 3430, 3032, 2927, 1716, 1455, 1366, 1235, 1201, 1104, 1072, 739, 698

(2) Oxalyl chloride (880 mg) was added to a solution of 3-benzyloxypropionic acid (1.04 g) in benzen (10 ml). Subsequently, dimethylformamide (100 mg) was added. After the resultant mixture was stirred for 30 minutes at room temperature, benzen was distilled off. Azeotropic distillation was performed twice through use of benzen (10 ml), and the resultant residue was dissolved in tetrahydrofuran (10 ml). To the solution were added 3-methyl-3-oxetanyl-methyl alcohol (620 mg) and then triethylamine (620 mg). The mixture was stirred for 5 hours at room temperature. Ethyl acetate was added to the reaction mixture, followed by washing with sat. aq. K$_2$CO$_3$, water, 1N-HCl, water, and saturated brine and then drying over anhydrous magnesium sulfate. The solvent was evaporated under reduced pressure, and the residue was purified by silica gel column chromatography (ethyl acetate-hexane 2:1), to give 1.01 g of 3-methyl-3-oxetanylmethyl 3-benzyloxypropionate as a pale yellow oil.

$^1$H-NMR(CDCl$_3$, ppm, TMS): 1.32(3H, s), 2.67(2H, t, J=6.4 Hz), 3.77(2H, t, J=6.4 Hz), 4.20(2H, s), 4.36(2H, d, J=6.1 Hz), 4.51(2H, t, J=6.1 Hz), 4.53(2H, s), 7.24–7.39(5H, m); IR(CDCl$_3$)cm$^{-1}$: 3012, 2968, 2878, 1736, 1455, 1379, 1365, 1249, 1183, 1103, 1072, 981, 834

(3) 3-Methyl-3-oxetanylmethyl 3-benzyloxypropionate (521 mg) was dissolved in dichloromethane under an argon atmosphere, and trifluoroborane-diethylether was added thereto at −15° C. The mixture was stirred for 5 hours at −15° C. Triethylamine (280 μl) was added to the reaction mixture, and stirring was continued for 15 minutes. Subsequently, diethylether (3 ml) was added. The precipitating crystals were removed from the reaction mixture by filtration, then the mother liquid was concentrated under reduced pressure. The residue was purified by alumina column chromatography (ethyl acetatehexane 1:3), to give 385 mg of 1-(2-benzyloxyethyl)-4-methyl-2,6,7-trioxabicyclo-[2.2.2]octane as a colorless solid.

$^1$H-NMR(CDCl$_3$, ppm, TMS): 0.79(3H, s), 2.07(2H, t, J=7.6 Hz), 3.62(2H, t, J=7.6 Hz), 3.88(6H, s), 4.51(2H, s), 7.27–7.35(5H, m); IR(CHCl$_3$)cm$^{-1}$: 3446, 2937, 2881, 1475, 1454, 1371, 1347, 1252, 1192, 1126, 1099, 1052, 1005, 990, 944, 907, 745

(4) To liquid ammonia (35 ml) was added, under an argon atmosphere, a solution of 1-(2-Benzyloxyethyl)-4-methyl-2,6,7-trioxabicyclo-[2.2.2]octane (3.54 g) in anhydrous tetrahydrofuran (8 ml). Metallic sodium (500 mg) was then added thereto, and the resultant mixture was stirred for 3 hours at −78° C. After ammonium chloride was added to the reaction mixture, ammonia was evaporated, and tetrahydrofuran was evaporated under reduced pressure. The residue was washed with ether, and the resultant solid was added to saturated brine and extracted with ethyl acetate. The organic layer was washed with saturated brine and dried over anhydrous magnesium sulfate. The solvent was evaporated, to give 1-(2-hydroxyethyl)-4-methyl-2,6,7-trioxabicyclo [2.2.2]octane (1.4 g) as a pale yellow oil.

$^1$H-NMR(CDCl$_3$, ppm, TMS): 0.82(3H, s), 1.95(2H, t, J=5.4 Hz), 3.75(2H, brt, J=5.4 Hz), 3.93(6H, s)

(5) Sodium hydride (35 mg) was added to a solution of 1-(2-hydroxyethyl)-4-methyl-2,6,7-trioxabicyclo-[2.2.2]octane (50 mg) in dimethylsulfoxide (2 ml). To the mixture, after being stirred for 10 minutes at room temperature, was added 4-t-butyl-N-[6-chloro-5-(2-methoxyphenoxy)-2-(2-pyrimidinyl)-4-pyrimidinyl]benzenesulfonamide (93 mg). The resultant mixture was stirred for 5 hours at 70° C. After the reaction mixture was cooled, saturated aqueous citric acid solution (200 μl) was added thereto, followed by stirring for 1 hour at room temperature. Ethyl acetate was added to the reaction mixture. The resultant mixture was successively washed with water and saturated brine.

The organic layer was dried over anhydrous magnesium sulfate. The solvent was evaporated under reduced pressure, and the residue was purified by silica gel column chromatography (chloroform-methanol 7:1), to give 40 mg of 3-hydroxy-2-hydroxymethyl-2-methylpropyl 3-[6-(4-t-butylphenyl-sulfonylamino)-5-(2-methoxyphenoxy)-2-(2-pyrimidinyl)-4-pyrimidinyloxy]propionate as a pale yellow oil.

$^1$H-NMR(CDCl$_3$, ppm, TMS): 0.75(3H, s), 1.29(9H, s), 2.75(2H, t, J=6.1 Hz), 3.44(2H, d, J=11.0 Hz), 3.48(2H, d, J=11 Hz), 3.96(3H, s), 4.14(2H, s), 4.81(2H, t, J=6.1 Hz), 6.85(1H, m), 6.95–7.06(2H, m), 7.12(1H, m), 7.37–7.44(3H, m), 3.37(2H, d, J=8.1 Hz), 9.01(2H, d, J=4.9 Hz) IR(KBr) cm$^{-1}$: 3412, 2965, 1735, 1580, 1560, 1500, 1385, 1255, 1175, 1082, 752, 630, 576

The thus-obtained Compound No. 109 was added to HCl-acetone and stirred, to give a Compound No. 3.

Example 123 (Synthesis of Compound No. 118)

(1) Propanediol (532 mg) was dissolved in anhydrous dimethylformamide (5 ml) under an argon atmosphere, and sodium hydride (50% dispersion in oil) (21 mg) was added to the resultant solution at room temperature.

A solution of 4-t-butyl-N-[6-chloro-2-(4,6-dimethoxy-2-pyrimidinyl)-5-(2-methoxyphenoxy)-4-pyrimidinyl]benzenesulfonamide (409 mg) in anhydrous dimethylformamide (2.4 ml) was added dropwise to the above mixture while being cooled on ice. The resultant mixture was stirred for 3.5 hours at 60° C. The reaction mixture was poured into cold 1N HCl, and extracted with ethyl acetate. The organic layer was washed with saturated brine, dried over anhydrous sodium sulfate, then concentrated under reduced pressure. The residue was purified by silica gel column chromatography (chloroform/methanol=20/1) to give obtain 4-t-butyl-N-[2-(4,6-di(3-hydroxypropyloxy)-2-pyrimidinyl)-6-(3-hydroxypropyloxy)-5-(2-methoxyphenoxy)-4-pyrimidinyl]benzenesulfonamide (250 mg) as a colorless oil.

(2) To a solution of anhydrous ethanol (0.0246 ml) in anhydrous dimethylformamide (1 ml) was added, under an argon atmosphere, sodium hydride (50% dispersion in oil) (6 mg) at room temperature. A solution of 4-t-butyl-N-[2-(4, 6-di(3-hydroxypropyloxy)-2-pyrimidinyl)-6-(3-hydroxypropyloxy)-5-(2-methoxyphenoxy)-4-pyrimidinyl] benzenesulfonamide (15 mg) in anhydrous dimethylformamide (0.7 ml) was added dropwise to the above mixture while being cooled on ice. The resultant mixture was stirred for 1.5 hours at room temperature.

The reaction mixture was poured into cold 1N HCl, and extracted with ethyl acetate. The organic layer was washed with saturated brine, dried over anhydrous sodium sulfate, then concentrated under reduced pressure. The residue was purified by silica gel preparative thin-layer chromatography (chloroform/methanol =15/1) to give 4-t-butyl-N-[2-(4,6-diethoxy-2-pyrimidinyl)-6-(3-hydroxypropyloxy)-5-(2-methoxyphenoxy)-4-pyrimidinyl]benzenesulfonamide (8 mg) as a colorless oil.

(3)

The procedure described in Example 3 was repeated using 4-t-butyl-N-[2-(4,6-diethoxy-2-pyrimidinyl)-6-(3-hydroxypropyloxy)-5-(2-methoxyphenoxy)-4-pyrimidinyl]benzenesulfonamide (19 mg), to obtain 3-[6-(4-t-butylphenylsulfonylamino)-2-(4, 6-diethoxy-2-pyrimidinyl)-5-(2-methoxyphenoxy)-4-pyrimidinyloxy]propionic acid (9.1 mg) as a colorless oil.

$^1$H-NMR(CDCl$_3$, ppm, TMS): 1.29(9H, s), 1.45(6H, t, J=7.0 Hz), 2.76(2H, t, J=6.3 Hz), 3.87(3H, s), 4.56(4H, q, J=7.0 Hz), 4.73(2H, t, J=6.3 Hz), 6.12(1H, s), 6.73–7.07(4H, m), 7.38(2H, d, J=8.9 Hz), 8.07–8.28(2H, br); IR(CHCl$_3$) cm$^{-1}$: 3520, 3373, 3201, 2967, 1719, 1619, 1592, 1576

Example 124 (Synthesis of Compound No. 119)

The procedure described in Example 123 was repeated using 4-t-butyl-N-[2-(4,6-di(3-hydroxypropyloxy)-2-pyrimidinyl)-6-(3-hydroxypropyloxy)-5-(2-methoxyphenoxy)-4-pyrimidinyl]-benzenesulfonamide and isopropyl alcohol, to obtain 3-[6-(4-t-butylphenylsulfonylamino)-2-(4,6-diisopropyloxy-2-pyrimidinyl)-5-(2-methoxyphenoxy)-4-pyrimidinyloxy]propionic acid (23 mg) as a pale yellow oil.

$^1$H-NMR(CDCl$_3$, ppm, TMS): 1.35(9H, s), 1.47(12H, d, J=6.3 Hz), 2.84(2H, t, J=6.0 Hz), 3.92(3H, s), 4.79(2H, t, J=6.0 Hz), 5.51–5.65(2H, m), 6.11(1H, s), 6.76–7.12(4H, m), 7.43(2H, d, J=8.5 Hz), 8.04–8.28(2H, br) IR(CHCl$_3$) cm$^{-1}$: 3516, 3367, 2968, 1719, 1619, 1591, 1575

Example 125 (Synthesis of Compound No. 125)

(1) Compound No. 2(135 mg) and N,O-dimethylhydroxyamine.HCl (93 mg) were dissolved in DMF (3 ml). Triethylamine (0.30 ml) and 50% propanephosphonic acid anhydride in ethyl acetate (0.12 ml) were added thereto while being cooled on ice. The mixture was stirred for 1 hour while being cooled on ice, and then overnight at room temperature.

The reaction mixture was concentrated under reduced pressure. The residue was extracted with ethyl acetate and washed, with 1N HCl, sat. aq. NaHCO$_3$, water, and saturated brine, dryed over anhydrous sodium sulfate and concentration under reduced pressure to give 111 mg of N-methyl-N-methoxy-[6-(4-t-butylphenylsulfonylamino)-5-(2-methoxyphenoxy)-2-(2-pyrimidinyl)-4-pyrimidinyloxy]acetamide (yield 79%) as a colorless powder.

(2) N-methyl-N-methoxy-[6-(4-t-butylphenylsulfonylamino)-5-(2-methoxyphenyl)-2-(2-pyrimidinyl)-4-pyrimidinyloxy]acetamide (36 mg) was dissolved in anhydrous THF (2 ml) under an argon atmosphere. To the solution was added dropwise a solution (0.079 ml) of 3N-methylmagnesium bromide in ether at −30° C. The mixture was stirred at −30° C. for 20 minutes.

Saturated ammonia water was added, and extracted with ethyl acetate. The aqueous layer was acidified with 2N HCl, and extracted with ethyl acetate. The organic layers were combined together, washed with saturated brine, dried over anhydrous sodium sulfate, and concentrated under reduced pressure.

The residue was purified by silica gel preparative thin-layer chromatography (chloroform/ethyl alcohol=5/1), to give 4-t-butyl-N-[5-(2-methoxyphenoxy)-6-(2-oxopropyloxy)-2-(2-pyrimidinyl)-4-pyrimidinyl]benzenesulfonamide (16 mg) as a pale yellow powder (yield 47%).

$^1$H-NMR(CDCl$_3$, ppm, TMS): 1.29(9H, s), 2.12(3H, s), 3.96(3H, s), 5.09(2H, s), 6.84–7.16(4H, m), 7.40–7.45(3H, m), 8.38(2H, brs), 8.99(2H, d, J=4.8 Hz); IR(CHCl$_3$)cm$^{-1}$: 3371, 3198, 2968, 1739, 1580, 1559, 1499, 1470

Test Example 1

Endothelin Binding Inhibition Experiment

Preparation of receptor membrane samples (ET$_A$) from smooth muscles of porcine thoracic aorta:

Porcine thoracic aorta which was separated from the fatty tissue and then was removed endothelium with gauze was minced, and then homogenized in three times the volume of Tris-HCl buffer (pH 7.4) (buffer A) containing 0.25 M sucrose, 3 mM ethylenediaminetetraacetic acid, 5 μg/ml of aprotinin, 10 μg/ml of pepstatin A, 10 μg/ml of leupeptin, and 0.1 μM p-amidinophenyl-methanesulfonyl fluoride. After centrifugation for 30 minutes at 1,000×g, the supernatant was further centrifuged for 30 minutes at 100,000×g. The pellets were suspended in buffer A, and recentrifuged for 30 minutes at 100,000×g. The pellets were suspended in buffer A and the suspension was stored at −80° C.

$^{125}$I-Endothelin-1 Binding Assay:

The thus-obtained membrane sample (1 μl) was incubated together with $^{125}$I-endothelin-1 (2×10$^{-11}$ M) and various concentrations of the compounds, for 2 hours at 25° C., in 250 μl in total volume of 50 mM Tris-HCl buffer (pH 7.4) containing 0.5 % bovine serum albumin. The incubated mixture was filtered by use of an HVPP filters (pore size 0.45 μm, product of Milipore). The filters were washed with cold buffer A four times, and then measured with a gamma-ray counter (Aroka Autowell Gamma System ARC-251). Preparation of receptor membrane sample (ET$_B$) from rat brain and assay of $^{125}$I endothelin-1:

Rat brain tissue was minced, and a crude receptor membrane sample was prepared in a manner similar to that used in the aforementioned case of porcine thoracic aorta. Also, $^{125}$I-endothelin-1 assay was performed in the same manner as described above.

The results of the thus-performed endothelin binding inhibition experiment for each of the two receptors are shown in Table 10.

TABLE 10

| Compound No. | IC$_{50}$ ($\mu$M) ET$_A$ | ET$_B$ |
|---|---|---|
| 2 | 9.4 | 0.8 |
| 9 | 0.72 | 2.9 |
| 10 | 0.51 | 0.65 |
| 12 | 0.32 | 0.82 |
| 14 | 0.82 | 0.0028 |
| 15 | 3.2 | 0.016 |
| 18 | 0.15 | 0.023 |
| 25 | 1.9 | 0.037 |
| 29 | 3.1 | 0.03 |
| 34 | 0.39 | 0.22 |
| 38 | 16.9 | 0.019 |
| 48 | 0.16 | 0.00075 |
| 53 | 0.098 | 0.00082 |
| 92 | 0.0095 | 0.1 |

Test Example 2

1) ET$_A$ Receptor Antagonizing Action

The thoracic aorta was removed from a male SD rat, and ring sample of the aorta each having a width of 3 mm were prepared. Each ring, while subjected to a static tension of 2 g, was suspended in an organ bath filled with a 37° C. Krebs-Henseleit solution (NaCl 118.4 mM, KCl 14.7 mM, CaCl$_2$ 2.5 mM, MgSO$_4$ 1.2 mM, KH$_2$PO$_4$ 1.2 mM, NaHCO$_3$ 25.0 mM, glucose 10.0 mM aerated with a gas mixture of 95% O$_2$ and 5% CO$_2$. The vascular sample was pretreated for 20 minutes by use of either $10^{-7}$–$10^{-5}$ M Compound No. 92 or a solvent therefor. Subsequently, endothelin-1 dissolved in brine containing 0.1% bovine serum albumin was added in a cumulative manner, and isometric contraction was observed in the range of 1 to 100 ng/ml ($4 \times 10^{-9}$ to $4 \times 10^{-8}$ M) of endothelin, to thereby investigate the effects of the compounds. FIG.1 shows contraction responses (%) normalized with respect to the contraction response obtained through application of 80 mM KCl.

2) ET$_B$ Receptor Antagonizing Action

Figure 2:
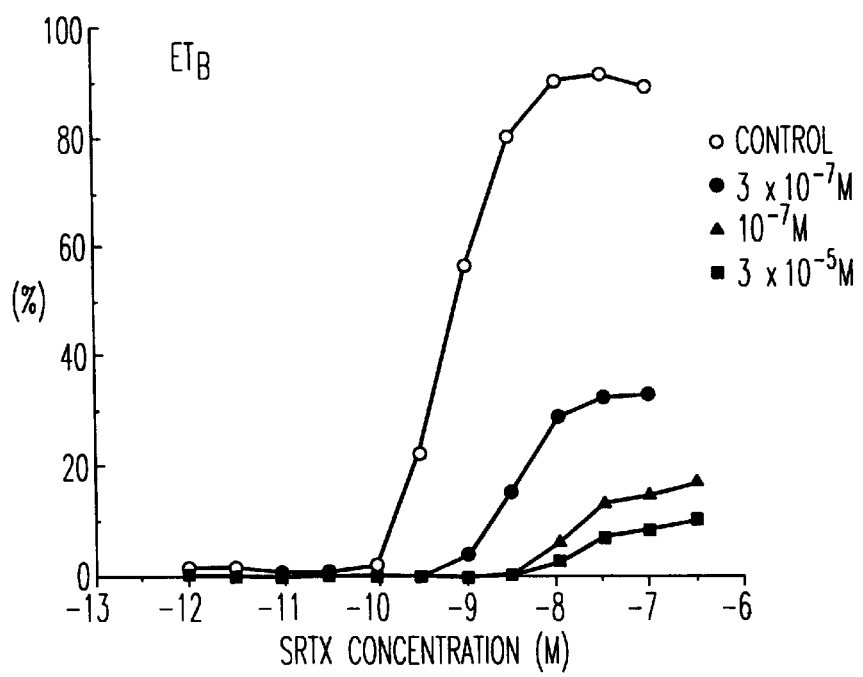
FIG. 2 is a graph showing the $ET_B$ receptor antagonism of Compound No. 68.

The pulmonary artery was removed from a male NZW rabbit, and each of arterial samples prepared as described above was suspended in an organ bath in a manner similar to that described above, with the application of a static tension of 1 g. The sample was pretreated for 30 minutes by use of either $3 \times 10^{-8}$–$3 \times 10^{-7}$ M Compound No. 68 or a solvent therefor. Subsequently, sarafotoxin (SRTX) S6c, which is a selective agonist for ET$_B$ receptor, was added was added in a cumulative manner, and isometric contraction was observed in the range of $10^{-12}$ to $3 \times 10^{-7}$ M sarafotoxin S6c, to thereby investigate the effects of the compounds. FIG.2 shows contraction responses (%) normalized with respect to the contraction response obtained through application of 60 mM KCl.

From the above experiments, it was found that the compounds of the present invention exhibit remarkable antagonizing action on ET$_A$ and ET$_B$ receptors present in vascular samples.

Industrial Applicability

The novel pyrimidine derivatives (1) of the present invention exhibit strong binding inhibitory activity against endothelin having very strong vasoconstrictive effect and cell proliferation effect. Therefore, the compounds are effective as remedies for various endothelin-related diseases and disorders including heart diseases such as ischemic heart infarction, congestive heart failure, arrhythmia, and unstable angina; airway diseases such as asthma; hypertonia such as pulmonary hypertension, renal hypertension, and hypertension accompanying organ transplantation; circulatory diseases such as subarachnoid hemorrhage and vasospasm; kidney diseases such as acute and chronic renal failure; diabetes, hyperlipemia, and other diseases that are accompanied by vascular lesion; arteriosclerosis; liver diseases such as alcohol-induced liver disorders; gastrointestinal disorders such as those of gastric mucosa; bone diseases; prostatic hypertrophy; urinary disorders; cancer; and skin diseases concurrent with proliferation of melanocytes.

We claim:

1. A pyrimidine derivative of the following formula (1) or a salt of the derivative:

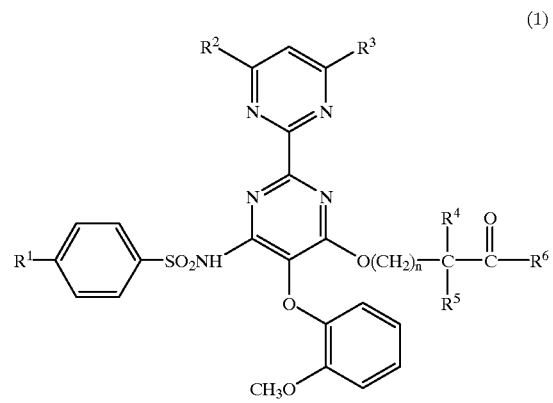

wherein R$^1$ represents a lower alkyl group; each of R$^2$ and R$^3$, which are identical to or different from each other, represents a hydrogen atom, a lower alkyl group, or a lower alkoxyl group; each of R$^4$ and R$^5$, which are identical to or different from each other, represents a hydrogen atom or a lower alkyl group; R$^6$ represents a lower alkyl group, —OR$^7$, or —NR$^8$R$^9$; and n is a number between 0 and 3 inclusive;

wherein R$^7$ represents:

a hydrogen atom;

a lower alkyl group;

a phenyl group which may have a substituent, the substituent selected from the group consisting of C$_{1-6}$ alkyl groups, C$_{1-6}$ alkoxyl groups, and a halogen atom;

an aralkyl group which may have a substituent, the group being selected from the group consisting of phenylalkyl group, naphthylalkyl group, biphenylalkyl group and indanyl group, and the substituent being selected from the group consisting of hydroxy, C$_1$–C$_6$ alkyl C$_1$–C$_6$ alkoxyl, C$_1$–C$_3$ alkylenedioxy, halogen, nitro, trifluoromethyl, and cyano; and each of R$^8$ and R$^9$, which are identical to or different from each other, represents:

a hydrogen atom;

a hydroxyl group;

a lower alkyl group which may have a substituent, the group being selected from the group consisting of a linear, branched or cyclic alkyl group having 1–6 carbon atoms, the substituent being one to three halogen atoms or hydroxyl groups;

a lower alkenyl group which may have a substituent, the group being selected from the group consisting of linear, branched, or cyclic alkenyl group having 2–6 carbon atoms, the substituent being one to three halogen atoms or hydroxyl groups;

an aryl group which may have a substituent, the group being selected from the group consisting of phenyl and naphthyl, the substituent being one to three $C_{1-6}$ alkyl groups, $C_{2-6}$ alkenyl groups, $C_{1-6}$ alkoxyl groups, $C_{1-6}$ alkylthio groups, halogen atoms, hydroxy groups, amino groups, nitro groups, alkoxycarbonyl groups or $C_{1-6}$ haloalkyl groups;

an aralkyl group which may have a substituent, the group being selected from the group consisting of phenylalkyl group, naphthylalkyl group, biphenylalkyl group and indanyl group, and the substituent being selected from the group consisting of hydroxy, $C_1$–$C_6$ alkyl, $C_1$–$C_6$ alkoxyl, $C_1$–$C_3$ alkylenedioxy, halogen, nitro, trifluoromethyl, and cyano;

an amino group which may have a substituent, the substituent being selected from the group consisting of phenyl, $C_1$–$C_6$ alkyl substituted phenyl, pyridyl, and $C_1$–$C_6$ alkyl; or a heterocyclic group or heterocyclic alkyl group, which may have a substituent, the group being selected from the group consisting of furyl group, thienyl group, pyrazolyl group, thiazolyl group, thiadiazolyl group, imidazolyl group, pyridyl group, pyrimidinyl group, pyrazinyl group, furylalkyl group, thienylalkyl group, pyrazolylalkyl group, thiazolylalkyl group, imidazolylalkyl group, pyridylalkyl group and pyrimidinylalkyl group, the substituent being selected from the group consisting of $C_1$–$C_6$ alkyl, $C_1$–$C_6$ alkoxyl, $C_1$–$C_6$ haloalkyl, and halogen;

or $R^8$ and $R^9$ may be linked to each other so as to form a 5-to 7-membered ring along with their adjacent nitrogen atom.

2. A pyrimidine derivative as described in claim 1 or a salt of the derivative, wherein $R^1$ is an isopropyl group or a tert-butyl group.

3. A pharmaceutical composition comprising a pyrimidine derivative as described in claim 1 or a salt of the derivative and a pharmaceutically acceptable carrier.

4. The pyrimidine derivative as described in claim 1 or a salt of the derivative, wherein:

the phenyl group which may have a substituent is selected from the group consisting of methylphenyl, ethylphenyl, isopropylphenyl, methoxyphenyl, ethoxyphenyl, chlorophenyl, bromophenyl and fluorophenyl;

the aralkyl group which may have a substituent is selected from the group consisting of benzyl phenethyl, phenylpropyl, naphthylmethyl, naphthylethyl, biphenylmethyl and indan-1-yl groups, these groups being optionally further substituted by one to three groups selected from the groups consisting of chloro, fluoro, methoxy, ethoxy, methyl, ethyl, nitro, cyano and trifluoromethyl groups;

the lower alkenyl group which may have a substituent is selected from the group consisting of vinyl, propenyl and isobutenyl groups;

the aryl group which may have a substituent is selected from the group consisting of phenyl, naphthyl, mono- or di-chlorophenyl, mono- or di-fluorophenyl, mono-, di-, or tri-methoxyphenyl, mono- or di-methylphenyl, mono- or di-ethylphenyl, mono- or di-isopropylphenyl, tert-butylphenyl, isopropenylphenyl, hydroxyphenyl, nitrophenyl, aminophenyl, ethoxycarbonylphenyl and methylthiophenyl;

the amino group which may have a substituent is selected from the group consisting of phenylamino, $C_{1-6}$ alkyl-substituted phenylamino, pyridylamino, and $C_{1-6}$ alkylamino groups;

the heterocyclic group which may have a substituent and the heterocyclic-alkyl group which may have a substituent is selected from the group consisting of furyl, thienyl, pyrazolyl, thiazolyl, pyridyl, pyrimidinyl, pyrazinyl furfuryl, thienylmethyl, pyrazolylmethyl, thiazolylmethyl, imidazolylmethyl, pyridylmethyl and pyrimidinylmethyl groups, all of which groups is optionally further substituted by a group selected from the group consisting of methyl, ethyl, methoxy, ethoxy, chloro, fluoro and trifluoromethyl;

the 5-to 7-membered ring formed by —$NR^8R^9$ is selected from the group consisting of pyrrolidinyl, piperidinyl, and perhydroazepinyl groups.

5. The pyrimidine derivative as described in claim 1, the pyrimidine derivative being any one of N-(2-isopropylphenyl)-3-[6-(4-t-butylphenylsulfonylamino)-5-(2-methoxyphenoxy)-2-(2-pyrimidinyl)-4-pyrimidinyloxy]propionamide, N-(2-pyridyl)-3-[6-(4-t-butylphenylsulfonylamino)-5-(2-methoxyphenoxy)-2-(2-pyrimidinyl)-4-pyrimidinyloxy]propionamide, N-(2,6-dimethylphenyl)-3-[6-(4-t-butylphenylsulfonylamino)-5-(2-methoxyphenoxy)-2-(2-pyrimidinyl)-4-pyrimidinyloxy]propionamide, N-(2-pyridyly)-4-[6-(4-t-butylphenylsulfonylamino)-5-(2-methoxyphenoxy)-2-(2-pyrimidinyl)-4-pyrimidinyloxy]butyramide, N-(2-pyrazinyl)-3-[6-(4-t-butylphenylsulfonylamino)-5-(2-methoxyphenoxy)-2-(2-pyrimidinyl)-4-pyrimidinyloxy]propionamide, N-(2-thiazolyl)-3-[6-(4-t-butylphenylsulfonylamino)-5-(2-methoxyphenoxy)-2-(2-pyrimidinyl)-4-pyrimidinyloxy]propionamide, N-(2-methylallyl)-3-[6-(4-t-butylphenylsulfonylamino)-5-(2-methoxyphenoxy)-2-(2-pyrimidinyl)-4-pyrimidinyloxy]propionamide, or N-(2-pyridyl)-3-[6-(4-t-butylphenylsulfonylamino)-2-(4,6-dimethyl-2-pyrimidinyl)-5-2-methoxyphenoxy)-4-pyrimidinyloxy]propionamide.

6. A pharmaceutical composition comprising a pyrimidine derivative as described in claim 2 or a salt of the derivative and a pharmaceutically acceptable carrier.

* * * * *

UNITED STATES PATENT AND TRADEMARK OFFICE
CERTIFICATE OF CORRECTION

PATENT NO. : 6,008,224

DATED : December 28, 1999

INVENTOR(S): Mitsuteru HIRATA, ET AL.

It is certified that an error appears in the above-identified patent and that said Letters Patent is hereby corrected as shown below:

Column 65,   line 50 "benzyl phenethyl" should read --benzyl, phenethyl--.

Column 66,   line 17 "pyrazinyl furfuryl" should read --pyrazinyl, furfuryl--.

Column 66,   line 40 "2-pyridyly" should read --2-pyridyl--.

Signed and Sealed this

Eighth Day of May, 2001

*Attest:*

NICHOLAS P. GODICI

*Attesting Officer*   *Acting Director of the United States Patent and Trademark Office*